(12) United States Patent
Zimmerman et al.

(10) Patent No.: US 12,426,982 B2
(45) Date of Patent: *Sep. 30, 2025

(54) SURGICAL TOOL AND ASSEMBLY

(71) Applicant: FlexDex, Inc., Brighton, MI (US)

(72) Inventors: Zachary R. Zimmerman, Northville, MI (US); Gregory Brian Bowles, Fenton, MI (US); Deepak Sharma, Ann Arbor, MI (US); Matthew P. Weber, Brighton, MI (US); Christopher Paul Huang Shu, Ann Arbor, MI (US); James Duncan Geiger, Ottawa Hills, OH (US)

(73) Assignee: FlexDex, Inc., Brighton, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/629,142

(22) Filed: Apr. 8, 2024

(65) Prior Publication Data
US 2024/0245485 A1    Jul. 25, 2024

Related U.S. Application Data

(63) Continuation of application No. 17/337,012, filed on Jun. 2, 2021, now Pat. No. 11,950,966.

(60) Provisional application No. 63/033,499, filed on Jun. 2, 2020.

(51) Int. Cl.
A61B 90/11 (2016.01)
A61B 17/00 (2006.01)

(52) U.S. Cl.
CPC ........ *A61B 90/11* (2016.02); *A61B 17/00234* (2013.01); *A61B 2017/00367* (2013.01); *A61B 2017/00424* (2013.01)

(58) Field of Classification Search
CPC .. A61B 17/320758; A61B 2017/00199; A61B 2017/0042; A61B 2017/00526; A61B 2017/00964; A61B 2017/320004; A61B 2017/00336; A61B 2017/00398; A61B 2017/00477; A61B 2017/00876; A61B 2017/22049
See application file for complete search history.

(56) References Cited

U.S. PATENT DOCUMENTS 11,950,966 B2 *  4/2024  Zimmerman .......... A61B 90/11

* cited by examiner

*Primary Examiner* — Shaun L David
*Assistant Examiner* — Rachael L Geiger
(74) *Attorney, Agent, or Firm* — REISING ETHINGTON, P.C.

(57) ABSTRACT

Surgical tools and assemblies are employed for use in minimally invasive surgical (MIS) procedures. A surgical tool assembly includes a handle assembly and a frame assembly. The handle assembly and frame assembly are designed and constructed to have an articulation input joint and a grounding joint between them. A pitch rotational degree of freedom and a yaw rotational degree of freedom are provided by way of the articulation input joint. The handle assembly is translationally constrained relative to the frame assembly by way of the grounding joint. Intermediate bodies and joints can be provided in certain surgical tool assemblies and architectures.

18 Claims, 40 Drawing Sheets

|  | Surgical Tool Architecture | Articulation Input Joint Properties | | Grounding Joint Properties | |
|---|---|---|---|---|---|
|  |  | Kinematics: Serial (SK) or Parallel (PK) | Virtual Center or Non-Virtual Center | Kinematics: Serial (SK) or Parallel (PK) | Virtual Center or Non-Virtual Center |
| P1 | I | PK | VC | SK | VC |
|  | II | SK | Non-VC | SK | VC |
|  | III | PK | VC | PK* | VC |
|  | IV | SK | Non-VC | PK* | VC |
| P4 | V | SK | VC | SK | VC |
| * The joint provides a 1 DoC along the shaft axis 30 | | | | | |

FIG. 3

SURGICAL TOOL AND ASSEMBLY

INTRODUCTION

This application relates generally to surgical tools that can be employed for use in minimally invasive surgical (MIS) procedures and, more particularly, to surgical tools with a handle and a frame and an input joint situated therebetween.

Surgical tools are often designed and constructed with various components to have certain kinematic architectures at the handle and frame, and to ultimately furnish certain functionalities and performances at an end effector. Particular functionality assets and drawbacks can arise among the architectures depending on how the handle and frame and components are arranged and configured with respect to one another.

SUMMARY

In an embodiment, a surgical tool assembly may include a handle assembly, a frame assembly, an articulation input joint, and an axial grounding joint. The frame assembly has a shaft. The shaft establishes an x-axis. The articulation input joint is situated between the handle assembly and the frame assembly. The articulation input joint provides a pitch rotation between the handle assembly and the frame assembly. The articulation input joint provides a yaw rotation between the handle assembly and the frame assembly. The articulation input joint establishes a first virtual center. The axial grounding joint is situated between the handle assembly and the frame assembly. The handle assembly has a translational constraint along the x-axis with respect to the frame assembly by way of the axial grounding joint. The axial grounding joint establishes a second virtual center.

In an embodiment, a pitch motion path of the articulation input joint and a yaw motion path of the articulation input joint exhibit a parallel kinematic arrangement with respect to each other.

In an embodiment, a pitch motion path of the articulation input joint and a yaw motion path of the articulation input joint exhibit a serial kinematic arrangement with respect to each other.

In an embodiment, rigid body motion transmission paths effected and furnished by way of the axial grounding joint exhibit a parallel kinematic arrangement.

In an embodiment, rigid body motion transmission paths effected and furnished by way of the axial grounding joint exhibit a serial kinematic arrangement.

In an embodiment, the handle assembly is translationally constrained along a y-axis with respect to the frame assembly by way of the axial grounding joint.

In an embodiment, the handle assembly is translationally constrained along a z-axis with respect to the frame assembly by way of the axial grounding joint.

In an embodiment, the articulation input joint and the axial grounding joint exhibit a parallel arrangement with respect to each other between the handle assembly and the frame assembly.

In an embodiment, the first virtual center of the articulation input joint and the second virtual center of the axial grounding joint exhibit a generally coincident arrangement with respect to each other.

In an embodiment, an axis of the handle assembly exhibits a generally intersecting arrangement with the first virtual center and with the second virtual center.

In an embodiment, the shaft's x-axis exhibits a generally intersecting arrangement with the first virtual center and with the second virtual center.

In an embodiment, the first virtual center of the articulation input joint resides at a location that is occupied by the handle assembly, or that is occupied by a user's hand when the user is manipulating the handle assembly during use of the surgical tool assembly, or that is occupied by both the handle assembly and by a user's hand when the user is manipulating the handle assembly during use of the surgical tool assembly.

In an embodiment, the second virtual center of the axial grounding joint resides at a location that is occupied by the handle assembly, or that is occupied by a user's hand when the user is manipulating the handle assembly during use of the surgical tool assembly, or that is occupied by both the handle assembly and by a user's hand when the user is manipulating the handle assembly during use of the surgical tool assembly.

In an embodiment, a first intermediate body is provided and a second intermediate body is provided. The first intermediate body extends from the handle assembly. The first intermediate body and the second intermediate body are connected to each other by way of a first joint. The first intermediate body has a first pitch or yaw rotational degree of freedom with respect to the second intermediate body by way of the first joint.

In an embodiment, a third intermediate body is provided. The second intermediate body and the third intermediate body are connected to each other by way of a second joint. The second intermediate body has a second pitch or yaw rotational degree of freedom with respect to the third intermediate body by way of the second joint. The first and second pitch or yaw rotational degrees of freedom are contrary with respect to each other, and opposite in nature relative to each other.

In an embodiment, the third intermediate body extends from a frame of the frame assembly.

In an embodiment, the first intermediate body is fixed to the handle assembly. The third intermediate body is fixed to the shaft.

In an embodiment, the surgical tool assembly is a handheld surgical tool assembly. The surgical tool assembly lacks a wrist grounding component that would otherwise be utilized during use of the surgical tool assembly.

In an embodiment, a surgical tool assembly may include a handle assembly, a frame assembly, one or more intermediate bodies, multiple joints, an articulation input joint, and a grounding joint. The intermediate body(ies) is coupled between the handle assembly and the frame assembly. The joints reside among the handle assembly, the frame assembly, and the intermediate body(ies). The articulation input joint is established between the handle assembly and the frame assembly by way of the intermediate body(ies) and by way of the joints. The articulation input joint provides a pitch rotational degree of freedom, or provides a yaw rotational degree of freedom, or provides both a pitch and a yaw rotational degree of freedom at one or more of the joints. The articulation input joint further provides a pitch rotational degree of freedom, or provides a yaw rotational degree of freedom, or provides both a pitch and a yaw rotational degree of freedom at one or more of another of the joints. The articulation input joint has a first virtual center. The grounding joint is established between the handle assembly and the frame assembly by way of the intermediate body(ies) and by way of the joints. The grounding joint has a second virtual center.

In an embodiment, the first virtual center of the articulation input joint and the second virtual center of the grounding joint exhibit a generally coincident arrangement with respect to each other.

In an embodiment, the handle assembly establishes a first axis. A shaft of the frame assembly establishes a second axis. The first axis generally intersects the first virtual center of the articulation input joint and generally intersects the second virtual center of the grounding joint. Likewise, the second axis generally intersects the first virtual center of the articulation input joint and generally intersects the second virtual center of the grounding joint.

In an embodiment, the handle assembly is translationally constrained along an x-axis with respect to the frame assembly by way of the grounding joint. The handle assembly is translationally constrained along a y-axis with respect to the frame assembly by way of the grounding joint. And the handle assembly is translationally constrained along a z-axis relative to the frame assembly by way of the grounding joint.

In an embodiment, the articulation input joint and the grounding joint exhibit a parallel arrangement with respect to each other between the handle assembly and the frame assembly.

In an embodiment, the joints include a first joint and a second joint. The first joint resides between the handle assembly and the intermediate body(ies). The first joint provides the pitch rotational degree of freedom or provides the yaw rotational degree of freedom. The second joint resides between the frame assembly and the intermediate body(ies). The second joint provides the other of the pitch rotational degree of freedom or the yaw rotational degree of freedom, whichever is contrary to that provided by the first joint.

In an embodiment, the intermediate body(ies) includes a first intermediate body, a second intermediate body, and a third intermediate body. The joints include a first joint and a second joint. The first intermediate body is an extension of the handle assembly. The second intermediate body is an extension of the frame assembly. The first joint resides between the first intermediate body and the third intermediate body. The second joint resides between the second intermediate body and the third intermediate body. The first joint provides the pitch rotational degree of freedom or provides the yaw rotational degree of freedom of the first intermediate body with respect to the third intermediate body. The second joint provides the other of the pitch rotational degree of freedom or the yaw rotational degree of freedom, whichever is contrary to that provided by the first joint, of the third intermediate body with respect to the second intermediate body.

In an embodiment, the first virtual center of the articulation input joint resides at a location that is occupied by the handle assembly, or that is occupied by a user's hand when the user is manipulating the handle assembly during use of the surgical tool assembly, or that is occupied by both the handle assembly and by a user's hand when the user is manipulating the handle assembly during use of the surgical tool assembly. In a similar manner, the second virtual center of the grounding joint resides at a location that is occupied by the handle assembly, or that is occupied by a user's hand when the user is manipulating the handle assembly during use of the surgical tool assembly, or that is occupied by both the handle assembly and by a user's hand when the user is manipulating the handle assembly during use of the surgical tool assembly.

In an embodiment, a surgical tool assembly may include a handle assembly, a frame assembly, a first intermediate rigid body, a second intermediate rigid body, a third intermediate rigid body, a first joint, and a second joint. The first intermediate rigid body extends from the handle assembly. The second intermediate rigid body extends from the frame assembly. The first joint resides between the first intermediate rigid body and the third intermediate rigid body. The first joint provides a pitch rotational degree of freedom, or provides a yaw rotational degree of freedom, or provides both a pitch and a yaw rotational degree of freedom of the first intermediate rigid body with respect to the third intermediate rigid body. The second joint resides between the second intermediate rigid body and the third intermediate rigid body. The second joint provides a pitch rotational degree of freedom, or provides a yaw rotational degree of freedom, or provides both a pitch and a yaw rotational degree of freedom of the third intermediate rigid body with respect to the second intermediate rigid body. A virtual center of rotation is established, at least in part, by the first joint and by the second joint. The virtual center of rotation resides at a location that is occupied by the handle assembly, or that is occupied by a user's hand when the user is manipulating the handle assembly during use of the surgical tool assembly, or that is occupied by both the handle assembly and by the user's hand when the user is manipulating the handle assembly during use of the surgical tool assembly.

In an embodiment, an articulation input joint is established between the handle assembly and the frame assembly by way of the first intermediate rigid body, the second intermediate rigid body, and the third intermediate rigid body, and by way of the first joint and the second joint. The articulation input joint has the virtual center of rotation. A grounding joint is established between the handle assembly and the frame assembly by way of one or more of the first intermediate rigid body, the second intermediate body, and/or the third intermediate body. The grounding joint has a second virtual center. The virtual center of rotation of the articulation input joint and the second virtual center of the grounding joint exhibit a generally coincident arrangement with respect to each other.

In an embodiment, the second virtual center of the grounding joint resides at the location that is occupied by the handle assembly, or that is occupied by the user's hand when the user is manipulating the handle assembly during use of the surgical tool assembly, or that is occupied by both the handle assembly and by the user's hand when the user is manipulating the handle assembly during use of the surgical tool assembly.

In an embodiment, the handle assembly establishes a first axis. A shaft of the frame assembly establishes a second axis. The first axis generally intersects the virtual center of rotation of the articulation input joint and generally intersects the second virtual center of the grounding joint. The second axis generally intersects the virtual center of rotation of the articulation input joint and generally intersects the second virtual center of the grounding joint.

In an embodiment, the handle assembly is translationally constrained along an x-axis with respect to the frame assembly by way of the grounding joint. The handle assembly is translationally constrained along a y-axis with respect to the frame assembly by way of the grounding joint. And the handle assembly is translationally constrained along a z-axis relative to the frame assembly by way of the grounding joint.

In an embodiment, the articulation input joint and the grounding joint exhibit a parallel arrangement with respect to each other between the handle assembly and the frame assembly.

In an embodiment, an articulation input joint is established between the handle assembly and the frame assembly by way of the first intermediate rigid body, the second intermediate rigid body, and the third intermediate rigid body, and by way of the first joint and the second joint. A pitch motion path of the articulation input joint and a yaw motion path of the articulation input joint exhibit a serial kinematic arrangement with respect to each other. A grounding joint is established between the handle assembly and the frame assembly by way of one or more of the first intermediate rigid body, the second intermediate body, and/or the third intermediate body. Rigid body motion transmission paths effected and furnished by way of the grounding joint exhibit a serial kinematic arrangement.

Various embodiments of a surgical tool assembly may include one or more or any technically-feasible combinations of any of the recitations and subject matter set forth in paragraphs of this summary section.

BRIEF DESCRIPTION OF THE DRAWINGS

Embodiments of the disclosure are described with reference to the appended drawings, in which:

FIG. 3 is a chart presenting numerous architectures of embodiments of the surgical tool and a handle assembly and frame assembly thereof;

DETAILED DESCRIPTION

Figure 1:
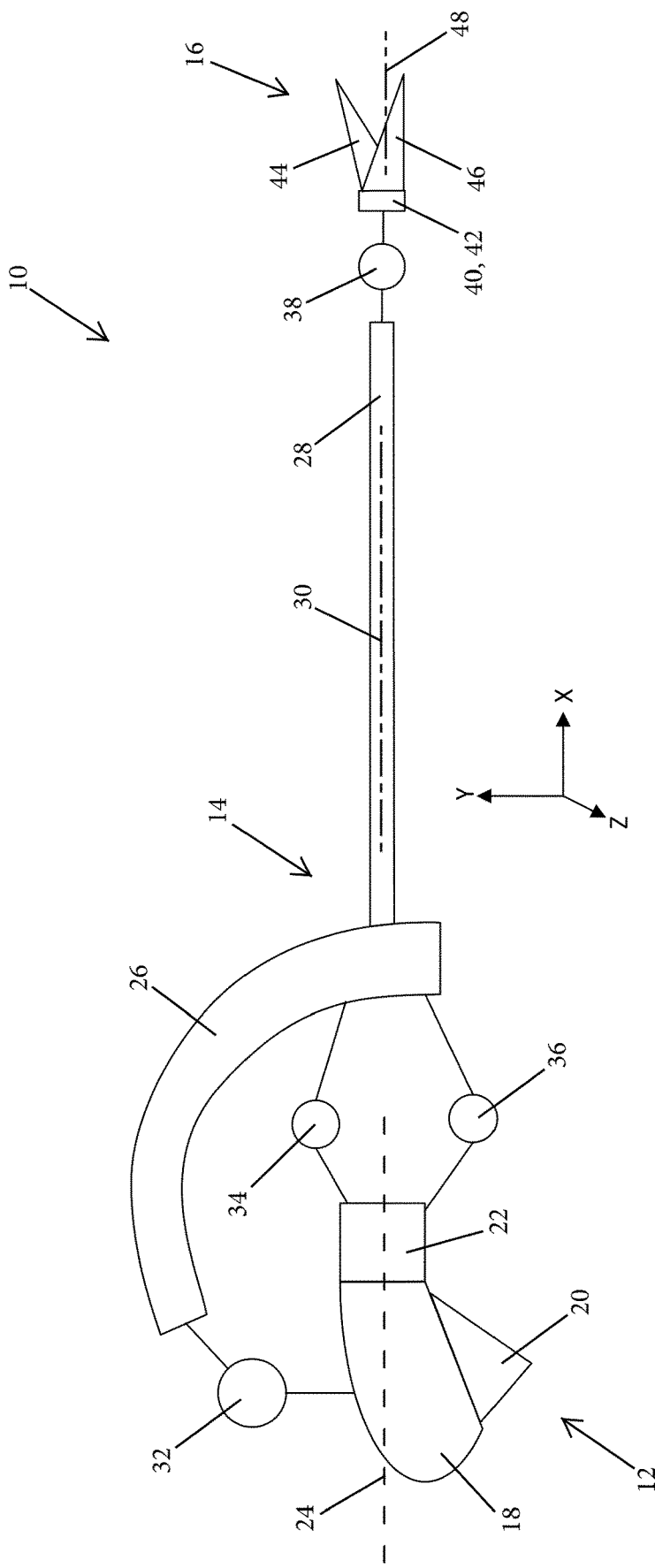
FIG. 1 is a schematic view of an embodiment of a surgical tool.

Multiple embodiments of surgical tools and assemblies are depicted in the figures and detailed in this description. Definitions of certain terms are presented prior to particular figure references in this description:

1.1 Body—Body is a discrete continuous component that can be used as structural components to form an assembly or sub-assembly. The displacement/motion state of a body can be completely defined with respect to a reference ground by six degrees of freedom (DoF). A body can be part of an assembly, where the assembly may include multiple bodies that are inter-connected by joints. Generally, a body may be rigid (i.e., with no compliance) or may be compliant. One or more discrete bodies may be connected together via a rigid joint. These bodies together are still termed as a body as there are no single or multi degree of freedom joints between these bodies. In certain scenarios, this body may be produced out of a single/monolithic structure and therefore, be only a single body. In certain scenarios, a body may be compliant (i.e., not rigid) but still discrete and continuous. In any case, the body may be monolithic or assembled using rigid joints. The body may be of homogenous material composition or heterogenous material composition.

1.2 Mechanism/Joint/Connector—In general, there may be a certain equivalence between the terms "mechanism" and "joint." A "joint" may be alternatively referred to as a "connector" or a "constraint." All of these can be viewed as allowing certain motion(s) along certain degree(s) of freedom between two bodies and constraining the remaining motions. A mechanism generally comprises multiple joints and bodies. Typically, a joint may be of simpler construction, while a mechanism may be more complex as it can comprise multiple joints. A joint refers to a mechanical connection that allows motions as opposed to a fixed joint (e.g., welded, bolted, screwed, or glued jointly). In the latter case, fixed joint, two bodies are fused with each other and are considered one and the same in the kinematic sense (because there is no relative motion allowed or there are no relative degrees of freedom between the two). The term "fixed joint" may be used herein to refer to this kind of joint between two bodies. When reference to the term "joint" is made, it means a connection that allows at least some motions or degrees of freedom, e.g., a pin joint, a pivot joint, a universal joint, a ball and socket joint, etc.

1.3 Degree of Freedom (DoF)—As noted, a joint or mechanism allow certain motions between two bodies and constrains the remaining motions. "Degrees of freedom" is a technical term to capture or convey these "motions." In total, there are six independent motions and therefore degrees of freedom possible between two rigid bodies when there is no joint between them: three translations and three rotations. A joint will allow anywhere between zero and six DoFs between the two bodies. For the case when the joint allows zero DoFs, this effectively becomes a "fixed joint," as described above, where the two bodies are rigidly fused or connected to each other. In this case, from a kinematic sense, the two bodies are one and the same. For the case when the joint allows six DoFs, this effectively means that the joint does not constrain any motions between the two bodies. In other words, the motions of the two bodies is entirely independent of each other. A joint for the purpose this application may allow one, or two, or three, or four, or five DoF between two rigid bodies. If it allows one DoF, then the remaining five possible motions are constrained by the joint. If it allows two DoF, then the remaining four possible motions are constrained by the joint, and so on.

1.4 Degree of Constraint (DoC)—"Degree of constraint" refers to directions along which relative motion is constrained between two bodies. Since relative motion is constrained, these are directions along which motion and loads (i.e., forces or moments) can be transmitted from one body to the other body. Since the joint does not allow relative motion between the two bodies in the DoC direction, if one body moves in the DoC direction, it drives along with it the other body along that direction. In other words, motions are transmitted from one rigid body to another in the DoC directions. Consequently, loads are also transmitted from one rigid body to another in the DoC directions, which are sometimes also referred to as the load bearing directions or simply bearing directions. The term "retention" may also be used in the context of a DoC direction. For example, one body may be constrained or equivalently retained with respect to a second body along a certain DoC. This means that relative motion is not allowed between the two bodies in the DoC direction, or equivalently the direction of constraint, or equivalently the direction of retention. Retention of all six DoFs means the same thing as having six DoCs between two bodies.

1.5 Local Ground—In the context of an assembly of bodies connected by joints (e.g., a multi-body system, a mechanism), one or more bodies may be referred to as the "reference" or "ground" or "local ground." The body referred to as the local ground is not necessarily an absolute ground (i.e., attached or bolted to the actual ground). Rather, the body that is selected as a local ground simply serves as a mechanical reference with respect to which the motions of all other bodies are described or investigated.

1.6 Axis and Direction—Axis refers to a specific line in space. A body may rotate with respect to (w.r.t.) another body about a certain axis. Alternatively, a body may translate w.r.t. another body in a certain direction. A direction is not defined by a particular axis and is instead commonly defined by multiple parallel axes. Thus, x-axis is a specific axis defined in space, while X direction refers to the direction of the x-axis or any other axis that is parallel to the x-axis. Multiple different but parallel axes can have the same X direction. Direction only has an orientation and not a location in space. In at least some embodiments, and with particular reference to FIG. 1, a coordinate system is presented with the x-axis coinciding with an axis of a tool shaft (introduced below) of the surgical tool, the y-axis oriented relative thereto, and the z-axis coming out of the paper.

1.7 Serial Kinematic Joint/Mechanism—The term "kinematics" may refer to the geometric study and description of motion of bodies relative to other bodies. A serial kinematic joint, or serial kinematic mechanism, consists of bodies connected via a serial chain of connectors, joints, or mechanisms. If one traces or scribbles a line from one body to another in a serial kinematic joint/mechanism, there exists only one mechanical path (or line) of motion transmission. In a somewhat simplistic example of a serial kinematic joint/mechanism, a first body and a second body are connected to each other via four connectors and three intermediate bodies. The first body and second body may be considered rigid, and the intermediate bodies may be considered rigid for practical purposes. The connectors may be simple or complex joints that may allow certain motions while constrain other motions. The connectors and intermediate bodies may span in what is effectively a single line and mechanical path between the first and second bodies.

1.8 Parallel Kinematic Joint/Mechanism—In a somewhat simplistic example of a parallel kinematic mechanism, the first body is connected to the second body via multiple independent chains and lines of intermediate bodies. Each such chain represents a mechanical path of motion transmission. If one traces possible lines from the first body to the second body, there is more than one mechanical path, which makes this a parallel design. The connection paths are not parallel in a geometric sense (e.g., two straight lines being parallel such as the opposing sides of a rectangle), but parallel in the kinematic sense, which implies multiple (more than one), independent, non-overlapping chains or paths between the first body and second body. The connectors here are simple or complex joints that allow certain motions and constrain other motions. For convenience, the term joint and connector may be used interchangeably.

1.9 Virtual Center of Rotation—When provided in an embodiment, a virtual center of rotation, (also referred to as "virtual center"), refers to a center of rotation where two or more axis of rotation coincide or intersect. For example, two axes of rotation can intersect. An axis of rotation of a first rotational direction, such as a pitch axis, and an axis of rotation of a second rotational direction, such as a yaw axis, intersect at a virtual center of rotation. The virtual center may be located in a vacant space devoid of any other components of a parallel kinematic mechanism, for example.

1.10 User Interface—When provided in an embodiment, a user interface refers to the input interface that a user interacts with to provide input to a machine or instrument or mechanism with the objective of producing some change or outcome in the machine or instrument or mechanism. User interface is often an ergonomic feature on a body, which is part of an instrument, that is triggered or actuated by the user, e.g., a knob on a car dashboard can be rotated by a user to increase/decrease speakers' sound volume. Here, the knob and, specifically, the knurled outer circumference (feature) of the knob is the user interface.

1.11 Transmission Member—When provided in an embodiment, a transmission member is a rigid or compliant body that transmits motions from one body to another body. A transmission member may be a compliant wire, cable, cable assembly, flexible shaft, etc.

1.12 Handle Body—When provided in an embodiment, a handle body refers to a body in the handle assembly which is considered as a local ground while describing the handle assembly and associated mechanisms. When provided, the handle body is held by the user while other bodies within handle assembly may be put in motion with respect to the handle body via the user interface.

1.13 Handle Assembly—When provided in an embodiment, a handle Assembly is a term used for an assembly that, in some embodiments, at least consists of the handle body and user interface.

1.14 Tool Frame—When provided in an embodiment, the tool frame refers to a structural body that may be part of a tool apparatus or surgical tool. In certain tool apparatuses, it may be connected to handle assembly and/or an elongated tool shaft. Terms namely "tool frame" and "frame" may be used interchangeably throughout the document.

1.15 Tool Shaft—When provided in an embodiment, a tool shaft is generally a rigid extension of the frame, at its proximal end, which is a slender and elongated member, commonly a cylinder, that houses the end-effector assembly at its distal end. The tool shaft may simply be referred to as the shaft. The axis of the tool shaft may be referred to as axis 3 or Tool Shaft Roll Axis or Tool Shaft Axis throughout the description.

1.16 End-Effector Assembly—When provided in an embodiment, the end-effector (EE) assembly may be referred to as the EE assembly. In some embodiments, the EE assembly may exist at the distal end of the tool shaft. An EE assembly may contain one or more jaws (or EE jaws). There can be two types of EE assembly. The first type of EE assembly consists of two EE jaws, namely a moving jaw and a fixed jaw. There may also exist an EE frame that acts a local reference ground for the moving jaw and any other moving body within the EE assembly. In such an assembly, the moving jaw moves relative to the EE frame by rotating about a pivot pin. This motion of the moving jaw with respect to the EE frame is termed as jaw closure motion. The fixed jaw may also be coupled to EE Frame such that it is a rigid extension of the EE Frame. The EE frame may be further coupled to the shaft via an output articulation joint.

When an instrument incorporates an output articulation joint, the EE frame rotates about an Axis 2 while the tool shaft rotates about Axis 3. When there is no input at the articulation input joint, Axis 2 and Axis 3 are oriented parallel to the X-axis. In cases where there is an input at the articulation input joint, Axis 2 will be deviate from a parallel orientation to the x-axis by rotating varying amounts about the y-axis and z-axis. The EE assembly rotation about the y-axis may also be referred to as EE yaw, whereas rotation about the z-axis may be referred to as EE pitch.

1.17 Roll Transmission Member—When provided in an embodiment, this transmission member helps transmit rotation of rotation input or dial w.r.t. the handle body to produce EE roll motion.

1.18 Articulation Transmission Member—When provided in an embodiment, the articulation transmission member is a transmission member, or connector, that transmits articulation (pitch and yaw motion) from an articulation input joint to an articulation output joint.

1.19 Jaw Closure Transmission Assembly—When provided in an embodiment, a jaw closure transmission assembly refers to bodies, joints, mechanisms and/or jaw closure transmission member(s) that exist between the handle assembly and the EE assembly and facilitate jaw closure motion. In an example, the body within the handle assembly that produces output motion (e.g., a shuttle) is coupled to the proximal body that is part of the jaw closure transmission assembly. Similarly, the moving jaw within the EE assembly is coupled to the distal most body that is part of the jaw closure transmission assembly. Terms "jaw closure transmission assembly" and "jaw actuation transmission assembly" may be used interchangeably throughout the description.

1.20 EE Roll Transmission Assembly—When provided in an embodiment, the EE roll transmission assembly refers to bodies, joints, mechanisms and/or roll transmission member(s) that may exist between the handle assembly and the EE assembly and facilitate EE roll motion. In an example, body within the handle assembly that produces output motion (e.g., the shuttle) is coupled to the proximal body that is part of the roll transmission assembly. Similarly, components within the EE assembly (e.g., an EE frame) is coupled to the distal most body that is part of the roll transmission assembly.

2. Surgical Tool and Assembly, Functional Attributes, and User Experience

Figure 17:
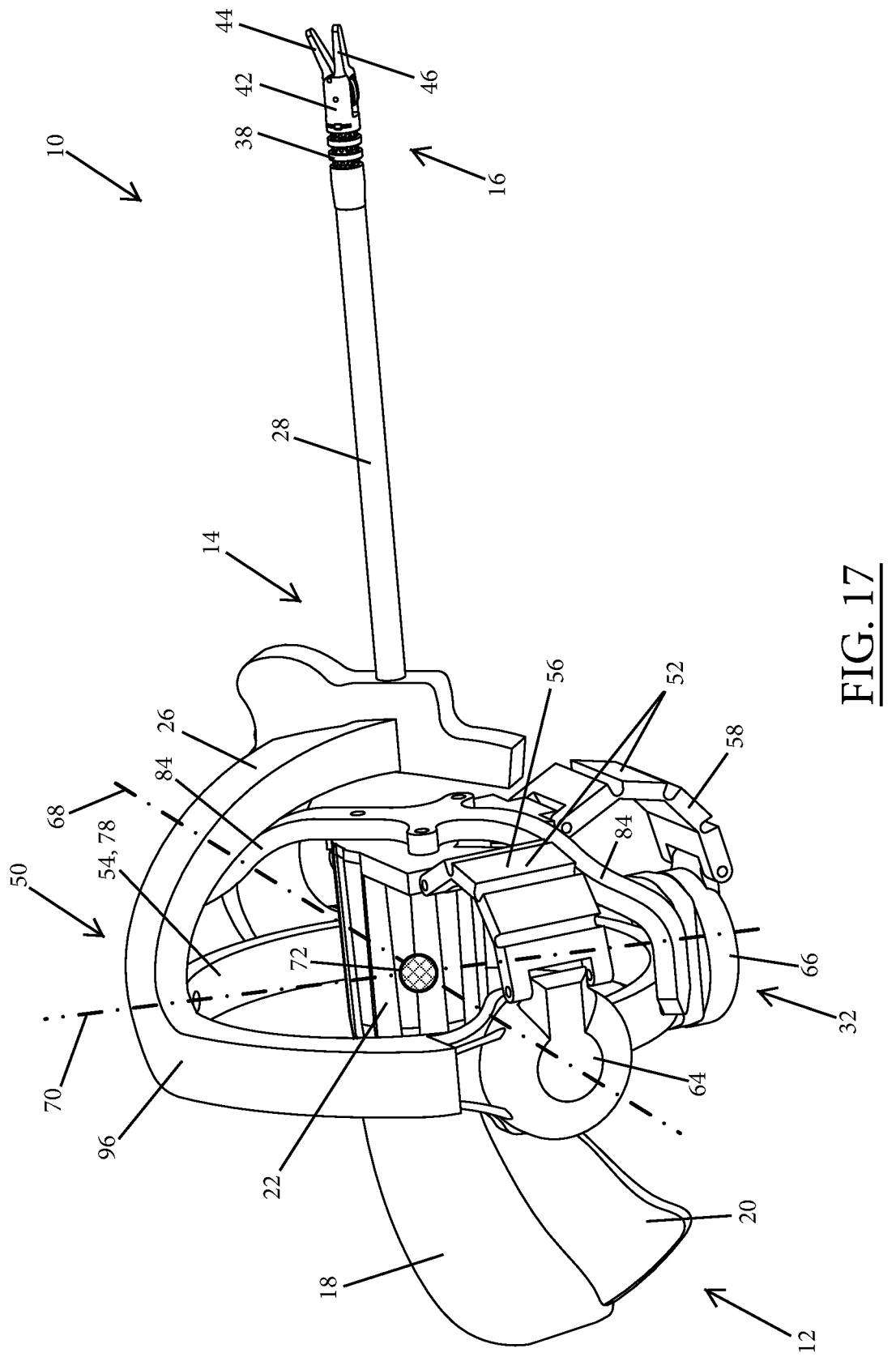
FIG. 17 is a perspective view of another embodiment of the first architecture (I) of the handle assembly and frame assembly of the surgical tool assembly.
Figure 18:
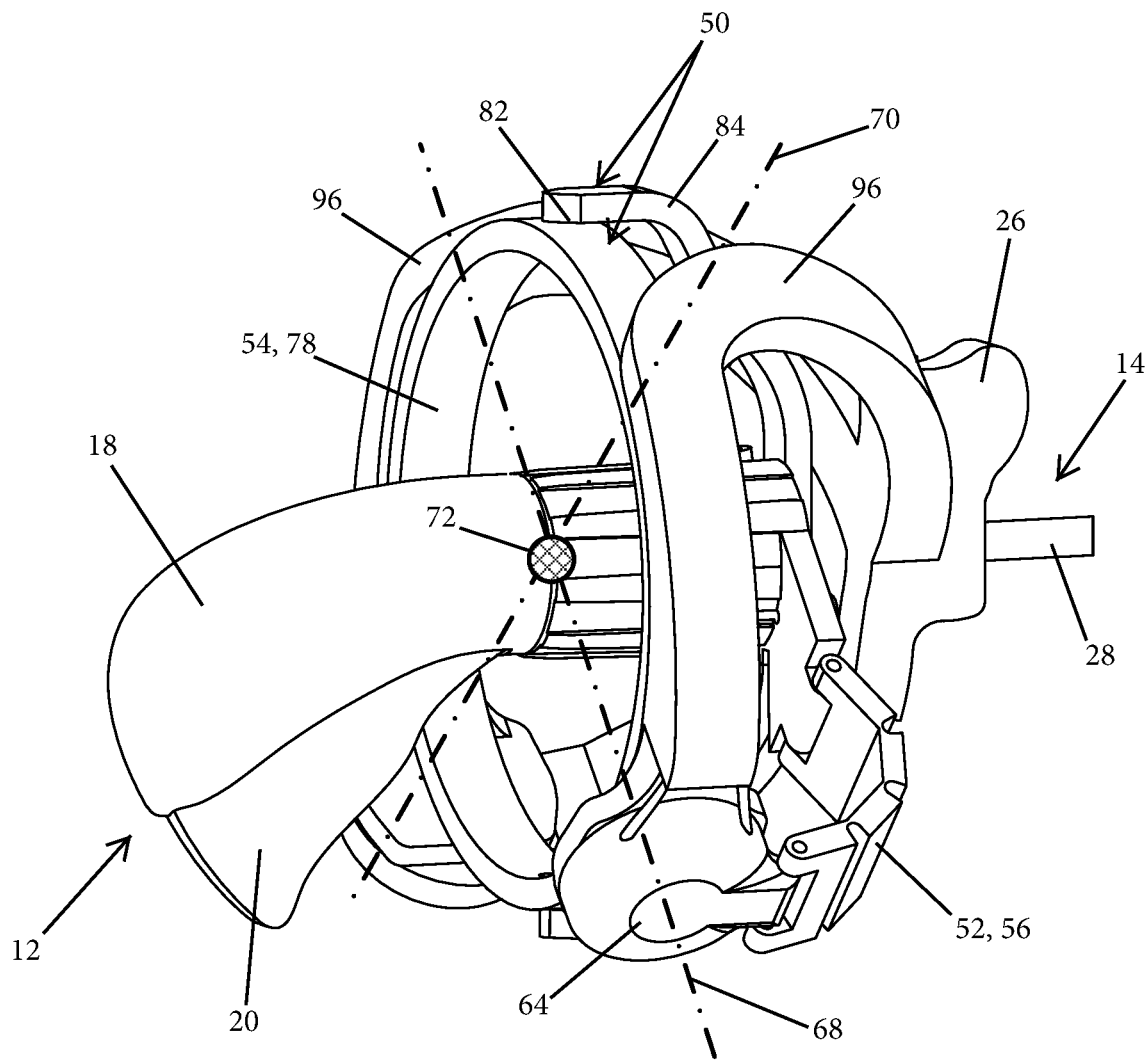
FIG. 18 is another perspective view of the surgical tool assembly of FIG. 17.
Figure 19:
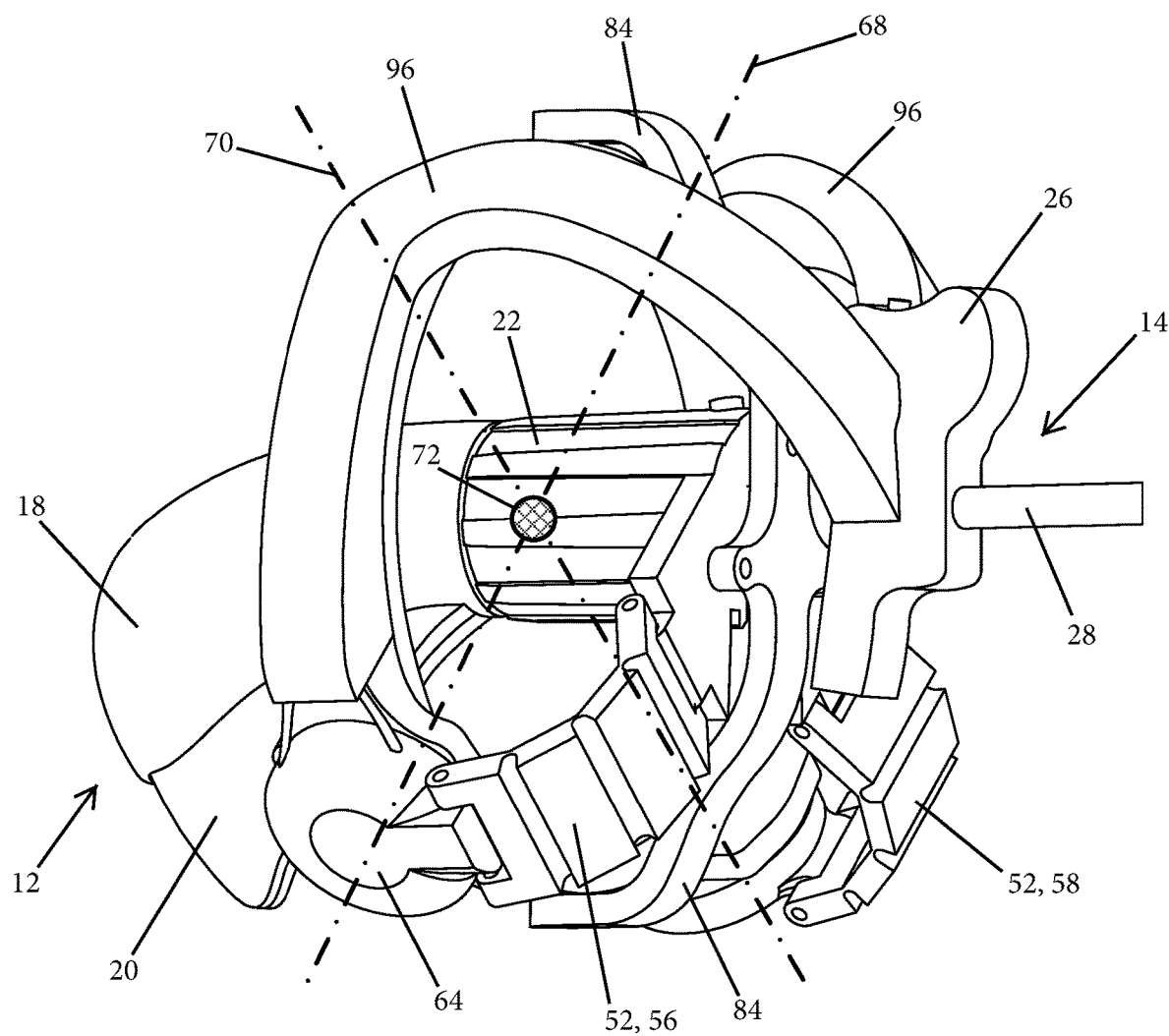
FIG. 19 is another perspective view of the surgical tool assembly of FIG. 17.
Figure 20:
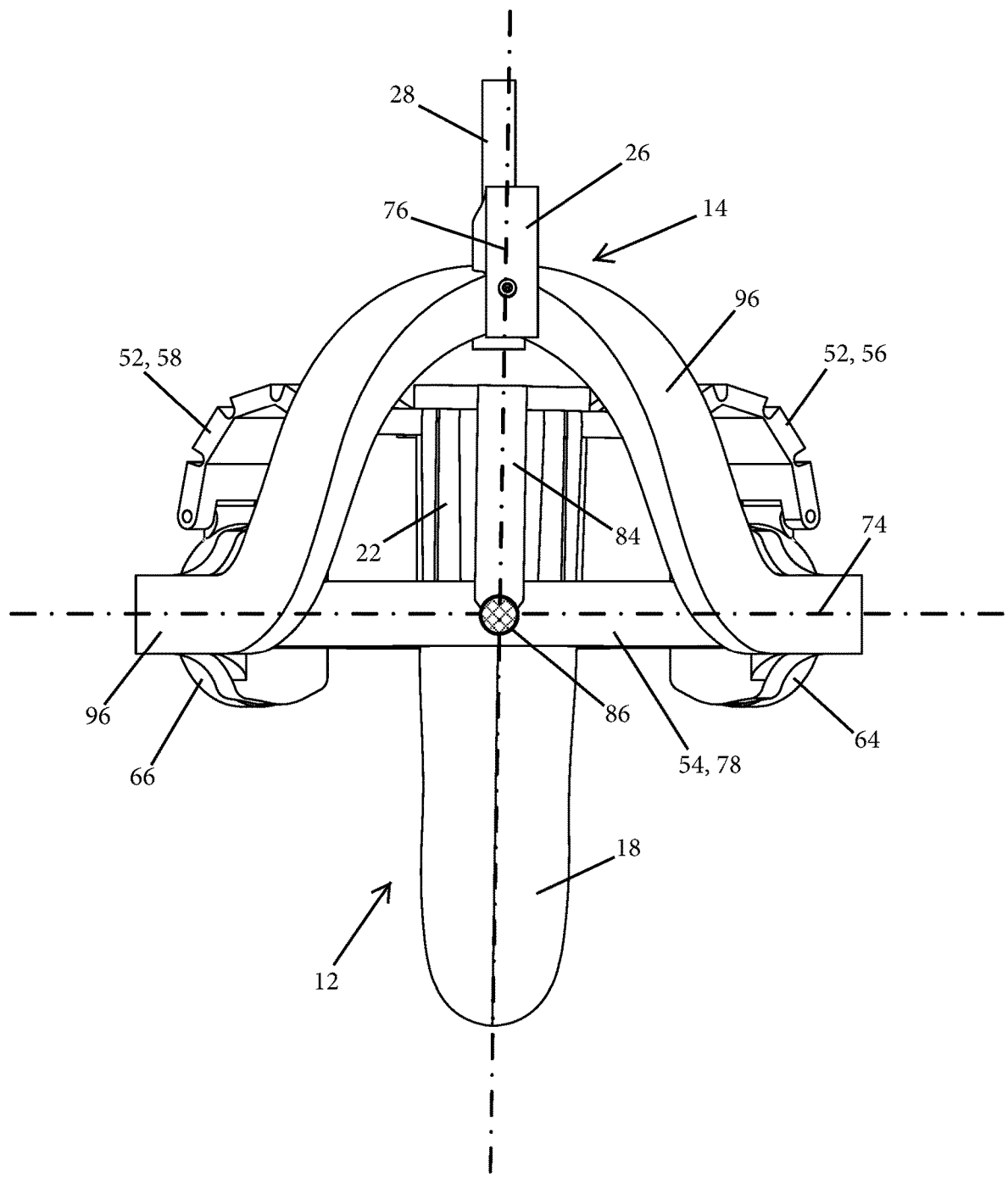
FIG. 20 is a top view of the surgical tool assembly of FIG. 17.
Figure 21:
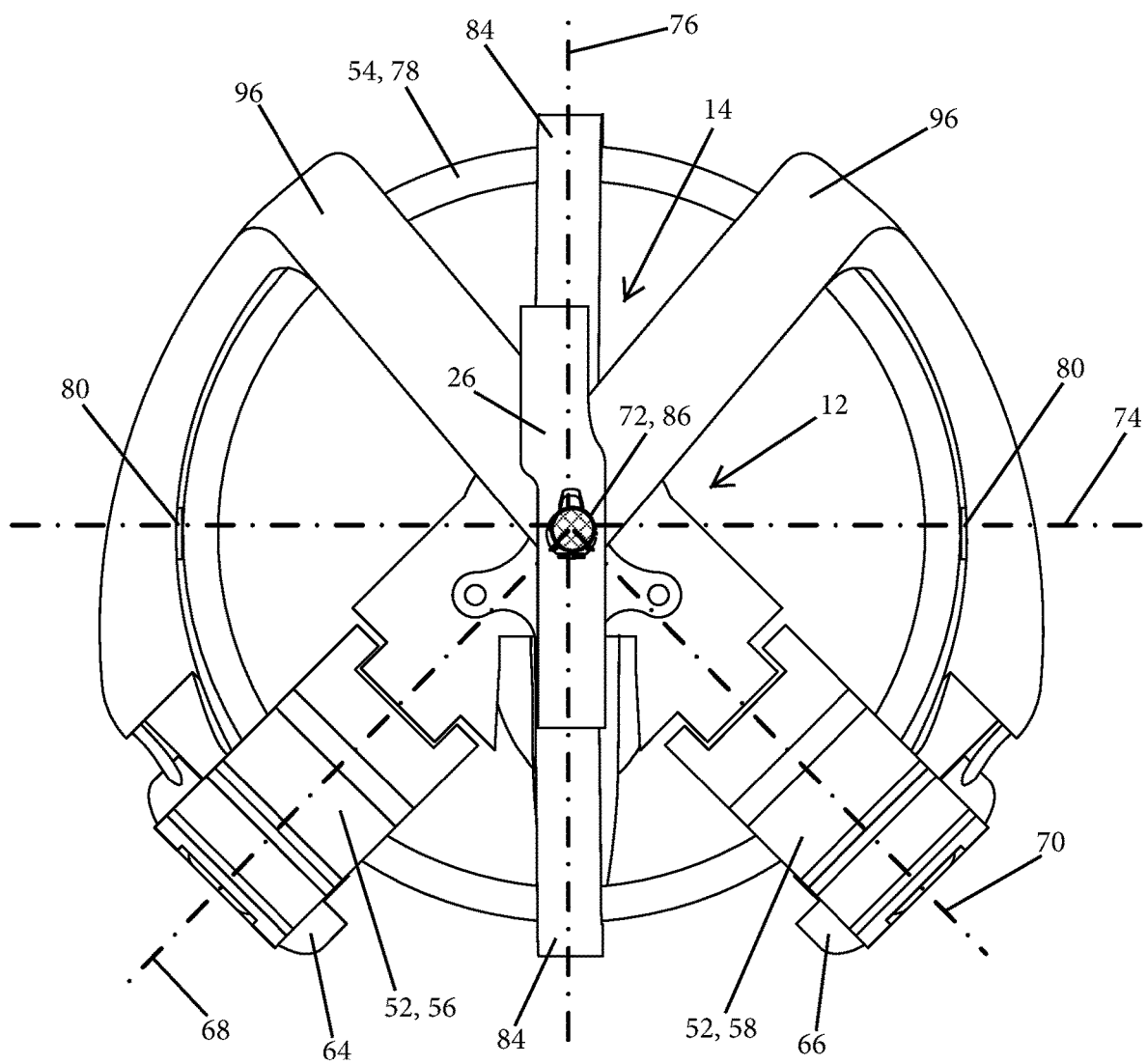
FIG. 21 is a front view of the surgical tool assembly of FIG. 17.
Figure 22:
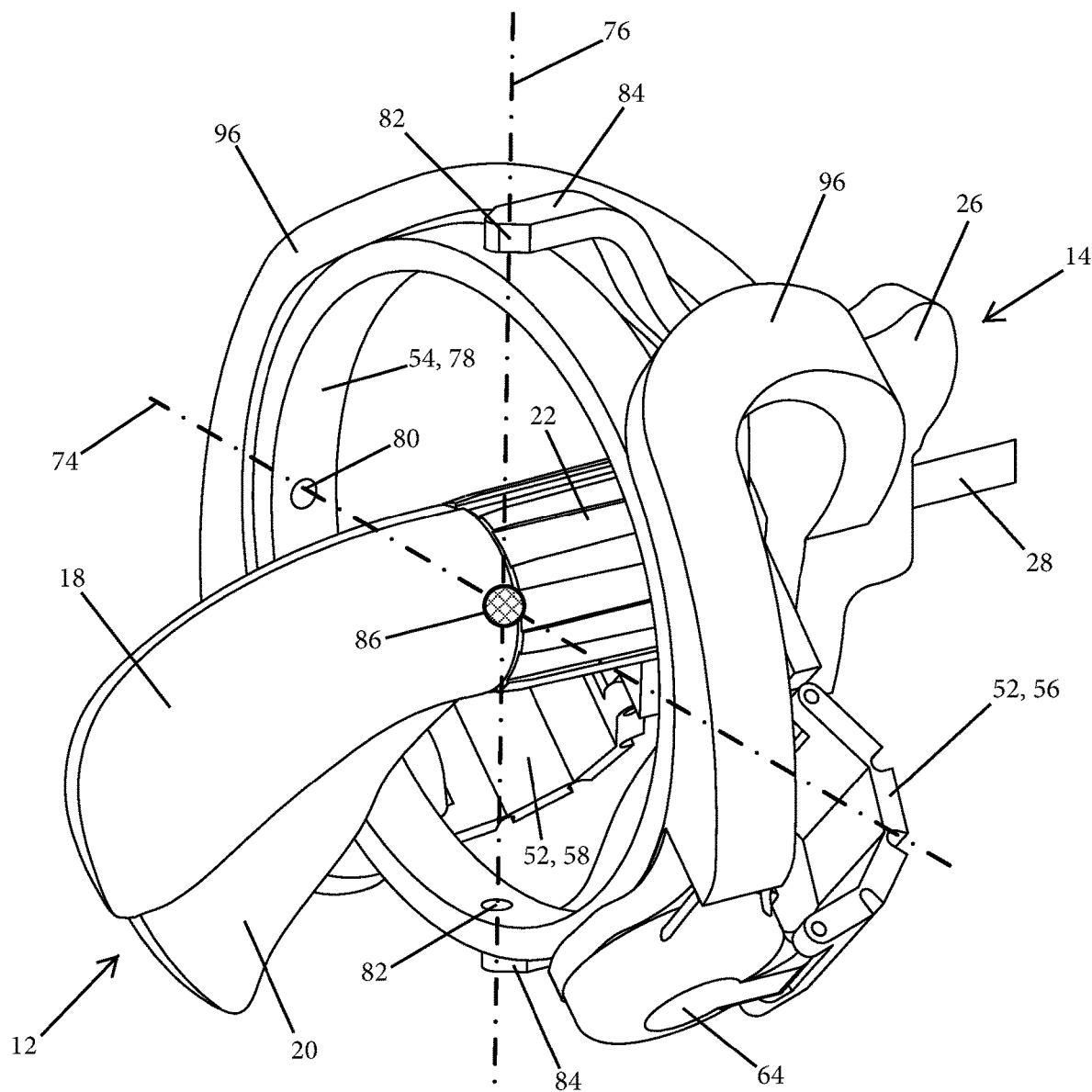
FIG. 22 is another perspective view of the surgical tool assembly of FIG. 17.
Figure 23:
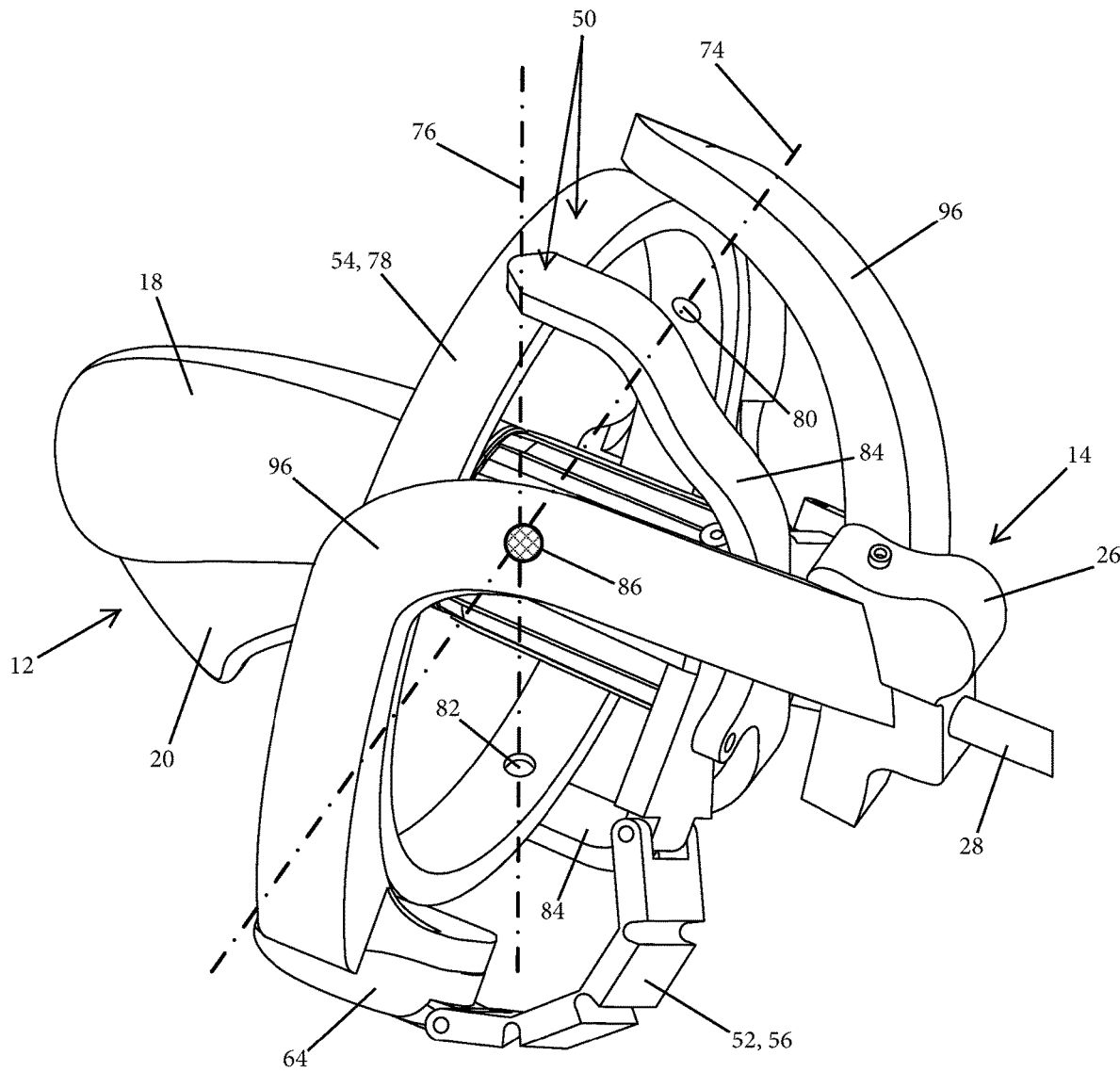
FIG. 23 is another perspective view of the surgical tool assembly of FIG. 17.

In general, a surgical tool 10 can be employed for use in minimally invasive surgical (MIS) procedures, and can be a handheld instrument. The surgical tool 10 may also be referred to as a tool apparatus; or, in the case of it being handheld, may be referred to as a handheld tool apparatus. The surgical tool 10 may have various designs, constructions, and components in different embodiments, which may be dictated in part or more on the intended application and ultimate use of the surgical tool 10. FIG. 1 presents a schematic representation of an embodiment of the surgical tool 10. The figure is intended to provide an introduction of some of the more primary components of the surgical tool 10, per an embodiment, as well as an overall arrangement of those components relative to one another (FIG. 17 also provides a depiction of many of the components). In this embodiment, the surgical tool 10 has a handle assembly 12, a frame assembly 14, and an end-effector (EE) assembly 16. The handle assembly 12, according to this embodiment, includes a handle body 18, a closure input 20, and a dial 22. The handle assembly 12 establishes a handle axis 24 (also referred to as Axis 1 in this description) that is arranged longitudinally and centrally therethrough, per this embodiment. The frame assembly 14, according to this embodiment, includes a frame 26 and a tool shaft, or just shaft 28. The shaft 28 establishes a shaft axis or x-axis 30 (also referred to as Axis 3 in this description). An articulation input joint (AIJ) 32 is situated between the handle assembly 12 and the frame assembly 14. A roll actuation joint 34 and a closure actuation joint 36 extend from the handle assembly 12. An output articulation joint 38 is situated between the shaft 26 and the EE assembly 16.

Lastly, the EE assembly 16, according to this embodiment, includes an EE base 40, an EE frame 42, a moving jaw 44, and a fixed jaw 46. The EE assembly 16 establishes an EE axis 48 (also referred to as Axis 2 in this description) that is arranged longitudinally therethrough, per this embodiment. Various surgical tool assemblies can include one or more of these components, or a combination of the components.

The tool apparatus, or surgical tool 10, hence includes the handle assembly 12, the frame assembly 14, and the EE assembly 16 that are related via a plurality of joints and connectors. Collectively, the collection of bodies, joints, and connectors facilitate the translation of useful user input motions at the handle assembly 12 into useful motions of the EE Assembly 16 distally located with respect thereto. Intermediate to the handle assembly 12 and EE assembly 16 is located the frame assembly 14. The system facilitates the transmission of seven distinct motions from the handle assembly 12 to the EE assembly 16 via the frame assembly 14 (i.e., three translations, three rotations, and jaw open-close). Due to the independence of different motion transfer paths, the system is configured such that it provides a degree of device usability that is higher than past MIS devices. In at least some embodiments, the surgical tool 10 lacks electrical components among the handle assembly 12, frame assembly 14, and EE assembly 16, and can hence be considered a purely mechanical device and assembly.

The system is comprised of the three assemblies: the handle assembly 12 which receives the user inputs, the frame assembly 14 which includes the rigidly connected shaft 28, and the EE assembly 16. Between each assembly are a plurality of joints and intermediate bodies configured to receive and map motions between the bodies. The joints and intermediate bodies may simply be referred to collectively as a connection. One focus of this application relates to the configuration of connections that reside between the handle assembly 12 and the frame assembly 14 and their collective impact on EE assembly motions.

The connections between the handle and frame assemblies 12, 14 that are used for positioning and orientation of the shaft 28 and EE assembly 16 may constitute and make-up the articulation input joint 32 and may constitute and make-up a grounding joint 50 (sometimes referred to as an axial grounding joint (AGJ) 50). A purpose of the AIJ 32 is to translate two rotational degrees of freedom of the handle assembly 12 (pitch and yaw) to the EE Assembly 16. Additionally, the AIJ 32 may passively translate the third rotational degree of freedom, roll about the x-axis, from the handle assembly 12 to the EE assembly 16 as well. Further, it may be referenced that the roll motions are translated via the roll actuation joint 34. Although the roll actuation joint 34 may be independent in some device architectures, the roll motions may be generally translated and integral to the AIJ 32. In an embodiment, the pair of intermediate bodies that facilitate the transfer of motions and that are located between the frame assembly 14 and handle assembly 12 may be flex strips 52. Each flex strip 52 is connected to the handle and frame assemblies 12, 14 via a hinge joint. The flex strips 52 may be a flexible body, or mechanism, which provides one DoF between the oppositely spaced hinge joints.

A purpose of the AGJ 50 is to translate three translational rigid body DoFs (motions in x-axis, y-axis, and z-axis directions) from the handle assembly 12 to the EE assembly 16 via the frame assembly 14 and translate one rotational DoF (roll). In other words, the AGJ 50 constrains three rigid body DoFs (motions in x-axis, y-axis, and z-axis directions) between the handle assembly 12 and the frame assembly 14 with respect to each other, and constrains one rotational DoF (roll) between the handle assembly 12 and the frame assembly 14 with respect to each other. But the AGJ 50 does not constrain the pitch rotational DoF between the handle assembly 12 and the frame assembly 14 with respect to each other, and does not constrain the yaw rotational DoF between the handle assembly 12 and the frame assembly 14 with respect to each other.

Figure 4:
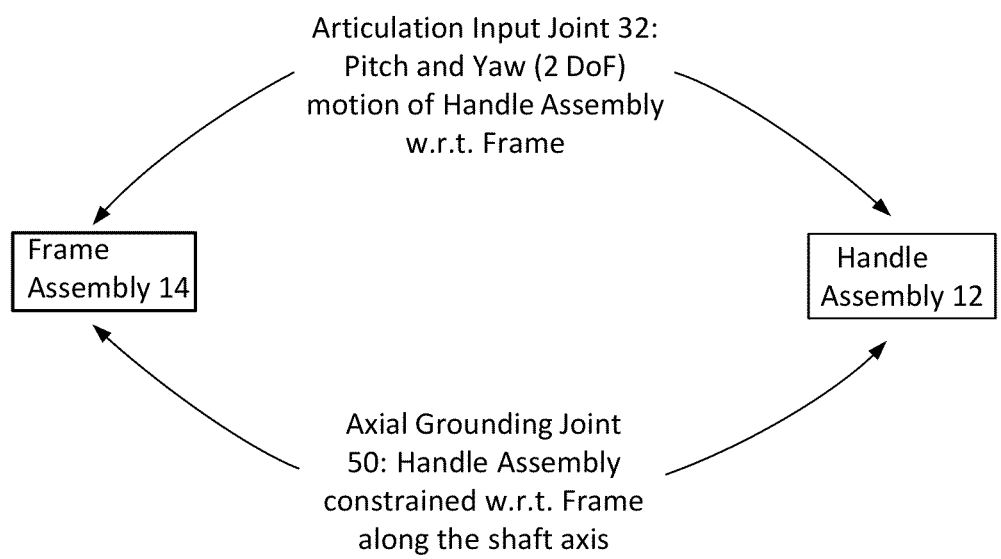
FIG. 4 is a schematic diagram demonstrating a parallel kinematic relationship and arrangement of an articulation input joint and an axial grounding joint according to an embodiment of the surgical tool.

Enhanced usability of the surgical tool 10, as compared to past MIS instruments and according to at least one embodiment, is facilitated by parallel configuration of the AIJ 32 and the AGJ 50. FIG. 4 is a schematic diagram demonstrating the parallel configuration of the AIJ 32 and the AGJ 50. The AIJ 32 can be structured as a parallel-kinematic (PK) mechanism in certain embodiments whereby the pitch and yaw motions are independently mapped from the handle assembly 12 through the frame assembly 14 to the EE assembly 16. The PK configuration that facilitates mapping of handle assembly 12 motions to the EE assembly 16, via the frame assembly 14, are described in U.S. Pat. No. 8,668,702 which is hereby incorporated herein by reference. The AGJ 50 can be an additional parallel control path, per an embodiment, from the handle assembly 12 to the frame assembly 14. The connection allows for mapping of rigid body motions from the handle assembly 12 to be translated directly to the frame assembly 14 and, in-turn, to the EE assembly 16. The parallel nature of the AIJ 32 and AGJ 50 means that articulation input motions at the AIJ 32 may be mapped to the end effector assembly 16 independent of rigid body translational motions through the AGJ 50.

To frame usability benefits, it may be assumed that the use case for the surgical tool 10 involves, at a minimum, a user (typically a surgeon) and a trocar (i.e., device that allows insertion of an instrument into a patient's body during a surgical operation; an access portal for the instrument; a grounded device providing two rigid body translational DoC to the instrument shaft; restricts tool shaft motion in y-direction and z-direction). The user grasps the handle body 18 while positioning the surgical tool 10 such that the shaft 28 of the frame assembly 14 extends through the trocar. The trocar provides an effective single point, simple support for the shaft 28 to constrain the motions. When viewing the location of the trocar simple support as local ground, the trocar does not provide any rotational constraint in any of the three rotational DoF for the shaft 28 (rotation about y-axis, rotation about z-axis, and roll about the shaft x-axis). The trocar also does not constrain translation motion along the shaft 28; thus, allowing sliding motion in x-direction. The limitations of motion for the surgical tool 10 may be dictated only by the inherent geometrical constraints of the system.

When grasping the handle assembly 12, the user controls the position and orientation of the EE assembly 16 through input motions of the handle assembly 12. When a user grasps the handle assembly 12 and provides a yaw motion input, a proportional yaw motion output of the EE assembly 16 will be produced. Likewise, pitch motion input at the handle assembly 12 translates to a pitch motion at the EE assembly 16. The yaw motion input and the pitch motion input are via the AIJ 32, per at least some embodiments. When the user moves the handle assembly 12 in the X-direction (parallel to the X-axis), the EE assembly 16 moves accordingly along the shaft axis 30 through the trocar and as if it were rigidly connected to the handle assembly 12. For handle assembly 12 motions in the direction of the positive Z-direction (+Z) or positive Y-direction (+Y), the EE assembly 16 translates inversely, and proportional, due to the DoC of the trocar pivot. In other words, handle assembly 12 motion in a direction parallel with the +Y will result in proportional motion of the EE assembly 16 in a negative Y-direction (−Y); this holds true for handle assembly 12 motions in the Z-direction. This may be referred to as the fulcrum effect. These movements in the X-, Y-, and Z-directions are via the AGJ 50, per at least some embodiments. The resultant input control system provided to the user allows the user to precisely and predictably control the position and orientation of the shaft 28.

As stated, each of the independent input motions at the handle assembly 12 described may be orchestrated without impact to other unintended motions of the EE assembly 16 relative to the shaft 28 local ground. The orientation of the EE assembly 16 is controlled through pitch and yaw input motions at the handle assembly 12 (change in rotational orientation of Axis 1). When the pitch and yaw orientation of the EE assembly 16 change, Axis 2 shifts and is no longer parallel with Axis 3. Yaw input motion at the handle assembly 12 will produce proportional yaw output motion of the EE assembly 16. The EE assembly 16 motion occurs without effect to shaft 28 position or orientation relative to the trocar nor does it impact the pitch orientation of the EE assembly 16. Likewise, pitch input at the handle assembly 12 will only produce EE assembly 16 pitch motion. The independence of each relationship allows for a user to precisely and predictably control the orientation of the EE assembly 16 relative to the shaft 28.

According to at least some embodiments, and with general reference now to FIGS. 9-16, the construction of the AIJ 32 includes the handle assembly 12 and the frame assembly 14 joined by a pair of intermediate bodies 54: a first intermediate body 56 and a second intermediate body 58. The intermediate bodies 54 take different forms in different embodiments, and may be in the form of flexible connector members or the flex strips 52. The intermediate bodies 54 are orthogonally oriented relative to one another and mounted directly to the handle assembly 12 via first pin joints 60. The intermediate bodies 54 are joined to the frame assembly 14 via second pin joints 62. The second pin joints 62 are not rigidly attached to the frame 26, and rather are mounted to a first pulley 64 and a second pulley 66 that are allowed one rotational DoF. The first and second pulleys 64, 66 are oriented such that their axes of rotation are orthogonally positioned to each other and lie in the Y-Z plane (plane oriented perpendicular to the X-axis). The intersection of a corresponding first pulley axis 68 and a second pulley axis 70 may be referred to as a virtual center 72 of the AIJ 32 (VC-AIJ), or a first virtual center 72. The resultant AIJ configuration allows for pitch and yaw motions of the handle assembly 12 to directly, and via the intermediate bodies 54 or flex strips 52, result in equivalent rotational motions of the first and second pulleys 64, 66 pivoting on the frame assembly 14. The pulley motions may in-turn, be connected to cable systems and produce work that is used to control the position of the EE assembly 16 or any other type of controllable mechanism. Additionally, the AIJ 32 provides the roll DoC between the handle assembly 12 and frame assembly 14, thus allowing roll input motions at the handle assembly 12 to translate to equivalent roll output motions at the shaft 28 and EE assembly 16. The collective impact of the AIJ components is that the AIJ 32 provides pitch and yaw DoC between the handle assembly 12 and first and second pulleys 64, 66 and roll DoC between the handle assembly 12 and frame assembly 14. The AIJ 32 does not create X-direction, Y-direction, or Z-direction DoC between the handle assembly 12 and adjacent bodies. Further, a pitch axis 74 and a yaw axis 76 are established via the pitch and yaw motions effected by the AIJ 32. And, at least in this embodiment, a third intermediate body 78 in the form of a rotation or deviation ring is provided. The AIJ 32 may be established, per an embodiment, by the collection of the first intermediate body 56, the second intermediate body 58, the first pulley 64, the second pulley 66, the first pulley axis 68, and the second pulley axis 70.

According to at least some embodiments, and still with general reference to FIGS. 9-16, the AGJ 50 is constituted by a gimbal structure that provides for a flexibly grounded attachment of the handle assembly 12 to the frame assembly 14. The structure is constructed in a manner so that it does not impede the handle assembly 12 motions needed for AIJ 32 inputs, while providing the grounding constraints between the bodies. In other words, the AGJ 50 is configured in such a manner that it provides grounded attachments between the handle assembly 12 and the frame assembly 14 to provide direct positional control of a proximal point on the frame assembly 14 located at the center of the gimbal. The AGJ 50, per at least some embodiments, provides X-direction, Y-direction, and Z-direction DoCs. The movement of the frame 26 (X-direction, Y-direction, Z-direction) via the handle assembly 12 at the center of the gimbal is accomplished independent of any pitch or yaw motions influence of the handle assembly 12. The AGJ 50 may be established, per an embodiment, by the collection of the pitch axis 74, the yaw axis 76, and the third intermediate body 78.

The handle assembly 12 is connected to the third intermediate body 78, or the deviation ring, that contains two sets of pin joints orthogonally oriented around its circumference: a third set of pin joints 80 and a fourth set of pin joints 82. The third set of pin joints 80 is a pitch DoF joint, while the fourth set of pin joints 82 is a yaw DoF joint. The pitch DoF joint 80 is connected to the handle assembly 12 or to unitary extension arms 84 of the handle assembly 12, while the yaw DoF joint 82 is connected to the frame assembly 14. The extension arms 84 can themselves be rigid bodies. In at least some embodiments, the extensions arms 84 can be a constituent part of the handle assembly 12 or can constitute intermediate bodies of the surgical tool 10. The architecture of the handle assembly 12, when connected to the deviation ring pitch DoF joint 80, positions the handle axis 24, at the center of the deviation ring 78. The deviation ring yaw DoF joint 82 at the frame assembly 14 may be split into an additional intermediate member and two joints that allow for a roll DoF (a bearing or rotationally sliding member); however, this is not necessary for function.

The center point defined by the deviation ring 78 is at an intersection of the two axes created by the pitch DoF joint 80 and the yaw DoF joint 82—namely, at the intersection of the pitch axis 74 and the yaw axis 76. The center of rotation may also be referred to as a virtual center 86 of the AGJ 50 (VC-AGJ), or a second virtual center 86. The VC-AGJ 86 is located at a point that also intersects the shaft axis 30. In other embodiments the VC-AGJ 86 may be located at point that does not intersect the shaft axis 30. It is helpful to view the VC-AGJ 86 as the point whereby the user controls the position of the proximal end of the frame 26. It is from that point that the user may raise or lower the surgical tool 10 (Y-direction motion), move the surgical tool 10 from side-to-side (Z-direction motion), and drive or retract the surgical tool 10 from the trocar along the shaft axis 30 (X-direction motion).

According to at least some embodiments, device usability is influenced by the relative locations of the VC-AIJ 72, VC-AGJ 86, the handle axis 24 (Axis 1), and the shaft axis 30 (Axis 3). Furthermore, usability is influenced by the positioning of the user interfaces that control the influential points. The handheld architecture, per at least some embodiments, incorporates co-location and intersection of these elements. The VC-AIJ 72 and VC-AGJ 86 can exhibit a generally coincident arrangement relative to each other according to at least some embodiments. In this sense, the VC-AIJ 72 and VC-AGJ 86 may simply be referred to as the virtual center. Stated another way, the VC-AIJ 72 and the VC-AGJ 86 may reside at the same and single virtual center. Further, the handle axis 24 and the shaft axis 30 can exhibit a generally intersecting arrangement with the VC-AIJ 72 and with the VC-AGJ 86, per at least some embodiments. That is, the handle axis 24 can intersect the VC-AIJ 72 and can intersect the VC-AGJ 86, and the shaft axis 30 can likewise intersect the VC-AIJ 72 and can intersect the VC-AGJ 86. As used herein, the phrases "generally coincident" and "generally intersect," and their grammatical variations, are intended to account for certain engineering and manufacturing tolerances and slight imprecisions that may arise—and without deviation from the intended functionality and outcome—such that mathematical precision is not implied and, in some instances, is not possible.

Per at least some embodiments, the handle assembly 12 is the control point to effect articulation of the EE assembly 16 via the AIJ 32, the roll position of the frame assembly 14 and the EE assembly 16 via the AIJ 32, and the position of the EE assembly 16 via the virtual center (i.e., VC-AIJ 72 and VC-AGJ 86) and the AGJ 50. In other words, all useful motions of the EE assembly 16 can be controlled through a single user interface element, or touch point—namely the handle assembly 12. When a user grips the handle assembly 12, the user gains control of all useful motions of the surgical tool 10 within the palm of the user's hand. This differs from certain past MIS instruments in which a grounding component is effected at a user's wrist via a wrist grounding component that is received over the user's wrist; the surgical tool 10 lacks such a wrist grounding component according to the embodiments of the figures.

Figure 14:
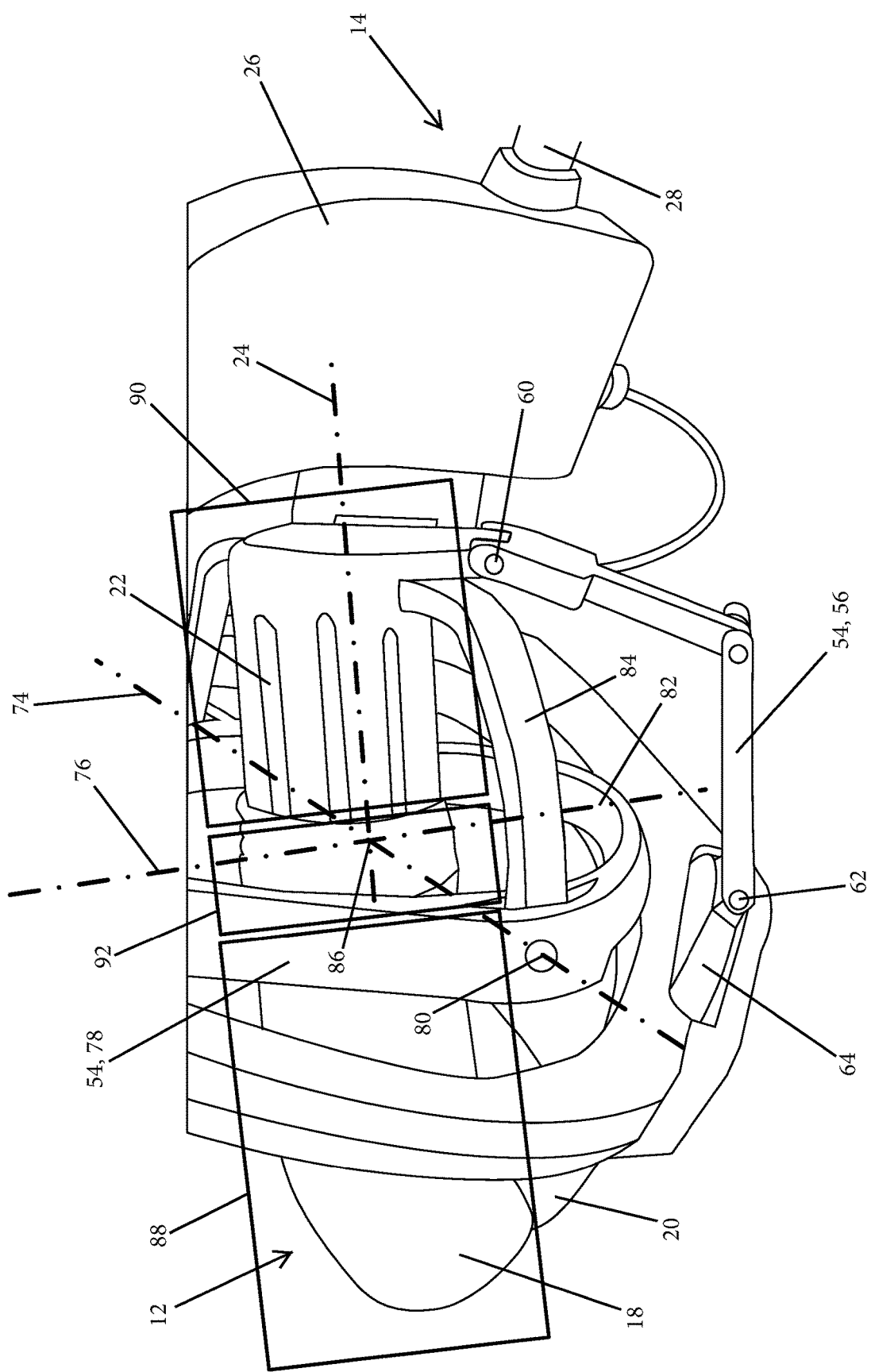
FIG. 14 is an enlarged view of the handle assembly and frame assembly of FIG. 10.
Figure 15:
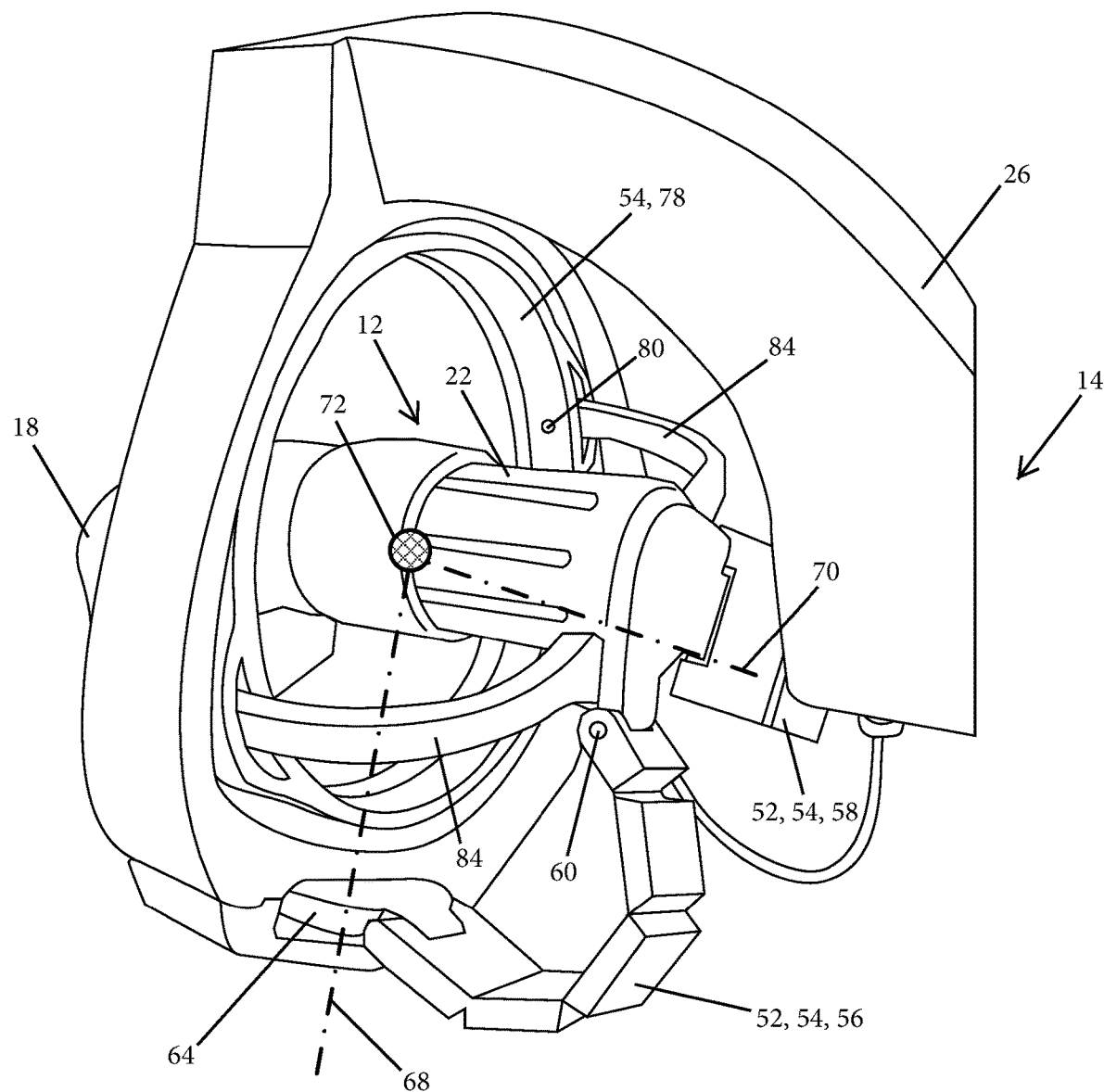
FIG. 15 is a perspective view of another embodiment of the first architecture (I) of the handle assembly and frame assembly of the surgical tool assembly, this view intended to demonstrate an articulation input joint thereof.
Figure 16:
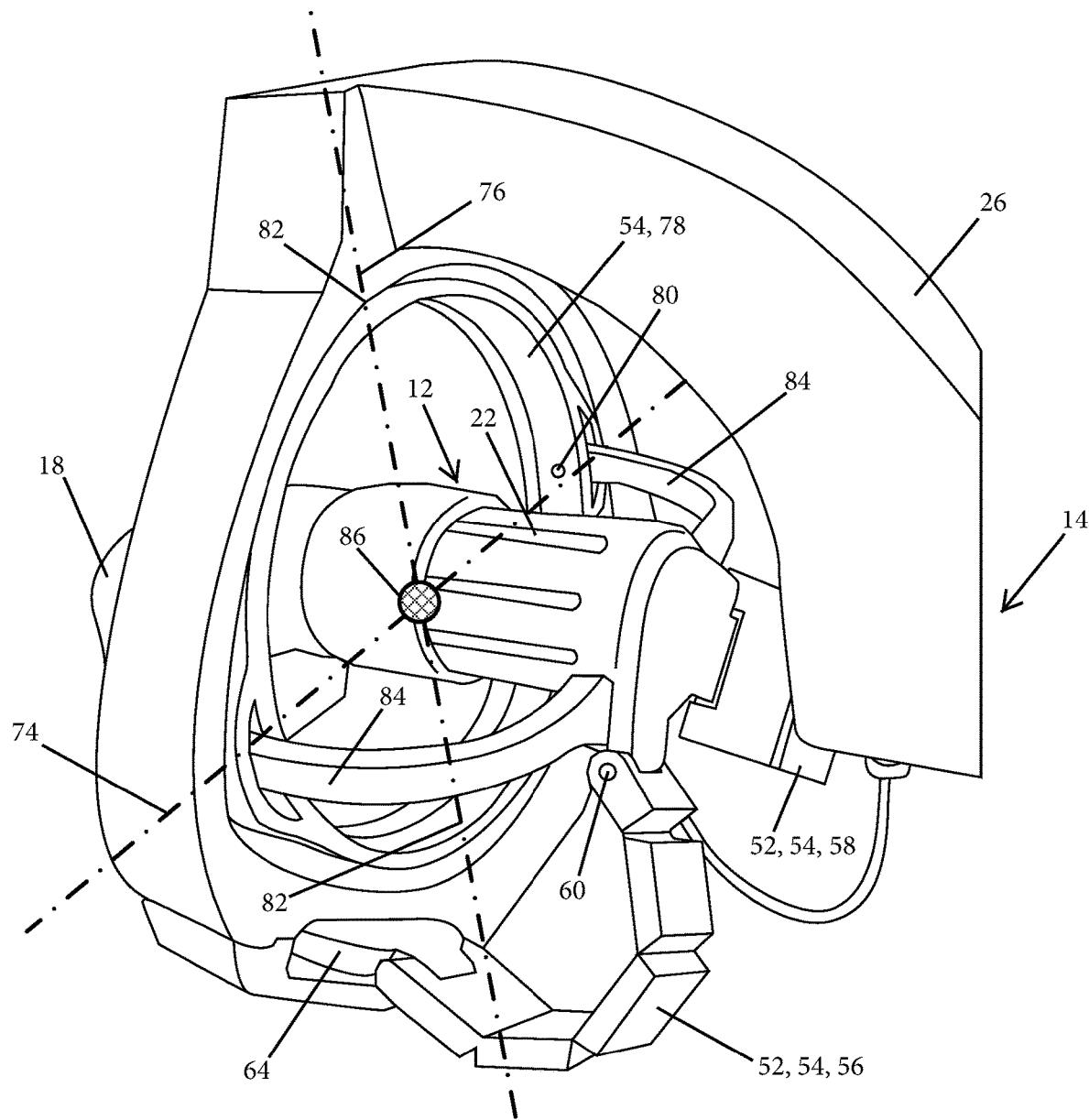
FIG. 16 is the perspective view of FIG. 15, this view intended to demonstrate an axial grounding joint of the handle assembly and frame assembly of the surgical tool assembly.

Furthermore, it may not only be that the user can control all useful EE motions through position and orientation of the handle assembly 12, but device usability may be influenced by relative position of the handle assembly 12 along the handle axis 24 relative to the virtual center (i.e., VC-AIJ 72 and VC-AGJ 86). With reference to FIG. 14, at least per this embodiment, the handle assembly 12 may be delineated as having three regions: a proximal region 88, a distal region 90, and a central region 92. The proximal region 88 is where the user's palm resides and grips. It is at this location of the handle assembly 12 that the surgical tool 10 is principally supported. The distal region 90 is where the user's fingers reside and is where fine motions inputs are received. The central region 92 is the zone between the proximal and distal regions 88, 90 of the handle assembly 12 and may simply be the plane which bisects the handle assembly 12. The handle assembly 12 may be embodied as basic as a single rigid cylindrical member with mounts to the AIJ 32 and AGJ 50 members, or in a form that is ergonomically designed for a hand of a user (e.g., optimized for right-hand grip, left-hand grip, small hand, large hand, or non-handed and universal). A handle to provide the desired degree of usability for the surgical tool 10, it is within the central region 92 of the handle assembly 12 that the virtual center (i.e., VC-AIJ 72 and VC-AGJ 86) may be located, per at least some embodiments.

In at least some embodiments, the handle assembly 12 does not necessarily need to be embodied as illustrated in the figures and including two sub-assemblies, namely the handle body 18 and dial 22. The handle assembly 12 may simply be a single body without discrete distinctions between its regions. In such an embodiment, the surgical tool 10 would not facilitate roll functionality within the device. The user, however, may provide a roll input by pronation or supination of their hand, and by extension of their wrist and forearm. Their pronation or supination input motions will result in roll about the shaft axis 30.

Figure 2:
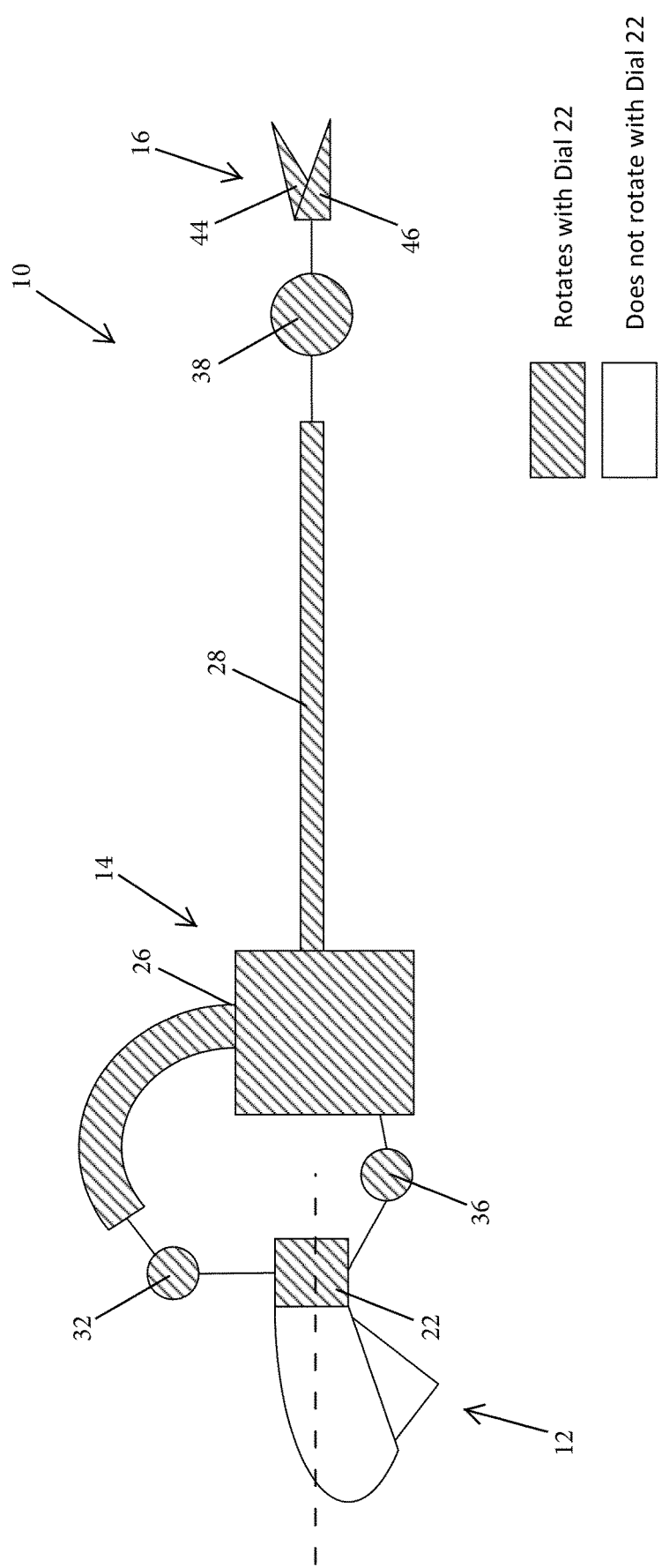
FIG. 2 is another schematic of the surgical tool.

The handle assembly 12 may be configured that the proximal and distal regions 88, 90 are two separate bodies which incorporate a relative roll DoF therebetween. With this configuration, and the bodies maintain a consistent handle axis 24 while providing roll DoF between the two bodies. The distal body in the handle assembly 12 may be called the dial 22. The dial 22 is intended to be controlled by a user that grips the dial 22 and rotationally positions it relative to the proximal handle body 18. When a device is configured with a handle assembly 12 containing the dial 22, the components within the device that are impacted by roll are depicted in FIG. 2. Namely, the AIJ 32, closure actuation joint 36, frame assembly 14, frame 26, shaft 28, output articulation joint 38, and EE assembly 16 would all rotate with the dial 22 upon roll functionality, according to at least some embodiments.

With the virtual center (i.e., VC-AIJ 72 and VC-AGJ 86) located in the central region 92 of the handle assembly 12, the proximal and distal regions 88, 90 of the handle assembly 12 may consequently inherit unique characteristics per at least some embodiments. For example, when the handle assembly 12 rotates about the pitch axis 74, a portion of the handle assembly 12 moves in a positive +Z-direction and the opposite portion of the handle assembly 12 moves inversely in a negative −Z-direction. Similarly, when the handle assembly 12 rotates about the yaw axis 76, a portion of the handle assembly 12 moves in a positive +Y-direction and the opposite portion of the handle assembly 12 moves in a −Y direction. When there is a pitch input to the handle assembly 12, yaw input to the handle assembly 12, or any combination thereof, there is no impact to the location of the virtual center and, in turn, no impact to the position or orientation of the frame assembly 14 relative to the trocar. Conversely, with rigid body motions of the handle assembly 12 in X-, Y-, and Z-directions the motions directly impact frame position at the virtual center. Due to the parallel kinematic structures, the rigid body motion inputs to the handle assembly 12 have no impact to the pitch and yaw orientation of the handle assembly 12 nor the EE assembly 16. When the EE assembly 16 is not articulated, it can be seen that the EE axis 48 is co-linear with the shaft axis 30 and handle axis 24.

Moreover, in at least some embodiments, the VC-AIJ 72 resides at a location that is occupied by the handle assembly 12, such as at a location occupied by the handle body 18 or at a location occupied by the dial 22. The VC-AIJ 72 can further reside at a location that is occupied by a user's hand 94 (FIG. 13) when the user is grasping the handle assembly 12 in order to manipulate the handle assembly 12—this location could be at the handle body 18, at the dial 22, or at a distance set back and rearward of the handle body 18 generally along the handle axis 24. This location could also be within the confines established in part by a user's palm when the user is grasping the handle assembly 12 in order to manipulate it. In a similar way, the VC-AGJ 86 can reside at a location that is occupied by the handle assembly 12, such as at a location occupied by the handle body 18 or at a location occupied by the dial 22. The VC-AGJ 86 can further reside at a location that is occupied by the user's hand 94 when the user is grasping the handle assembly 12 in order to manipulate the handle assembly 12—this location could be at the handle body 18, at the dial 22, or at a distance set back and rearward of the handle body 18 generally along the handle axis 24. This location could also be within the confines established in part by a user's palm when the user is grasping the handle assembly 12 in order to manipulate it.

Additionally, in at least some embodiments, the configuration of the surgical tool 10 allows for a functional performance characteristic called an articulated roll. The articulated roll takes place when the handle assembly 12 is first rotated to position that may be any combination of pitch/yaw angle and the handle assembly 12 is maintained in that orientation relative to the trocar relative ground. Then, the user provides a roll input to the distal region 90 of the handle assembly 12 (e.g., the dial 22). The result is that the orientation of the handle assembly 12 may remain stationary while the frame 26 rolls, or spins along the shaft axis 30. Combining the articulated roll input with functionality provided by a connected AIJ 32, the user may replicate the articulated roll at the EE assembly 16.

The location of the virtual center (i.e., VC-AIJ 72 and VC-AGJ 86) may also have an interesting impact on user experience during articulation motions. When the user provides a positive pitch input to the handle assembly 12, the distal region 90 of the handle assembly 12 moves in a positive +Y-direction. This correlates directly with the desired effect to the EE assembly 16 distally mounted to the frame 26 and shaft 28 subassembly when connected via pulleys and cables. In other words, the fine motor movement of the user's thumb and forefinger while gripping the distal region 90 of the handle assembly 12 are intuitively mapped to end-effector assembly motion. This occurs even despite the negative Y displacement of the proximal region 88 of the handle assembly 12 where a great proportion of the user input forces are located. The intuitive relationship exists for handle assembly 12 yaw motions as well.

In a parallel-kinematic (PK) mechanism, for pitch inputs, the handle assembly 12 rotates about the virtual center (i.e., VC-AIJ 72 and VC-AGJ 86). For clockwise pitch inputs (relative to orientation of FIG. 1) at the handle assembly 12, the distal region 90 of the handle assembly 12 shifts in the negative −Y-direction while the proximal region 88 of the handle assembly 12 shifts in the positive +Y-direction. The resultant motion of the EE assembly 16 is to articulate in a similar clockwise direction (south, or +Z axis rotation). This contrasts with the handle assembly 12 motion in a serial-kinematic (SK) mechanism with a distally located virtual center whereby the entire handle assembly 12 shifts in a positive +Y-direction while rotating clockwise. For a user to point the EE assembly 16 into the south direction of a device using a SK joint, the user raises the handle assembly 12 while rotating it about a distally-located virtual center.

3. Surgical Tool and Assembly Architectures I-V

According to at least some embodiments, the surgical tool 10 may be an assembly of various sub-assemblies, namely, the handle assembly 12, the frame 26, the shaft 28, and the EE assembly 16. There may also exist various joints/mechanisms and transmission assemblies within and/or between the sub-assemblies to facilitate certain functionality of the surgical tool 10. The surgical tool 10 may provide various functions which correspond to following output motions: i) articulation motion (i.e., pitch and yaw rotation) of the EE assembly 16; ii) rigid body motion of the shaft 28 and the EE assembly 16; iii) articulated roll motion of the EE assembly 16 (or portion thereof); and iv) jaw closure motion at the EE assembly 16.

Although the surgical tool 10 may be configured with the jaw closure motion function (iv), the function is facilitated via a series of interconnected transmission members mounted between the bodies mentioned above. This embodiment (FIG. 1) would have the handle assembly 12, frame assembly 14, and EE assembly 16 (or similarly manipulated assembly).

Of the four functions identified, the two primary functions per certain embodiments are articulation motion of the EE assembly 16 and rigid body motion of the shaft 28 and of the EE assembly 16. The articulation function and rigid body motion, and particularly the rigid body motion along the shaft axis 30, are described by way of surgical tool constraint maps. FIGS. 9-16 show embodiments of the interfaces between the handle assembly 12 and the frame assembly 14 that are established via joints/mechanisms. This function pertaining to rigid body motion of handle assembly 12, frame 26, and the overall surgical tool 10 along the shaft axis 30 is also referred to as axial grounding. One interface relates to the articulation function which is facilitated by a 2 DoF pitch and yaw motion articulation input joint/mechanism. This joint is the AIJ 32. Another interface is related to the axial grounding function which is facilitated by a 1 DoC joint/mechanism along shaft axis 30. This joint is the AGJ 50. These respective joints may be same or separate joints/mechanisms, according to different embodiments. Various constraint maps that are discussed below go through different types of such joints.

FIG. 3 is a chart that presents multiple surgical tool architectures and various joints that can effect the functionality at the interfaces set forth above, per at least some embodiments of the surgical tool 10.

Figure 5:
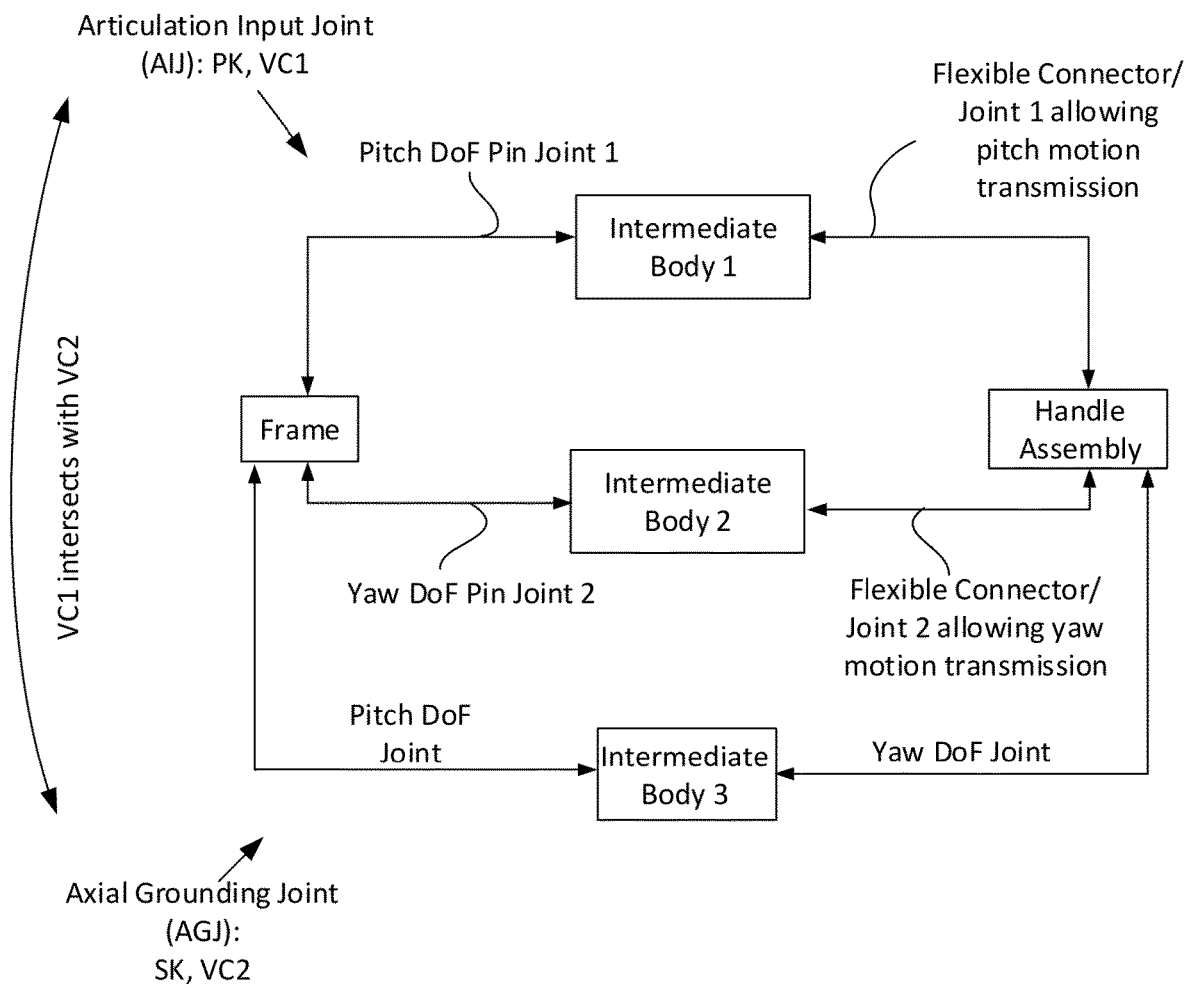
FIG. 5 is a schematic diagram demonstrating a first architecture (I) of an embodiment of the handle assembly and frame assembly of a surgical tool assembly.

Surgical tool architecture I refers to an apparatus which utilizes a parallel-kinematic (PK) joint as the AIJ 32. The PK AIJ 32 provides independent pitch and yaw motion paths to transmit motion from the handle assembly 12 to the EE assembly 16. The PK AIJ 32 is also a virtual center (VC1) joint, meaning it establishes the VC-AIJ 72. The AGJ 50 for architecture I is a serial-kinematic (SK), virtual center (VC2) joint. The VC-AGJ 86 is established in this architecture. The VC-AIJ 72 and VC-AGJ 86 generally intersect and coincide, as previously described, to form a common virtual center of rotation. In case the VC-AIJ 72 and VC-AGJ 86 do not intersect and coincide, the kinematics may get compromised and this may lead to binding/freezing of motion due to a lack of a single virtual center of rotation. Architecture I is shown in the schematic diagram of FIG. 5. In FIG. 5, the PK AIJ 32 is demonstrated via the intermediate body 1, intermediate body 2, pitch DoF pin joint 1, flexible connector/joint 1 allowing pitch motion transmission, yaw DoF pin joint 2, and flexible connector/joint 2 allowing yaw motion transmission. The SK AGJ 50 is demonstrated via the intermediate body 3, pitch DoF joint, and yaw DoF joint.

Figure 6:
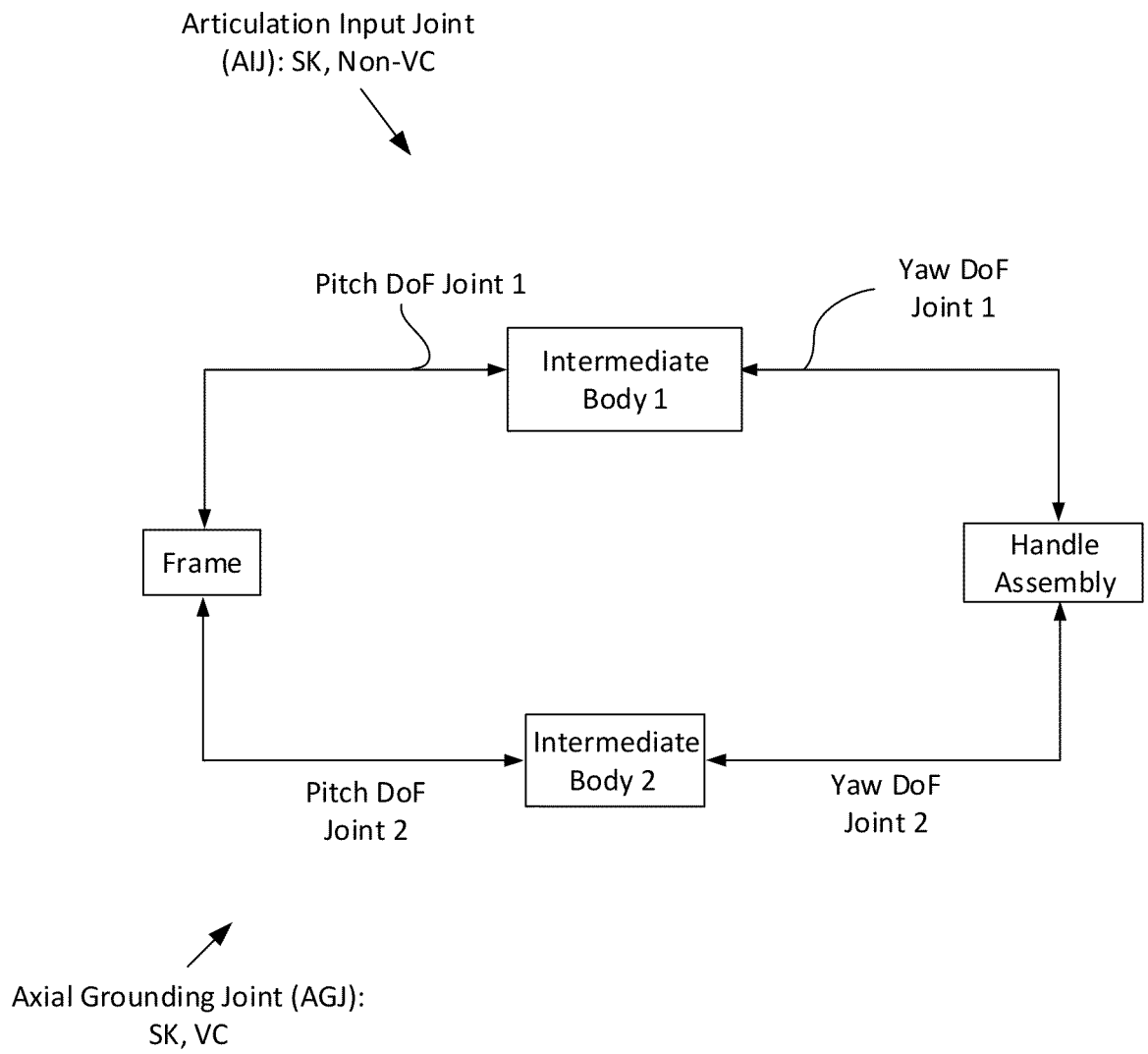
FIG. 6 is a schematic diagram demonstrating a second architecture (II) of an embodiment of the handle assembly and frame assembly of the surgical tool assembly.

Surgical tool architecture II utilizes an AIJ 32 that is a serial-kinematic (SK), non-virtual center (VC) joint. In a non-VC joint, the pitch axis of rotation 74 and the yaw axis of rotation 76 do not intersect with each other. The AGJ 50 in the case of architecture II is a SK, VC joint. The VC-AGJ 86 is established in this architecture. Architecture II is shown in the schematic diagram of FIG. 6. In FIG. 6, the SK AIJ 32 is demonstrated via the intermediate body 1, pitch DoF joint 1, and yaw DoF joint 1. The SK AGJ 50 is demonstrated via the intermediate body 2, pitch DoF joint 2, and yaw DoF joint 2.

Figure 7:
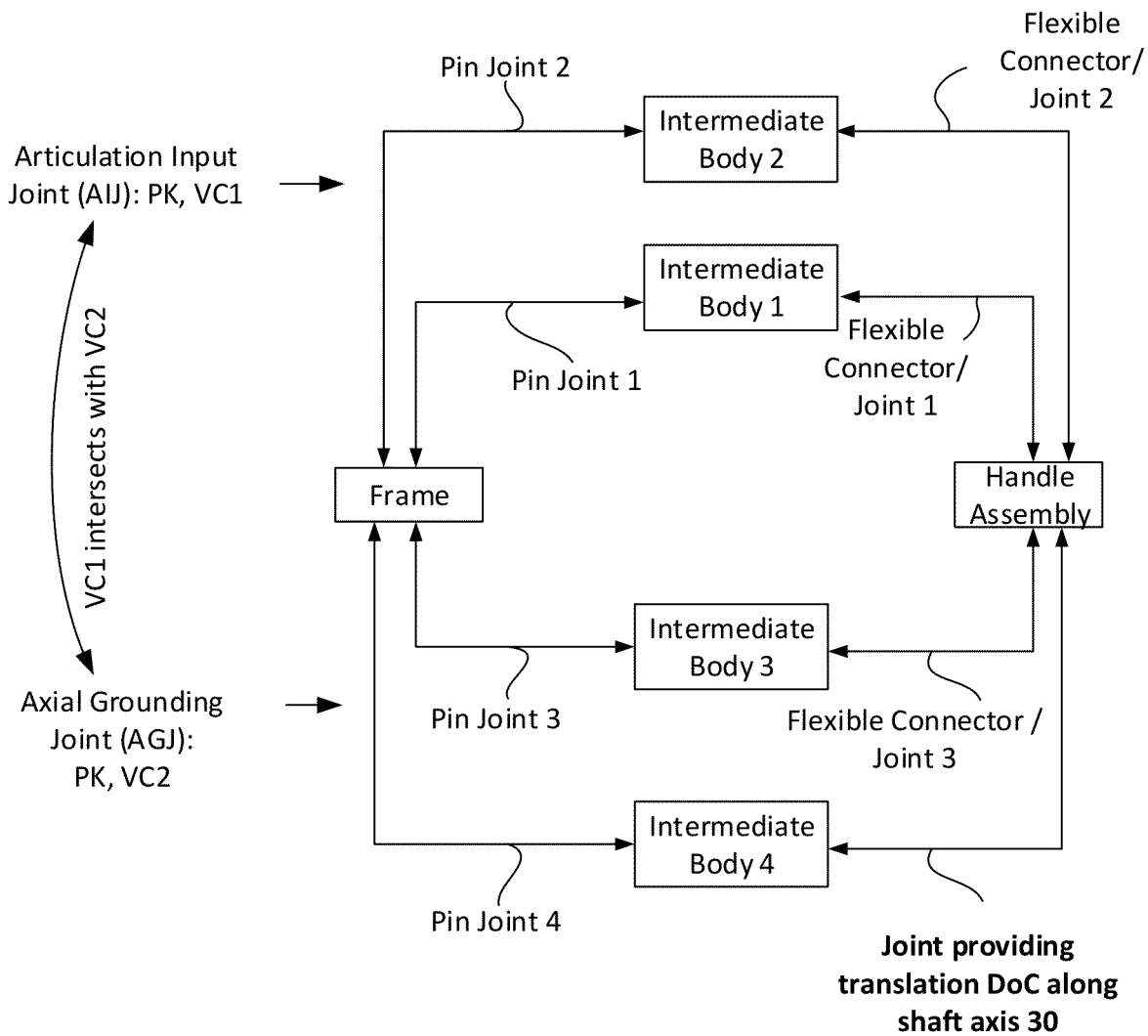
FIG. 7 is a schematic diagram demonstrating a third architecture (III) of an embodiment of the handle assembly and frame assembly of the surgical tool assembly.

Surgical tool architecture III utilizes an AIJ 32 that is a parallel-kinematic (PK), virtual center (VC1) joint. The VC-AIJ 72 is established in this architecture. The AGJ 50 in the case of architecture III is a parallel-kinematic (PK), virtual center (VC2) joint which also provides translation DoC along shaft axis 30 apart from allowing pitch and yaw DoF motions. The VC-AGJ 86 is established in this architecture. The VC-AIJ 72 and VC-AGJ 86 generally intersect and coincide, as previously described, to form a common virtual center of rotation. In case the VC-AIJ 72 and VC-AGJ 86 do not intersect and coincide, the kinematics may get compromised and this may lead to binding/freezing of motion due to a lack of a single virtual center of rotation. Architecture III is shown in the schematic diagram of FIG. 7. In FIG. 7, the PK AIJ 32 is demonstrated via the intermediate body 1, intermediate body 2, pin joint 1, flexible connector/joint 1, pin joint 2, and flexible connector/joint 2. The PK AGJ 50 is demonstrated by the intermediate body 3, intermediate body 4, pin joint 3, flexible connector/joint 3, pin joint 4, and joint providing translation DoC along the shaft axis 30.

Figure 8:
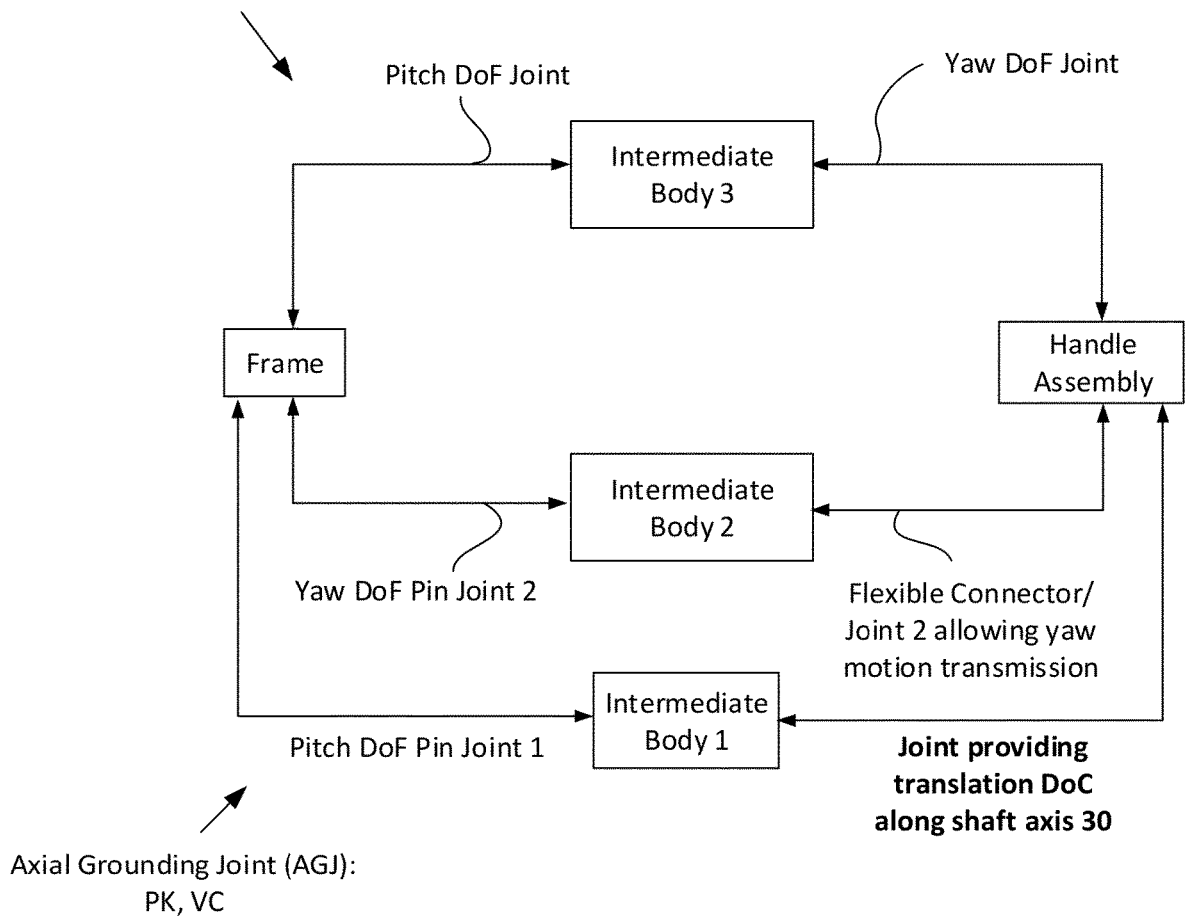
FIG. 8 is a schematic diagram demonstrating a fourth architecture (IV) of an embodiment of the handle assembly and frame assembly of the surgical tool assembly.
Figure 9:
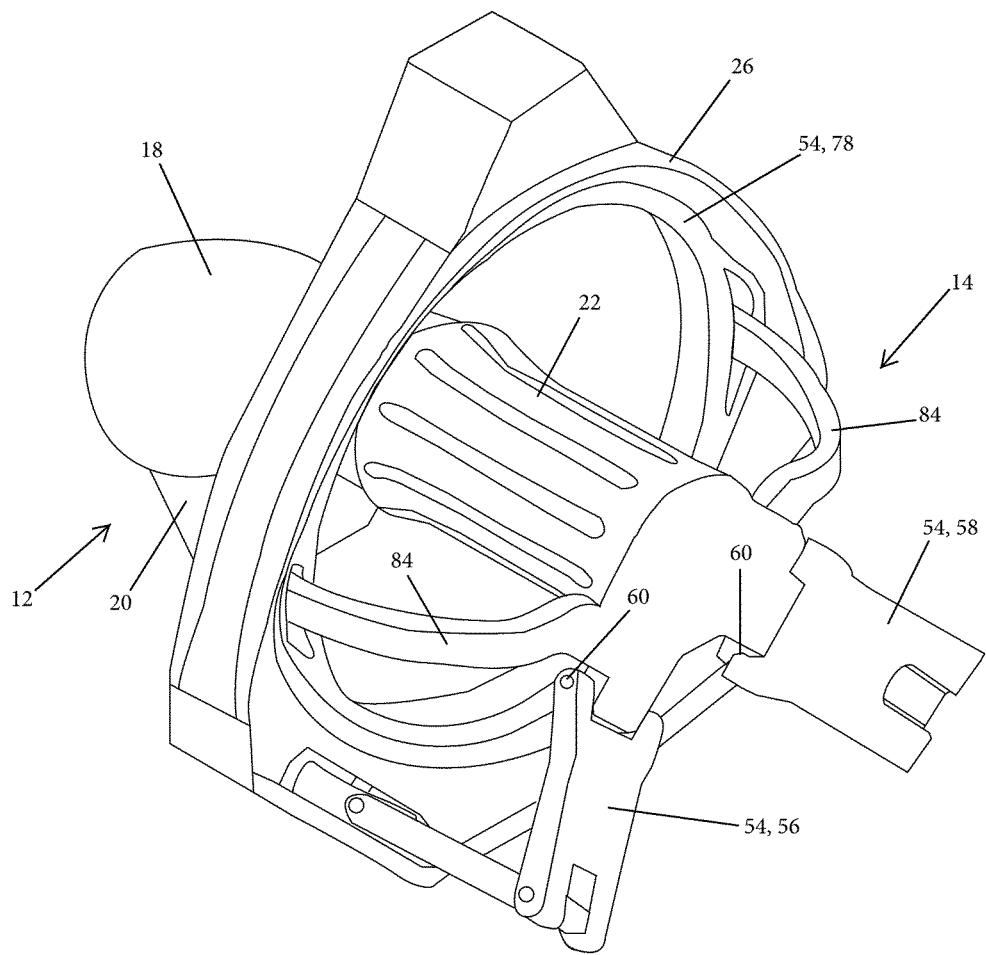
FIG. 9 is a perspective view of an embodiment of the first architecture (I) of the handle assembly and frame assembly of the surgical tool assembly.
Figure 10:
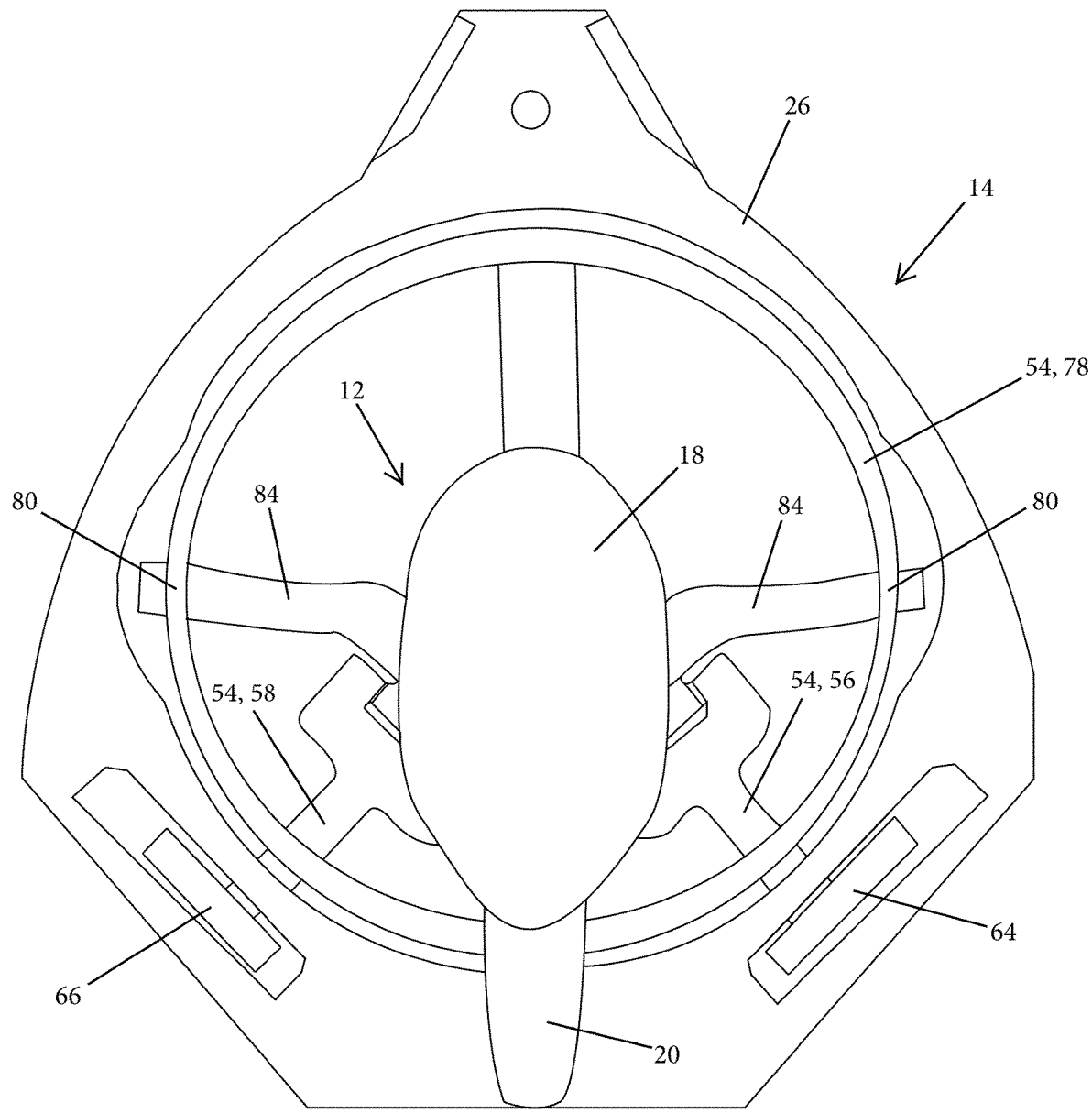
FIG. 10 is a rear view of another embodiment of the first architecture (I) of the handle assembly and frame assembly of the surgical tool assembly.
Figure 11:
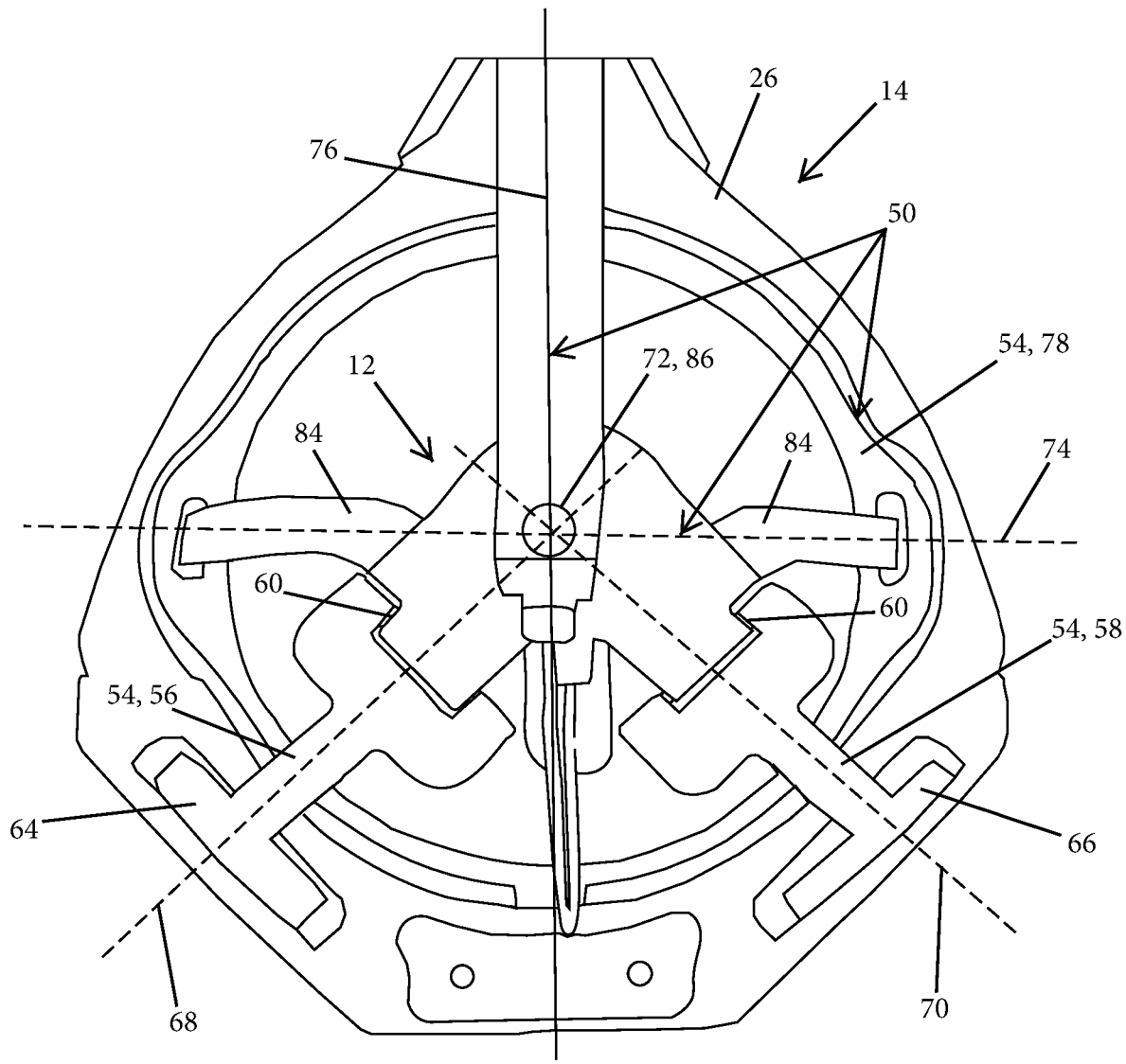
FIG. 11 is a front view of the handle assembly and frame assembly of FIG. 10.
Figure 12:
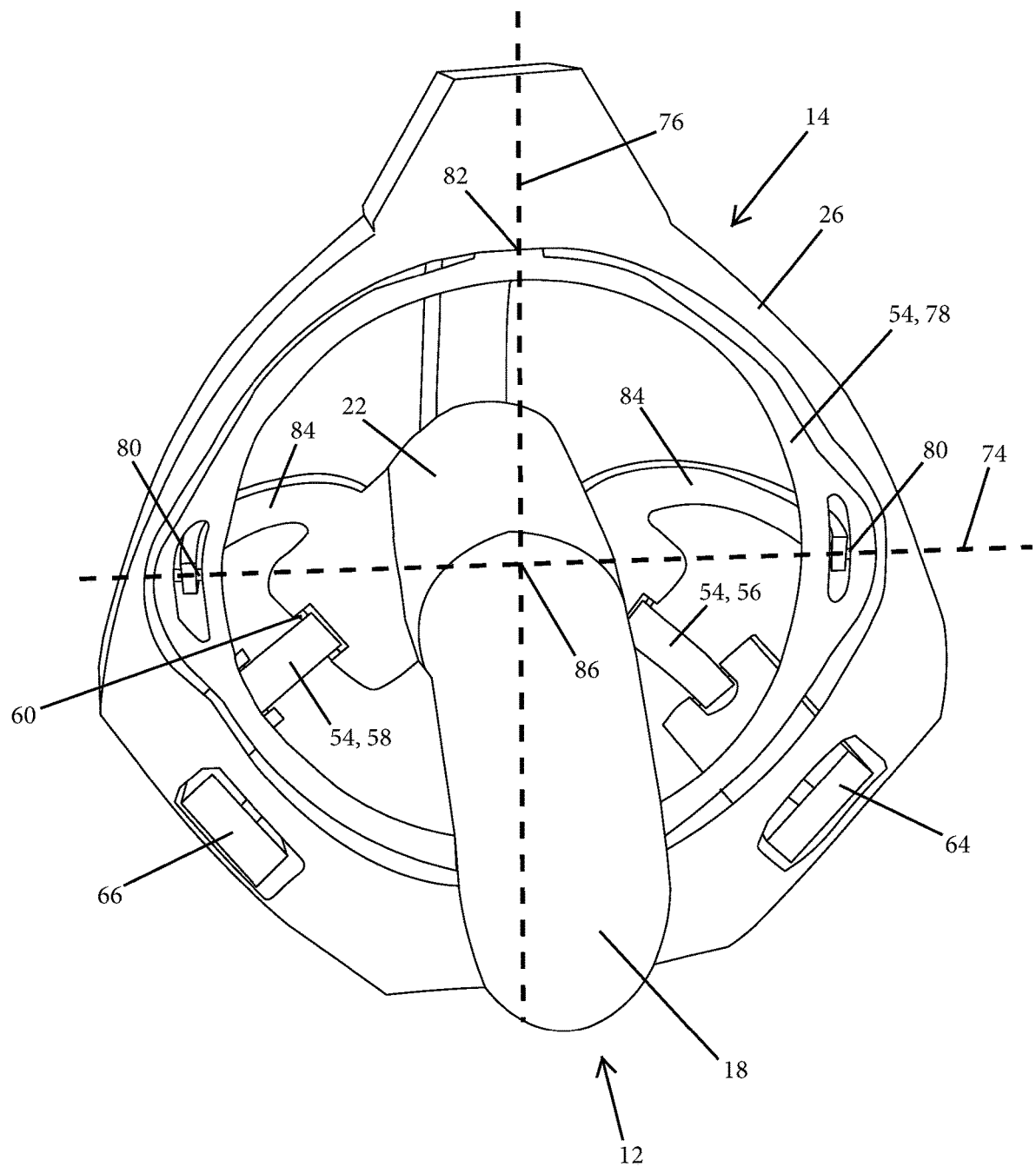
FIG. 12 is another rear view of the handle assembly and frame assembly of FIG. 10.
Figure 13:
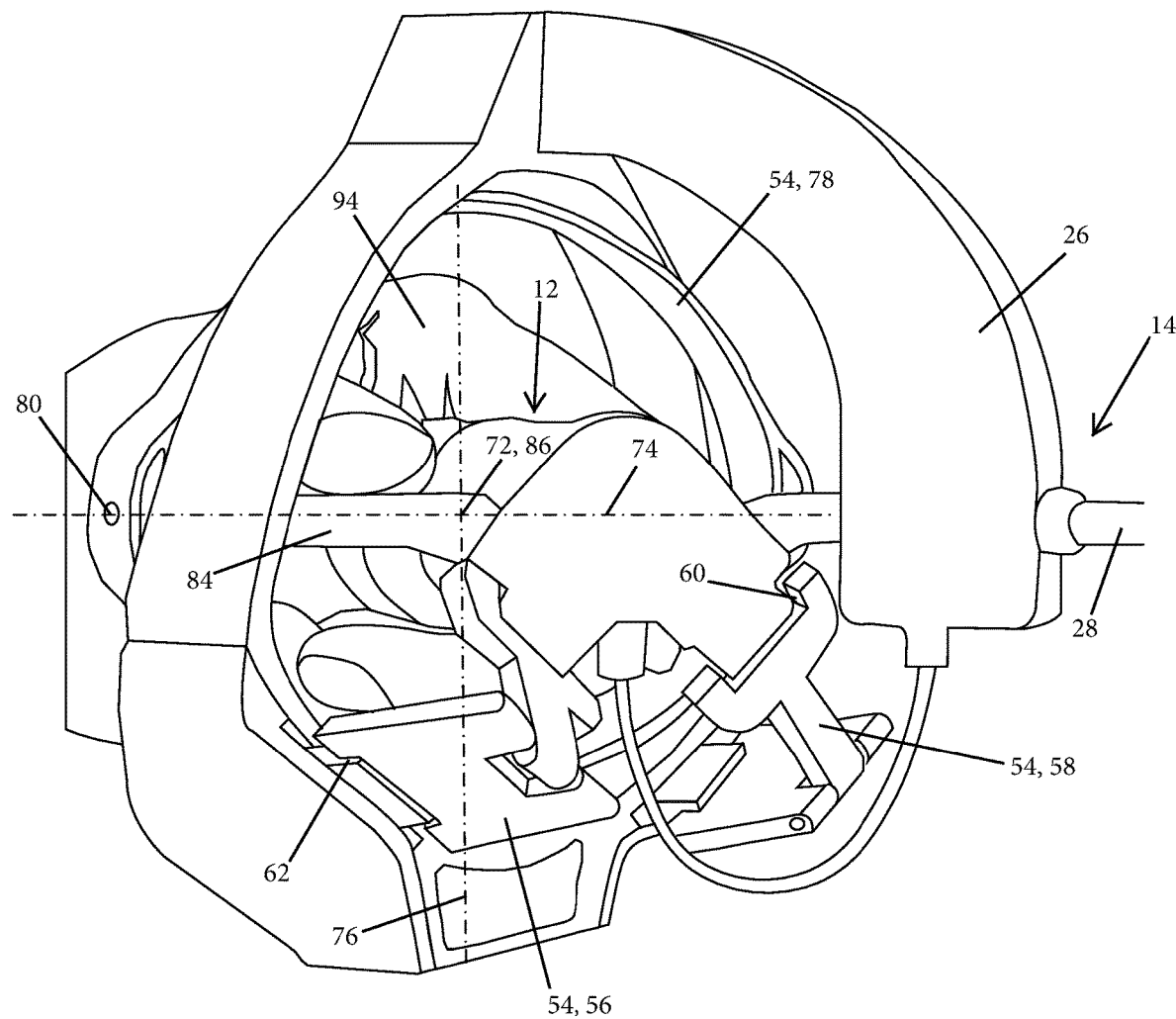
FIG. 13 is another perspective view of the handle assembly and frame assembly of FIG. 10.

Surgical tool architecture IV utilizes an AIJ 32 that is a serial-kinematic (SK), non-virtual (VC) joint. In a non-VC joint, the pitch axis of rotation 74 and the yaw axis of rotation 76 do not intersect with each other. The AGJ 50 in the case of architecture IV is a parallel-kinematic (PK), VC joint which also provides translation DoC along shaft axis 30 apart from allowing pitch and yaw DoF motions. The VC-AGJ 86 is established in this architecture. Architecture IV is shown in the schematic diagram of FIG. 8. In FIG. 8, the SK AIJ 32 is demonstrated via the intermediate body 3, pitch DoF joint, and yaw DoF joint. The PK AGJ 50 is demonstrated by the intermediate body 1, intermediate body 2, pitch DoF pin joint 1, joint providing translation DoC along the shaft axis 30, yaw DoF pin joint 2, and flexible connector/joint 2 allowing yaw motion transmission.

Figure 33:
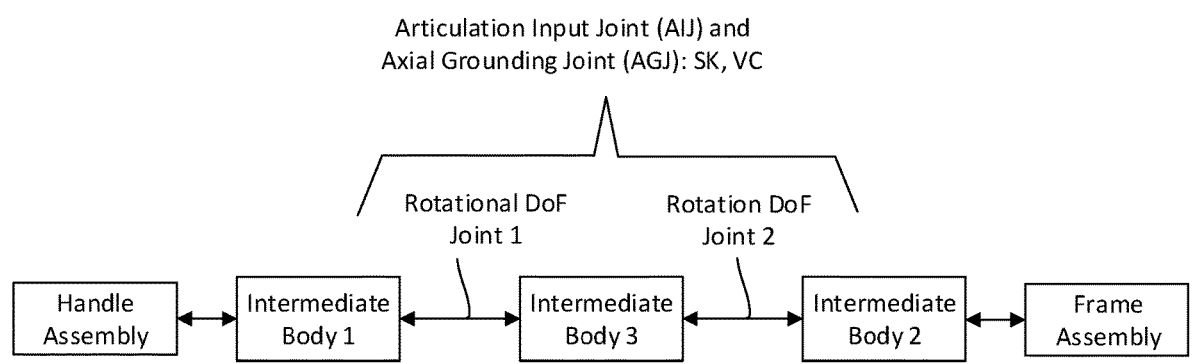
FIG. 33 a schematic diagram demonstrating a fifth architecture (V) of an embodiment of the handle assembly and frame assembly of the surgical tool assembly.
Figure 34:
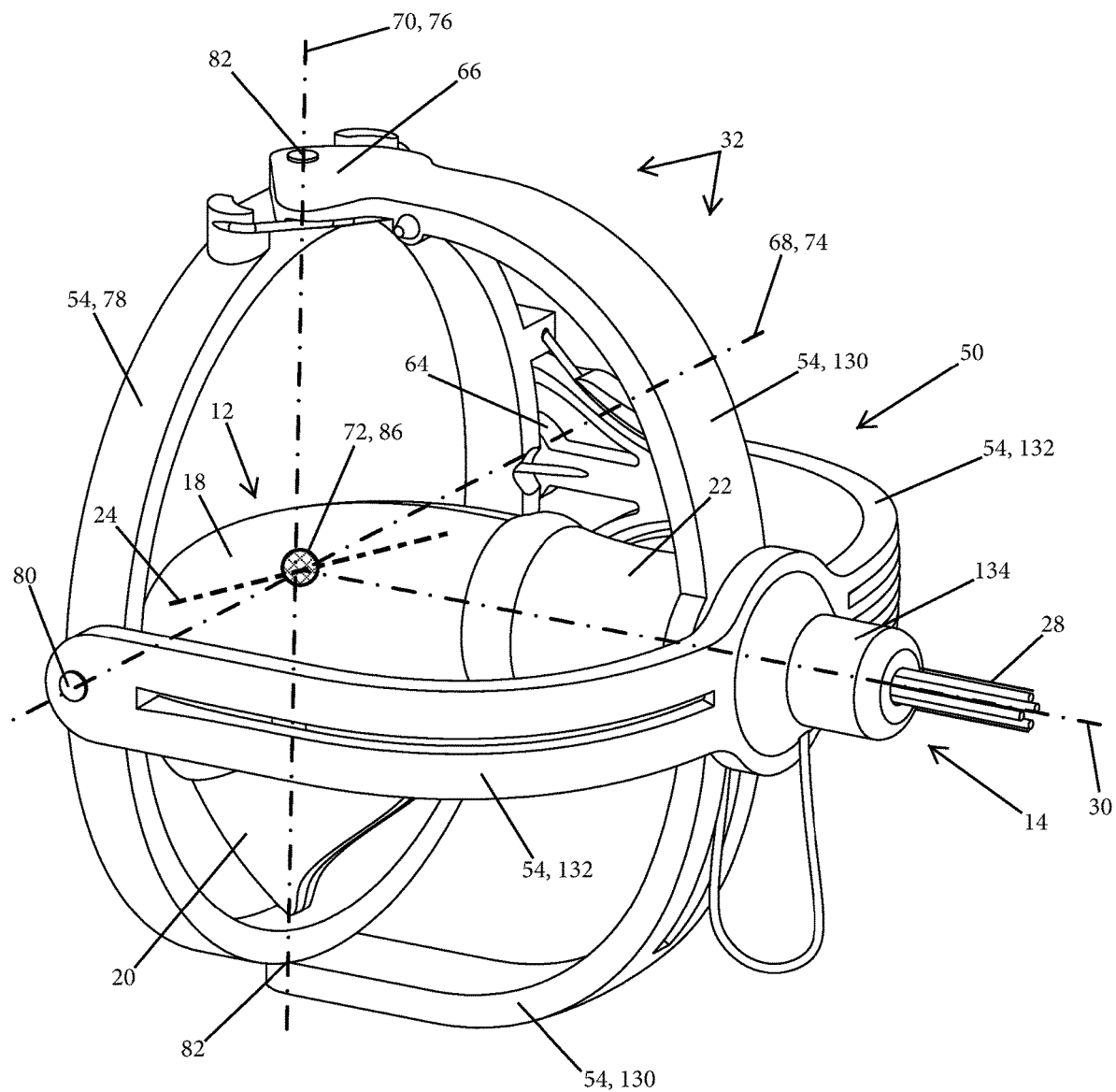
FIG. 34 is a perspective view of an embodiment of the fifth architecture (V) of the handle assembly and frame assembly of the surgical tool assembly.
Figure 35:
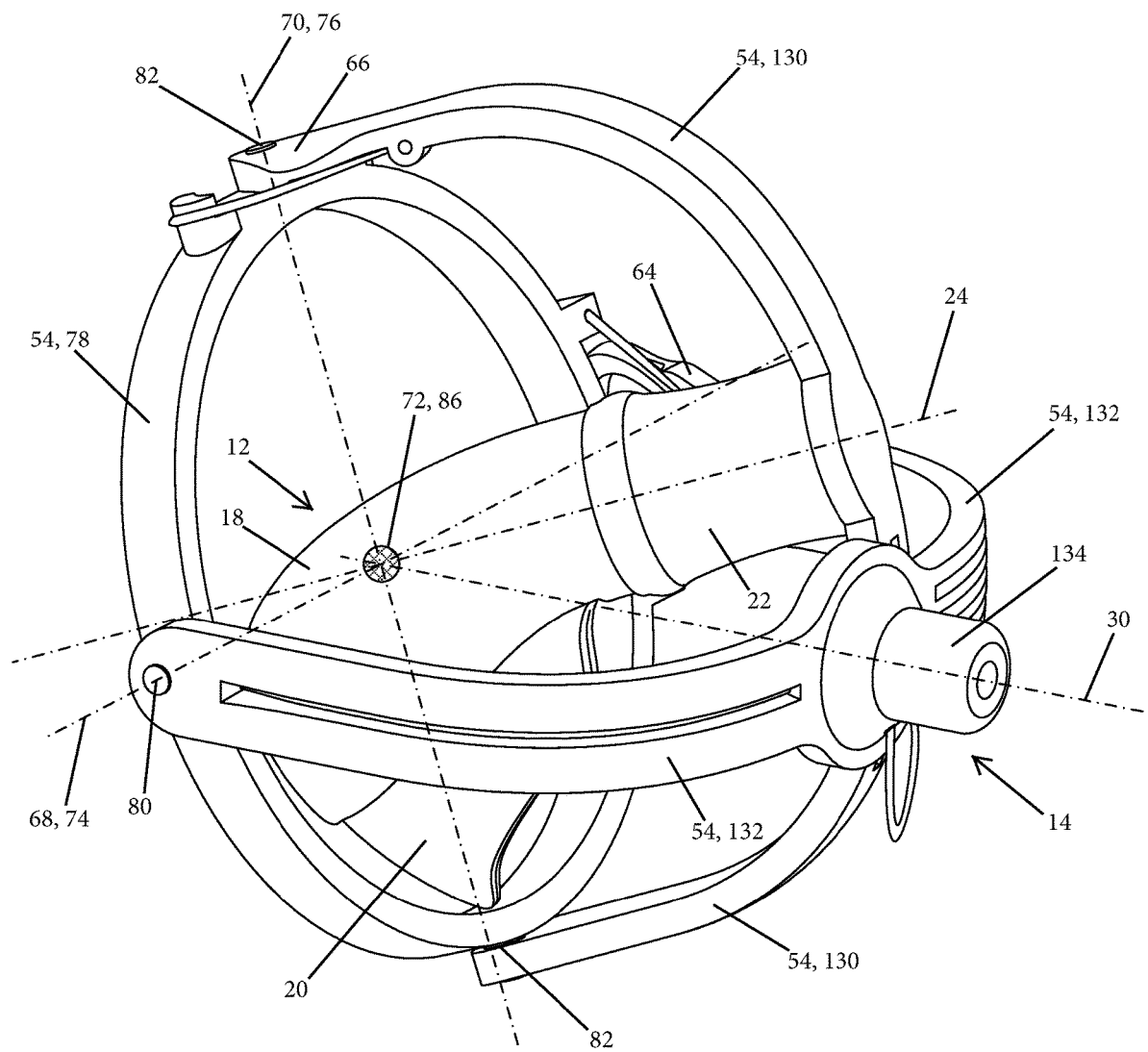
FIG. 35 is another perspective view of the surgical tool assembly of FIG. 34.
Figure 36:
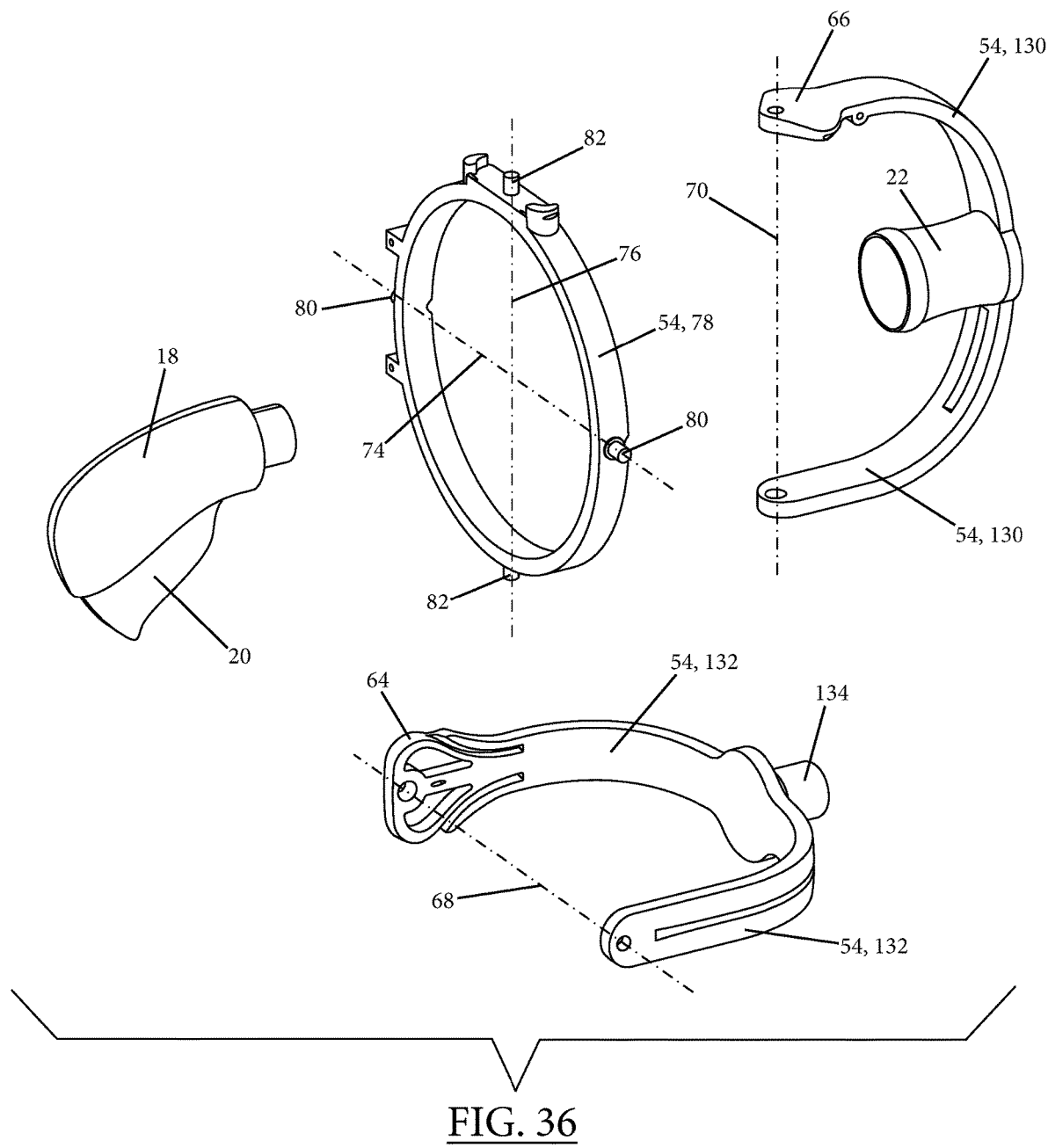
FIG. 36 is an exploded view of the surgical tool assembly of FIG. 34.
Figure 37:
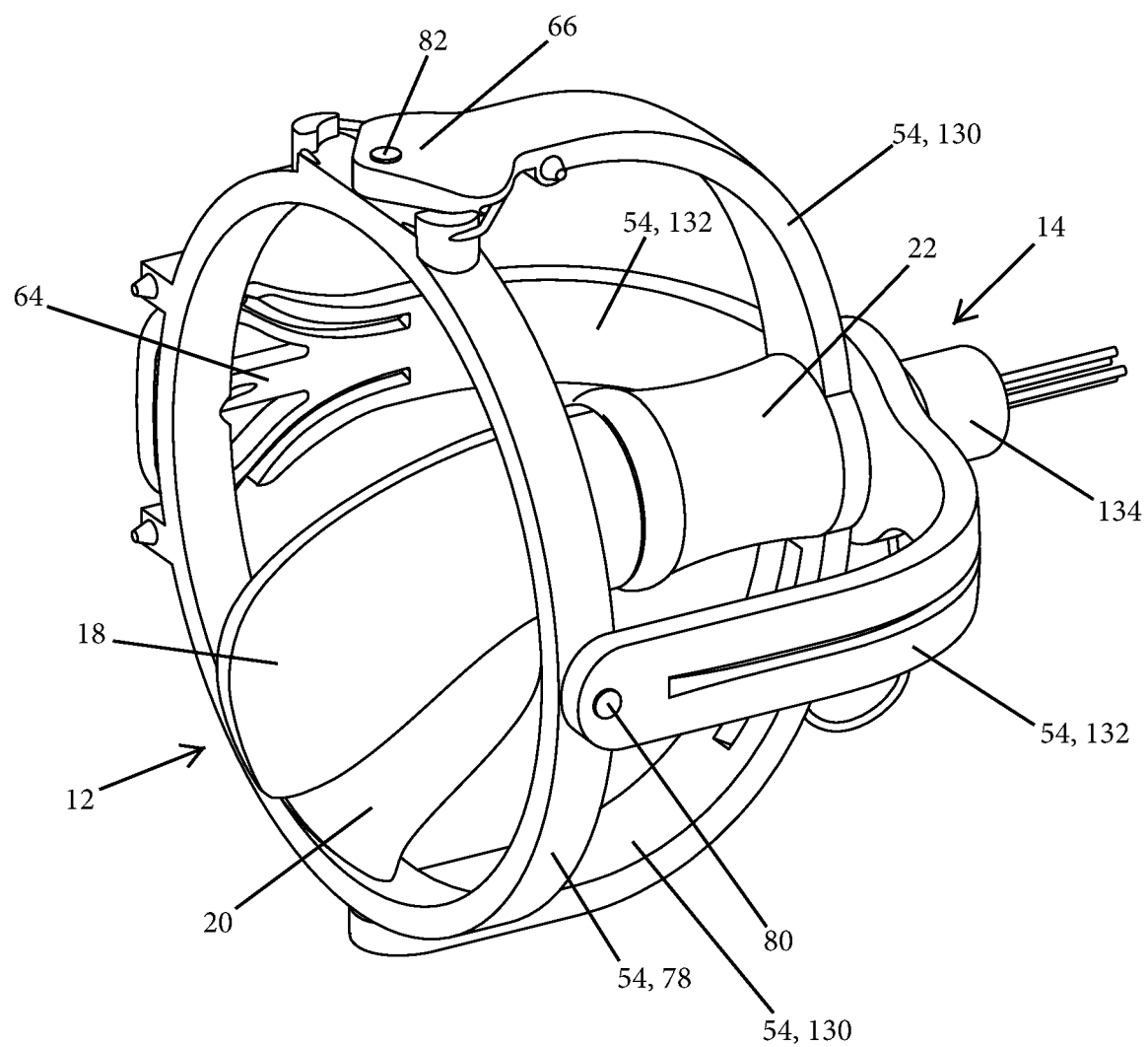
FIG. 37 is another perspective view of the surgical tool assembly of FIG. 34.

Surgical tool architecture V utilizes an AIJ 32 that is a serial-kinematic (SK), virtual center (VC1) joint. The VC-AIJ 72 is established in this architecture. The AGJ 50 in the case of architecture V is a serial-kinematic (SK), virtual center (VC2) joint which also provides translation DoC along the shaft axis 30 apart from allowing pitch and yaw DoF motions. The VC-AGJ 86 is established in this architecture. The VC-AIJ 72 and VC-AGJ 86 generally intersect and coincide, as previously described, to form a common virtual center of rotation. Architecture V is shown in the schematic diagram of FIG. 33. In FIG. 33, the SK AIJ 32 is demonstrated via the intermediate body 1, intermediate body 2, intermediate body 3, rotational DoF joint 1, and rotational DoF joint 2. The SK AGJ 50 is demonstrated via the intermediate body 1, intermediate body 2, intermediate body 3, rotational DoF joint 1, and rotational DoF joint 2.

3.1 Architecture I

The embodiments of FIGS. 9-23, 28, and 32 all present the surgical tool 10 and an assembly thereof consisting of the handle assembly 12 and frame assembly 14 that exhibit the first architecture I. In architecture I, as set forth above, the PK AIJ 32 is provided, and the VC-AIJ 72 and VC-AGJ 86 are established. These embodiments map to the schematic diagram of FIG. 5. With general reference to FIGS. 9-23, 28, and 31, the first pulley axis 68 and the second pulley axis 70 represent the two axes of rotation which are orthogonal with respect to each other. About the first and second pulley axes 68, 70, the two degrees of freedom are captured to produce articulation at the EE assembly 16. The first and second pulley axes 68, 70, in certain scenario, may generally intersect and generally coincide with the pitch axis 74 and the yaw axis 76, respectively. The first and second pulley axes 68, 70 also meet via intersection at the VC-AIJ 72.

The handle assembly 12, specifically the dial 22 in this embodiment, is connected to the frame 26 via the first pulley 64 which is considered an intermediate body 54 in at least some embodiments, and is connected to the frame 26 via the second pulley 66 which is also considered an intermediate body 54 in at least some embodiments. Rotation of the first pulley 64 about the first pulley axis 68 captures one motion, whereas rotation of the second pulley 66 about the second pulley axis 70 captures another motion. Given the orthogonality between the first and second pulley axes 68, 70, these two motions are mutually exclusive and therefore, account for two DoF motions of the EE assembly 16. The first intermediate body 56, or first connector, that links the dial 22 to the first pulley 64 transmits handle assembly 12 motion when it rotates about the first pulley axis 68, and conversely does not transmit handle assembly 12 motion when it rotates solely about the second pulley axis 70. The same holds true for the second intermediate body 58, or second connector, that links the dial 22 to the second pulley 66. In the embodiments of FIGS. 9-14, the first and second intermediate bodies 56, 58 are shown as a series of planar linkages with pivots that facilitate rotation of the handle assembly 12 relative to the frame 26 about the pitch and yaw axes 74, 76. In the embodiments of FIGS. 15-23 and 28, the first and second intermediate bodies 56, 58 are shown as the flex strips 52 with pivots that facilitate rotation of the handle assembly 12 relative to the frame 26 about the pitch and yaw axes 74, 76. These intermediate bodies 56, 58 may also be flexible living hinges composed of a material such as polypropylene.

As set forth above, in architecture I, the SK AGJ 50 is provided and the VC-AGJ 86 is established. In FIGS. 9-16, the pitch and yaw DoF motions of the handle assembly 12, specifically the dial 22, are captured by the pitch DoF joint 80 between the dial 22 and the third intermediate body 78 or deviation ring, and is captured by the yaw DoF joint 82 between the frame assembly 14 and the third intermediate body 78 or deviation ring. In addition, as described, the AGJ 50 provides the translation degree of constraint along the shaft axis 30 between the handle assembly 12 and the frame assembly 14, among the other translation degrees of constraint provided by the AGJ 50 between the handle assembly 12 and the frame assembly 14 (i.e., y-axis and z-axis). The VC-AIJ 72 and VC-AGJ 86 generally coincide to provide a unified surgical tool and assembly consisting of two different types of joints that facilitate articulation and axial grounding functions. Here too, the handle axis 24 intersects the VC-AIJ 72 and intersects the VC-AGJ 86, and the shaft axis 30 likewise intersects the VC-AIJ 72 and intersects the VC-AGJ 86.

In architecture I, and as previously described, the VC-AIJ 72 resides at a location that is occupied by the handle assembly 12, can reside at a location that is occupied by a user's hand 94 when the user is grasping the handle assembly 12 in order to manipulate the handle assembly 12, or can reside at both locations when those locations are one and the same. In a similar way, the VC-AGJ 86 resides at a location that is occupied by the handle assembly 12, can reside at a location that is occupied by a user's hand 94 when the user is grasping the handle assembly 12 in order to manipulate the handle assembly 12, or can reside at both locations when those locations are one and the same.

Figure 32:
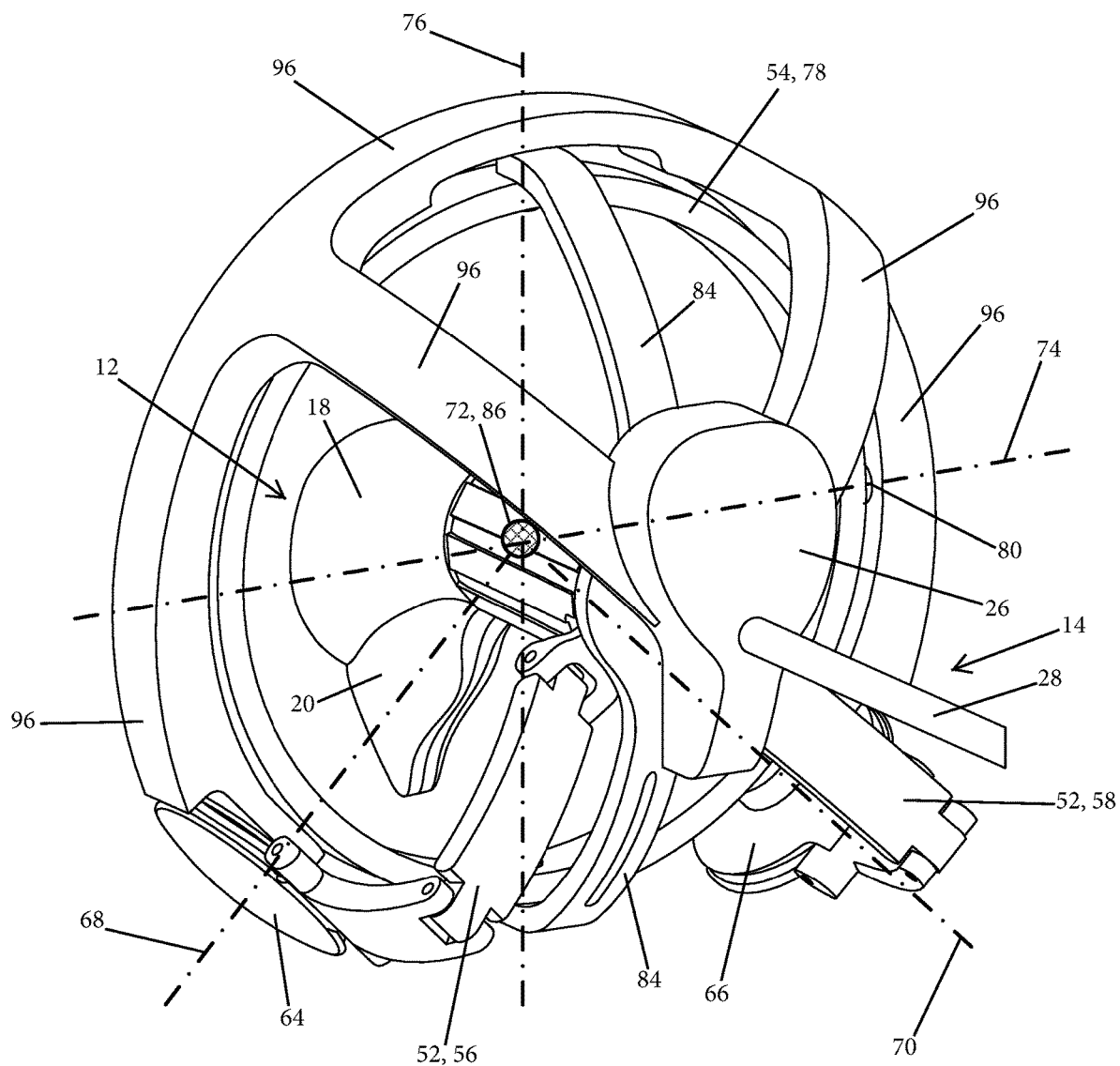
FIG. 32 is a perspective view of another embodiment of the first architecture (I) of the handle assembly and frame assembly of the surgical tool assembly.

Furthermore, the embodiments of FIGS. 17-23 and FIG. 28 differs in some regards with the embodiments of FIGS. 9-16. For instance, the frame 26 in FIGS. 17-23 and 28 has unitary extension arms 96. The extension arms 96 are rigid bodies, and can constitute intermediate bodies of the surgical tool 10 or can be constituent parts of the frame assembly 14. Also, the pin joints that furnish the pitch DoF joint 80 are a connection between the frame 26 and its extension arms 96 and the third intermediate body 78 or deviation ring; and the pin joints that furnish the yaw DoF joint 82 are a connection between the handle assembly 12 and its extension arms 84 and the third intermediate body 78 or deviation ring. The embodiment of FIG. 32 is similar in many regards to that of FIGS. 17-23 and 28. The frame 26 and extension arms 96 in FIG. 32 present a fuller ring-like shape than the same components in FIGS. 17-23 and 28.

3.2 Architecture II

Figure 24:
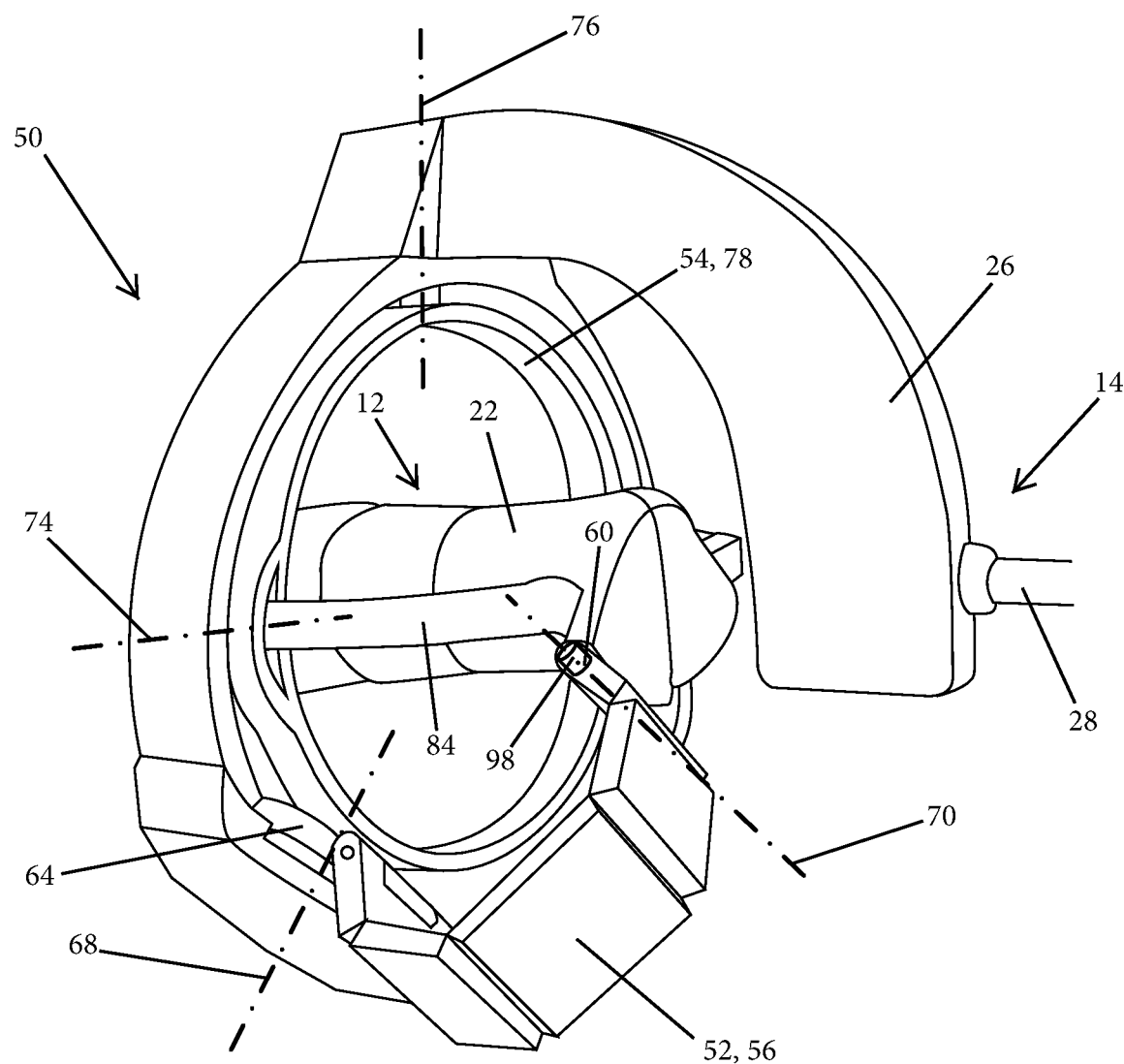
FIG. 24 is a perspective view of an embodiment of the second architecture (II) of the handle assembly and frame assembly of the surgical tool assembly.

The embodiment of FIG. 24 presents the surgical tool 10 and assembly thereof consisting of the handle assembly 12 and frame assembly 14 that exhibit the second architecture II. In architecture II, as set forth above, the SK AIJ 32 is provided and is a non-VC joint, and the SK AGJ 50 is provided and the VC-AGJ 86 is established. This embodiment maps to the schematic diagram of FIG. 6. With reference to FIG. 24, the AGJ 50 of architecture II can be similar to the AGJ 50 presented in FIGS. 15 and 16. In FIG. 24, and as before, the AGJ 50 provides the translation degree of constraint along the shaft axis 30 between the handle assembly 12 and the frame assembly 14, among the other translation degrees of constraint provided by the AGJ 50 between the handle assembly 12 and the frame assembly 14 (i.e., y-axis and z-axis). Unlike other embodiments, the second pulley axis 70 of the AIJ 32 is established between the handle assembly 12 and the first intermediate body 56. The second pulley axis 70 is along the first pin joint 60 thereat, and the first and second pulley axes 68, 70 do not intersect (hence, non-VC AIJ joint). Here, the first intermediate body 56 is a compliant member which allows for rotation of the handle assembly 12 about the VC-AGJ 86. And unlike other embodiments, a rotary encoder 98 is situated at the first pin joint 60 between the handle assembly 12 and the first intermediate body 56. The rotary encoder 98 serves to capture rotation about the second pulley axis 70. As in previous embodiments, the first intermediate body 56 rotates with respect to the frame assembly 12 and frame 26 via the first pulley 64 and about the first pulley axis 68. Rotation of handle assembly 12 and thereby the first intermediate body 56 about the first pulley axis 68 may connect to a mechanism transmission assembly that terminates at the EE assembly 16.

3.3 Architecture III

Figure 25:
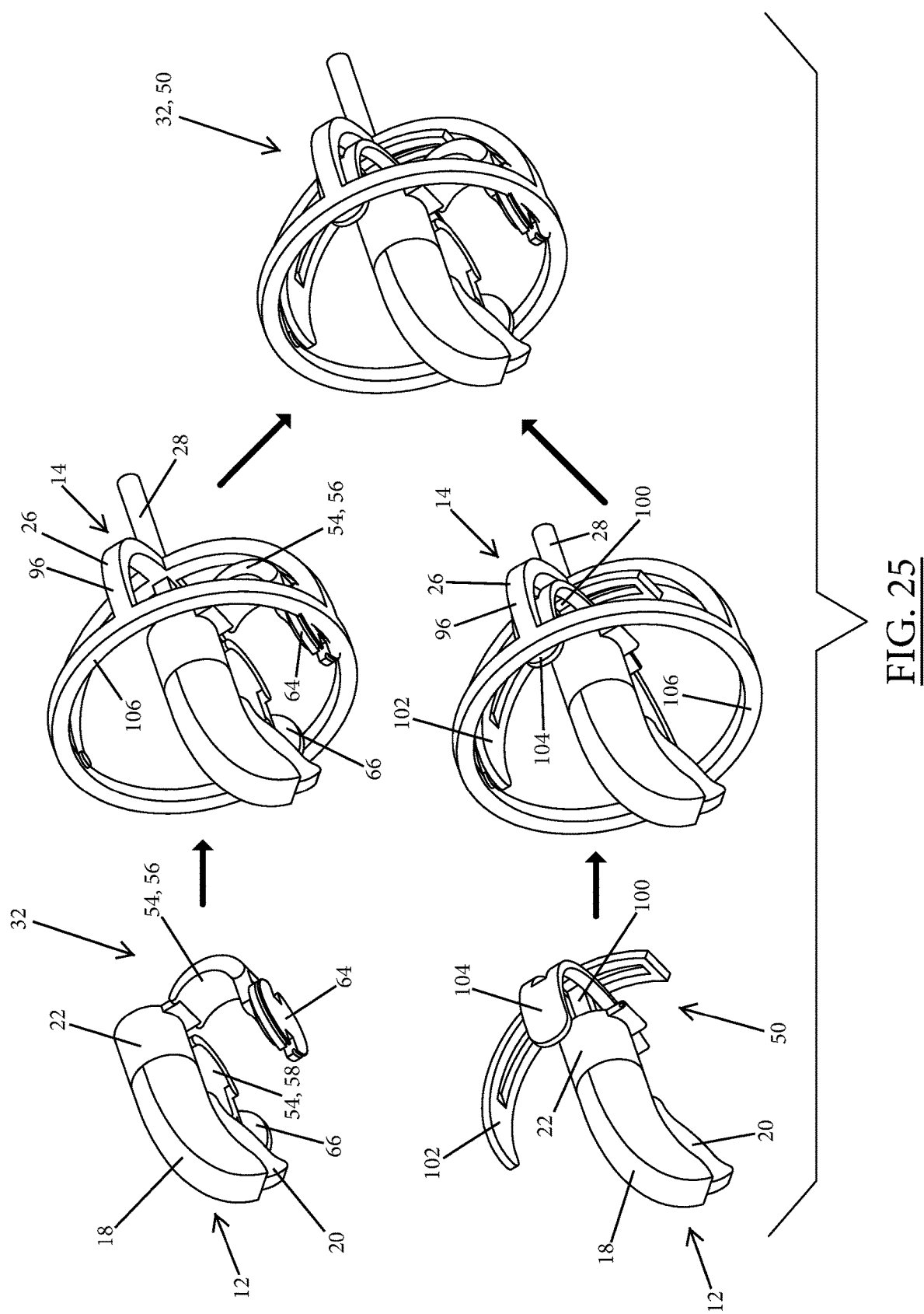
FIG. 25 is a schematic depiction of assemblage of an embodiment of the third architecture (III) of the handle assembly and frame assembly of the surgical tool assembly.

The embodiment of FIG. 25 presents the surgical tool 10 and assembly thereof consisting of the handle assembly 12 and frame assembly 14 that exhibit the third architecture III. In architecture III, as set forth above, the PK AIJ 32 is provided and the VC-AIJ 72 is established, and the PK AGJ 50 is provided and the VC-AGJ 86 is established. This embodiment maps to the schematic diagram of FIG. 7. With reference to FIG. 25, the PK AIJ 32 of architecture III can be similar to the AIJ 32 of architecture I and presented in FIGS. 9-23, 28, and 32. Unlike previous embodiments, the PK AGJ 50 includes a constraint peg 100 which facilitates the translation degree of constraint along the shaft axis 30 between the handle assembly 12 and the frame assembly 14 provided by the AGJ 50. The constraint peg 100 can be a rigid body extension of the handle assembly 12 and of the dial 22. As before, the AGJ 50 also provides translation degrees of constraint in the y-axis and z-axis between the handle assembly 12 and the frame assembly 14. Further, a fourth intermediate body 102 and a fifth intermediate body 104 are provided in the third architecture III as part of the AGJ 50. The fourth and fifth intermediate bodies 102, 104 are able to rotate about the pitch and yaw axes 74, 76, respectively, and with respect to the frame 26 and its extension arms 96 in order to furnish two DoF motion of the handle assembly 12. The extension arms 96 in FIG. 25 present a full ring shape, as indicated by reference numeral 106.

3.4 Architecture IV

Figure 26:
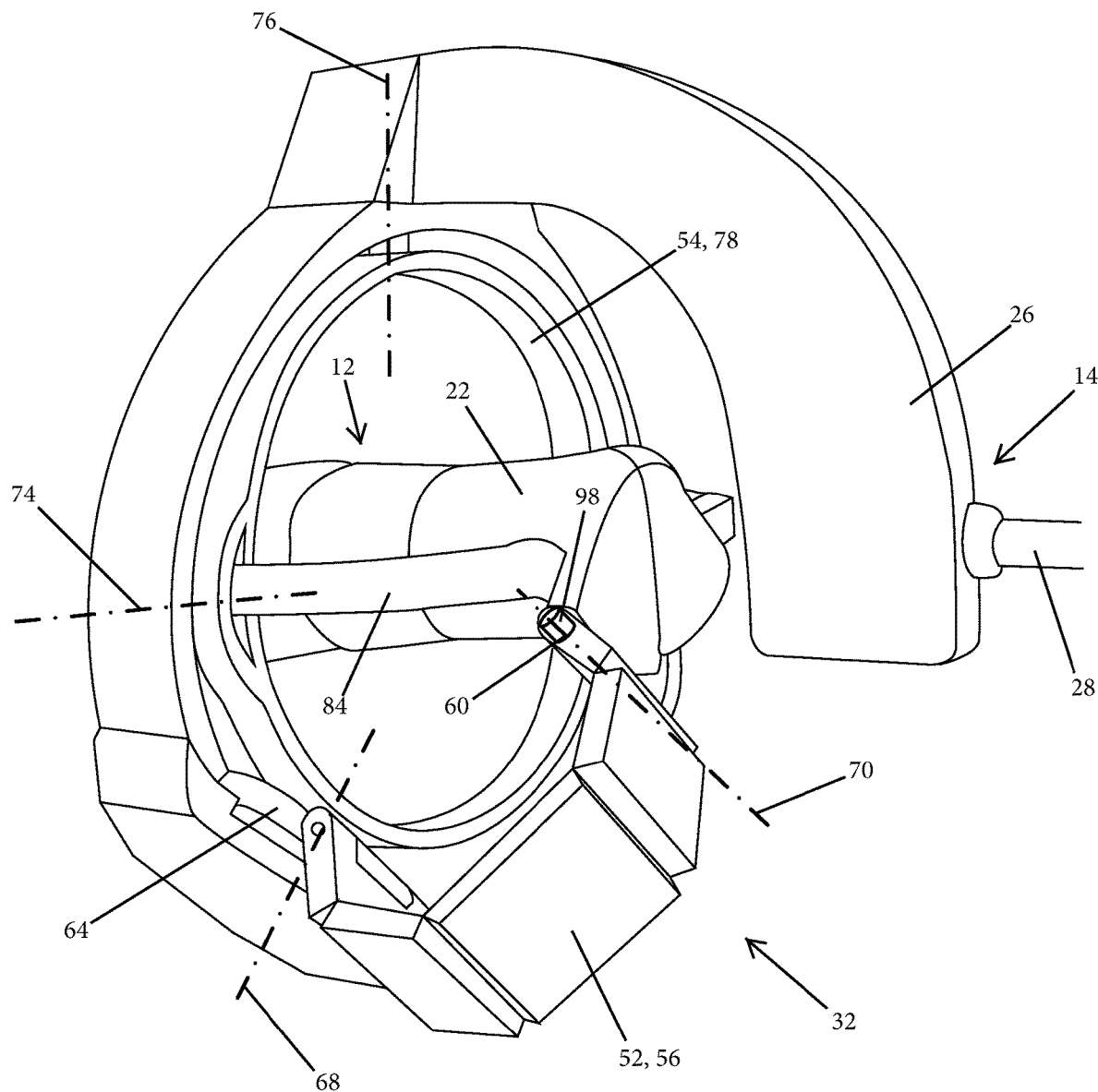
FIG. 26 is a perspective view of some components of an embodiment of the fourth architecture (IV) of the handle assembly and frame assembly of the surgical tool assembly, this view demonstrating an articulation input joint thereof.
Figure 27:
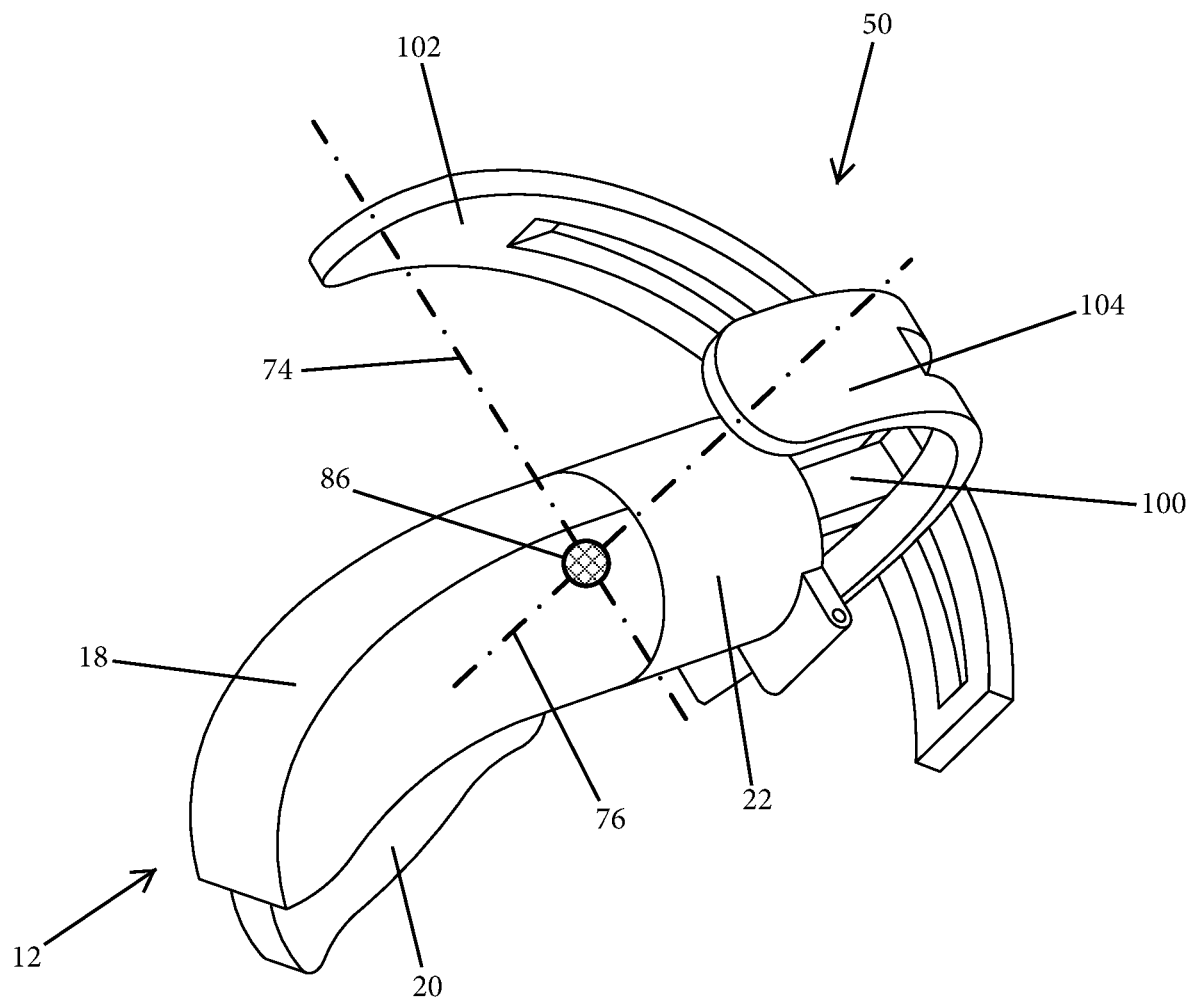
FIG. 27 is a perspective view of other components of the handle assembly and frame assembly of FIG. 26, this view demonstrating an axial grounding joint thereof.

The embodiment of FIGS. 26 and 27 present the surgical tool 10 and assembly thereof consisting of the handle assembly 12 and frame assembly 14 that exhibit the fourth architecture IV. Combining the components and assemblies of the AIJ 32 of FIG. 26 (as described with reference to FIG. 24 and architecture II) with the AGJ 50 of FIG. 27 (as described with reference to FIG. 25 and architecture III) provides the fourth architecture IV. In architecture IV, as set forth above, the SK AIJ 32 is provided and is a non-VC joint, and the PK AGJ 50 is provided and the VC-AGJ 86 is established. This embodiment maps to the schematic diagram of FIG. 8. The constraint peg 100 facilitates the translation degree of constraint along the shaft axis 30 between the handle assembly 12 and the frame assembly 14 provided by the AGJ 50. The AGJ 50 also provides translation degrees of constraint in the y-axis and z-axis between the handle assembly 12 and the frame assembly 14. The fourth intermediate body 102 and the fifth intermediate body 104 are provided in the fourth architecture IV as part of the AGJ 50.

Other Types of Transmission Members

Figure 28:
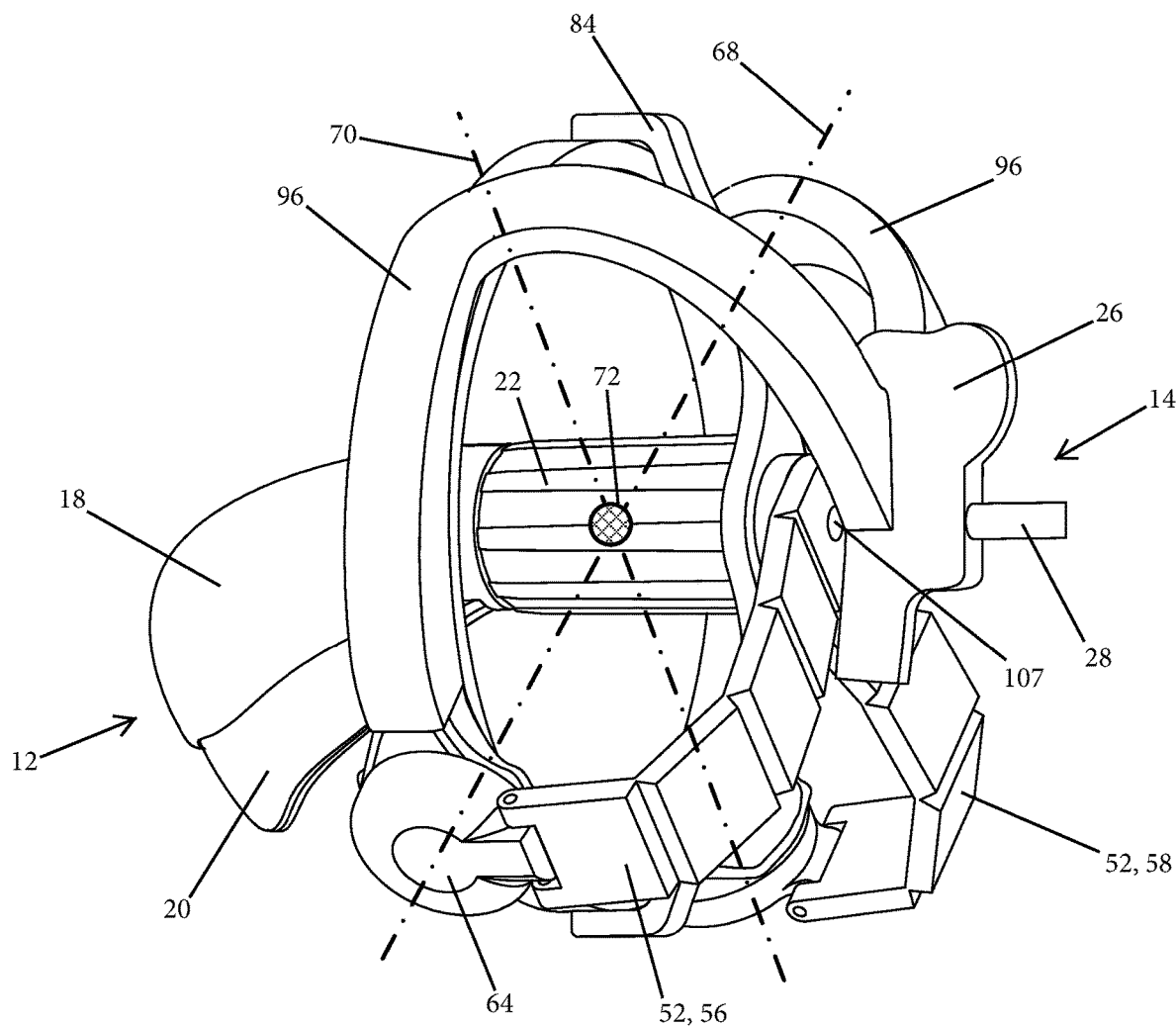
FIG. 28 is a perspective view of another embodiment of the first architecture (I) of the handle assembly and frame assembly of the surgical tool assembly.
Figure 29:
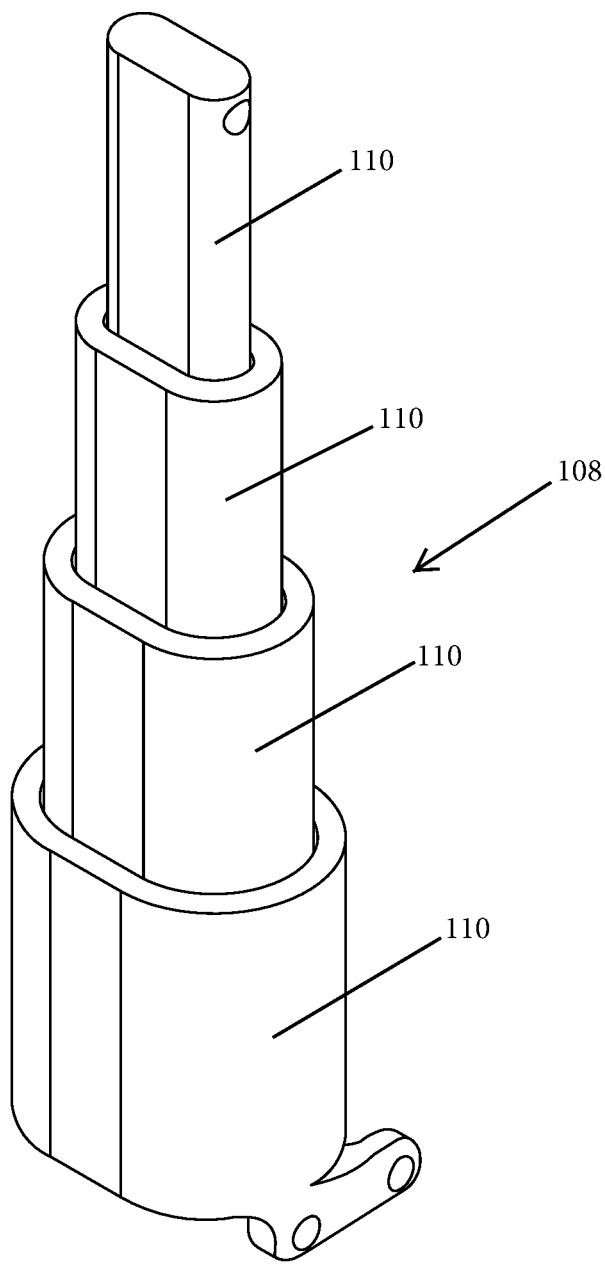
FIG. 29 is an embodiment of a telescoping transmission member.
Figure 30:
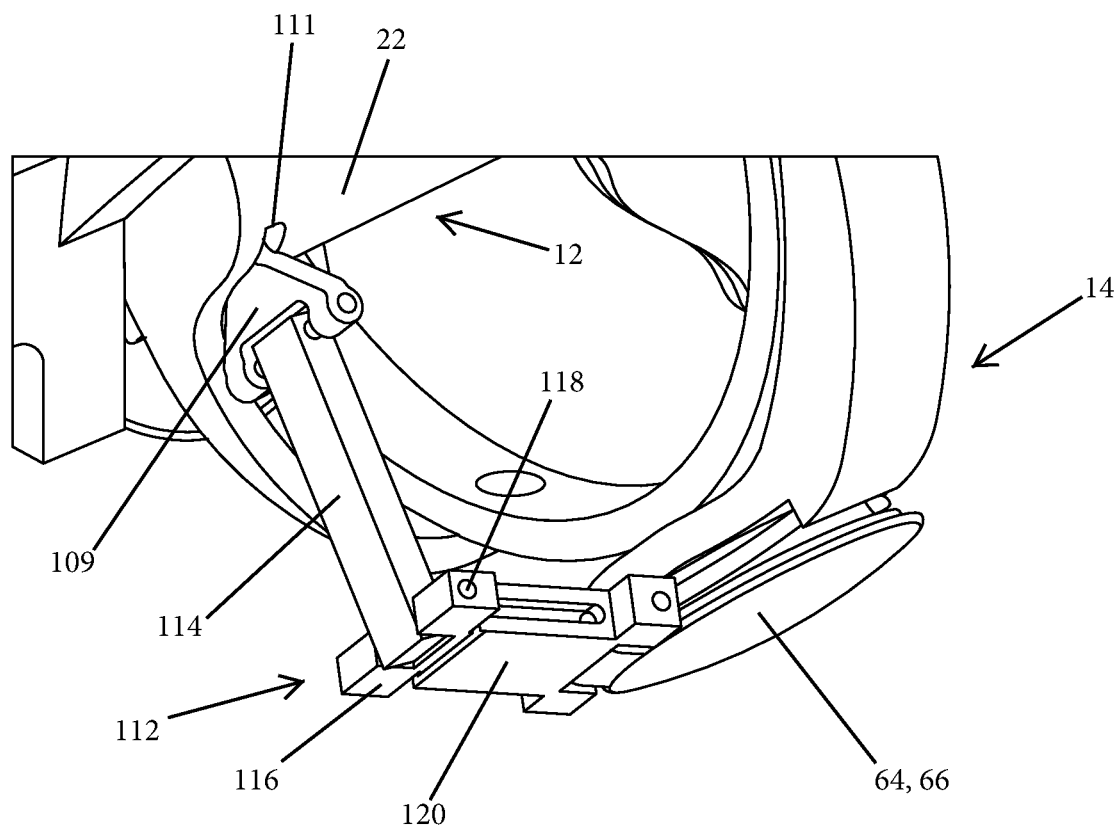
FIG. 30 is an embodiment of an extendable transmission member.
Figure 31:
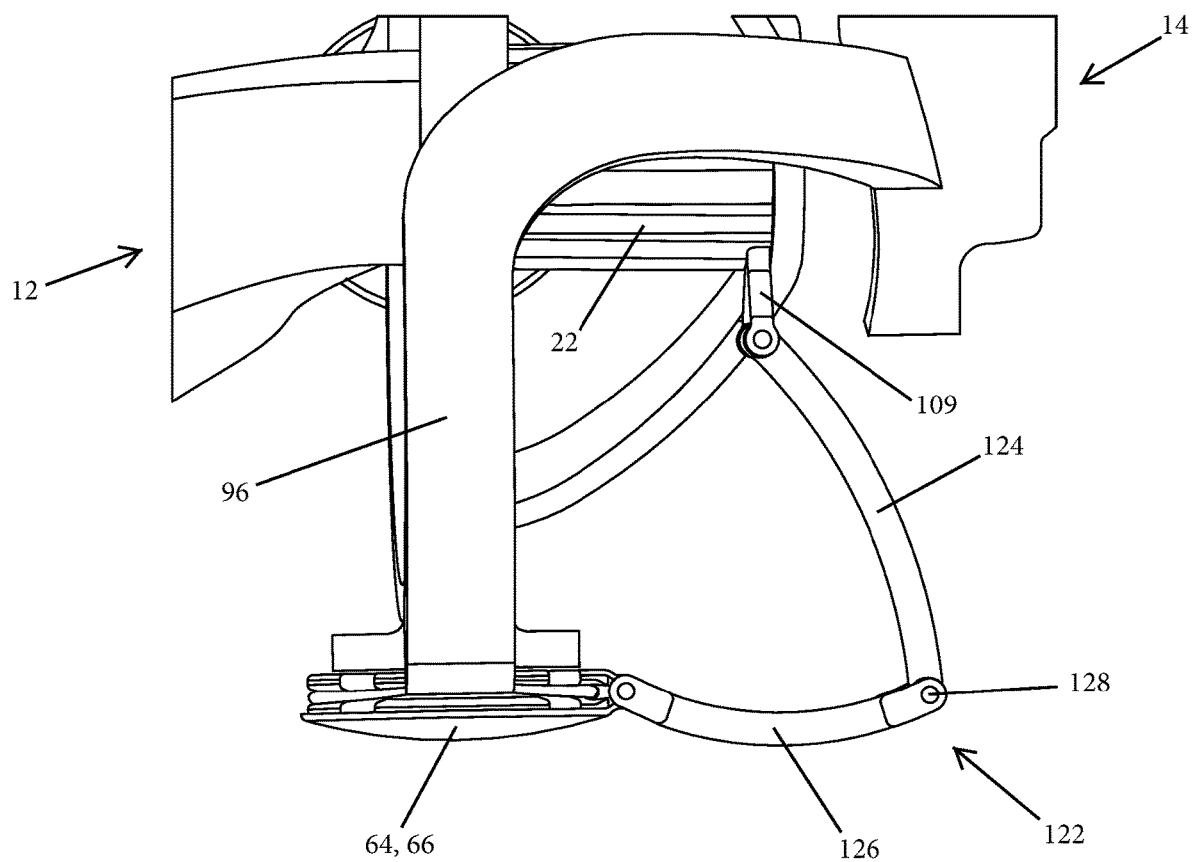
FIG. 31 is an embodiment of a curved transmission member.

Furthermore, for embodiments of the surgical tool 10 that employ the flex strips 52 as an intermediate body—for example, the embodiments of architecture I—the flex strips 52 could take a different form and could be replaced by other types of transmission members. When employed in embodiments of the first architecture I, an additional rotational DoF may be furnished between the flex strips 52 (and transmission members) and the handle assembly 12 about the handle axis 24 in order to preclude an unwanted binding condition that might otherwise arise. In FIG. 28, a joint 107 provides the rotational DoF between the flex strips 52 and an end of the handle assembly 12 (e.g., dial 22) about the handle axis 24. The joint 107 can be a pin joint, for instance. One example of a type of transmission member is presented in FIG. 29. A telescoping transmission member 108 can be connected between the handle and frame assemblies 12, 14 via hinged joints. One of the hinged joints is at the handle assembly 12, and can be at the dial 22; the other of the hinged joints is at the first or second pulleys 64, 66. The hinged joint at the dial 22 is, in this embodiment, via a tab 109 (FIGS. 30, 31). The tab 109 furnishes the additional rotational DoF between the telescoping transmission member 108 (as well as the transmission members set forth in this paragraph) and the handle assembly 12 about the handle axis 24 in order to preclude the unwanted binding condition. A slot 111 accommodates the additional rotational DoF. Individual bodies 110, four in total here, can expand and contract relative to one another in order to lengthen and shorten the overall extent of the telescoping transmission member 108. FIG. 30 presents another example. An extendable transmission member 112 can similarly be connected between the handle and frame assemblies 12, 14 via hinged joints. A first body 114 is hinged to the handle assembly 12. A slidable body 116 is hinged to the first body 114 via a hinged joint 118. The slidable body 116 slides and moves fore and aft relative to a second body 120, thereby lengthening and shortening the overall extent of the extendable transmission member 112. The second body 120 is hinged to the first and/or second pulley 64, 66. FIG. 31 presents yet another example. A curved transmission member 122 can similarly be connected between the handle and frame assemblies 12, 14 via hinged joints. A first curved body 124 is hinged to the handle assembly 12, and a second curved body 126 is hinged to the first and/or second pulley 64, 66. A hinged joint 128 connects the first and second curved bodies 124, 126 together. The transmission members 108, 112, and 122 have been found to resolve the unwanted binding condition that may arise in some circumstances amid use of the surgical tool 10. Moreover, the transmission members 108, 112, and 122 could replace the first and second intermediate bodies 54, 56 in the embodiments of FIGS. 9-23, 28, and 32.

3.5 Architecture V

The embodiments of FIGS. 34-40 present the surgical tool 10 and an assembly thereof consisting of the handle assembly 12 and frame assembly 14 that exhibit the fifth architecture V. In architecture V, as set forth above, the SK AIJ 32 is provided, the SK AGJ 50 is provided, and the VC-AIJ 72 and VC-AGJ 86 are established. These embodiments map to the schematic diagram of FIG. 33. As before, the VC-AIJ 72 and VC-AGJ 86 exhibit a generally coincident arrangement relative to each other, and the handle axis 24 and the shaft axis 30 exhibit a generally intersecting arrangement with the VC-AIJ 72 and with the VC-AGJ 86. In architecture V, the VC-AIJ 72 resides at a location that is occupied by the handle assembly 12, can reside at a location that is occupied by the user's hand 94 when the user is grasping the handle assembly 12 in order to manipulate the handle assembly 12, or can reside at both locations when those locations are one and the same. In a similar way, the VC-AGJ 86 resides at a location that is occupied by the handle assembly 12, can reside at a location that is occupied by the user's hand 94 when the user is grasping the handle assembly 12 in order to manipulate the handle assembly 12, or can reside at both locations when those locations are one and the same. The AGJ 50 provides the translation degree of constraint along the shaft axis 30 between the handle assembly 12 and the frame assembly 14, or along the x-axis, and provides the translation degrees of constraint between the handle assembly 12 and the frame assembly 14 in the y-axis and the z-axis. Unlike previous embodiments, in architecture V and in the embodiments of FIGS. 34-40, the first pulley axis 68 coincides and corresponds with the pitch axis 74, and the second pulley axis 70 similarly coincides and corresponds with the yaw axis 76. In other words, the first pulley axis 68 and pitch axis 74 constitute one and the same axis, and the second pulley axis 70 and yaw axis 76 constitute one and the same axis.

A first intermediate body 130 extends from the handle assembly 12, and particularly from the dial 22. The first intermediate body 130 is a rigid body. End-to-end over its full extent, the first intermediate body 130 has an arcuate profile and a half-ring shape. The first intermediate body 130 is rigidly fixed to the handle assembly 12, and can be a unitary extension thereof and a unitary extension of the dial 22. Indeed, the first intermediate body 130 can be a constituent part of the handle assembly 12, and hence could be considered a part of the handle assembly 12. In this embodiment, there is no relative movement between the first intermediate body 130 and the dial 22 amid use of the surgical tool 10. A second intermediate body 132 extends from the frame assembly 14, and particularly from the shaft 28 or from a shaft mount 134. The second intermediate body 132 is a rigid body. End-to-end over its full extent, the second intermediate body 132 has an arcuate profile and a half-ring shape. The second intermediate body 132 is rigidly fixed to the frame assembly 14, and can be a unitary extension thereof and a unitary extension of the shaft 28 or shaft mount 134. Indeed, the second intermediate body 132 can be a constituent part of the frame assembly 14, and hence could be considered a part of the frame assembly 14. In this embodiment, there is no relative movement between the second intermediate body 132 and the shaft 28 amid use of the surgical tool 10.

The third intermediate body 78, or deviation ring, is joined to the first intermediate body 130 via a first joint or the fourth set of pin joints 82, and is joined to the second intermediate body 132 via a second joint or the third set of pin joints 80. Over its full extent, the third intermediate body 78 has a full-ring shape. The third intermediate body 78 is a rigid body. The fourth set of pin joints 82 provides a yaw DoF joint between the first intermediate body 130 and the third intermediate body 78. The third set of pin joints 80 provides a pitch DoF joint between the second intermediate body 132 and the third intermediate body 78. The fourth set of pin joints 82 constitutes the sole connection and joint between the first intermediate body 130 and the third intermediate body 78, and, likewise, the third set of pin joints 80 constitutes the sole connection and joint between the second intermediate body 132 and the third intermediate body 78. The fourth set of pin joints 82 includes a pair of individual pin joints 82 distanced one-hundred-and-eighty degrees (180°) apart from each other over the circumference of the third intermediate body 78. Similarly, the third set of pin joints 80 includes a pair of individual pin joints 80 distanced one-hundred-and-eighty degrees (180°) apart from each other over the circumference of the third intermediate body 78. Relative to one another, individual pin joints 80, 82 are orthogonally arranged, and distanced ninety degrees (90°) apart over the circumference of the third intermediate body 78.

At one of the pair of individual pin joints 82, the second pulley 66 is situated and captures yaw rotation of the first intermediate body 130 with respect to the third intermediate body 78 about the second pulley axis 70 and about the yaw axis 76. As previously described, the captured yaw rotation is transmitted to the EE assembly 16 via the articulation transmission member which may be in the form of a wire or cable of the second pulley 66 that is routed to the EE assembly 16. At one of the pair of individual pin joints 80, the first pulley 64 is situated and captures pitch rotation of the second intermediate body 132 with respect to the third intermediate body 78 about the first pulley axis 68 and about the pitch axis 74. As previously described, the captured pitch rotation is transmitted to the EE assembly 16 via the articulation transmission member which may be in the form of a wire or cable of the first pulley 64 that is routed to the EE assembly 16.

Figure 38:
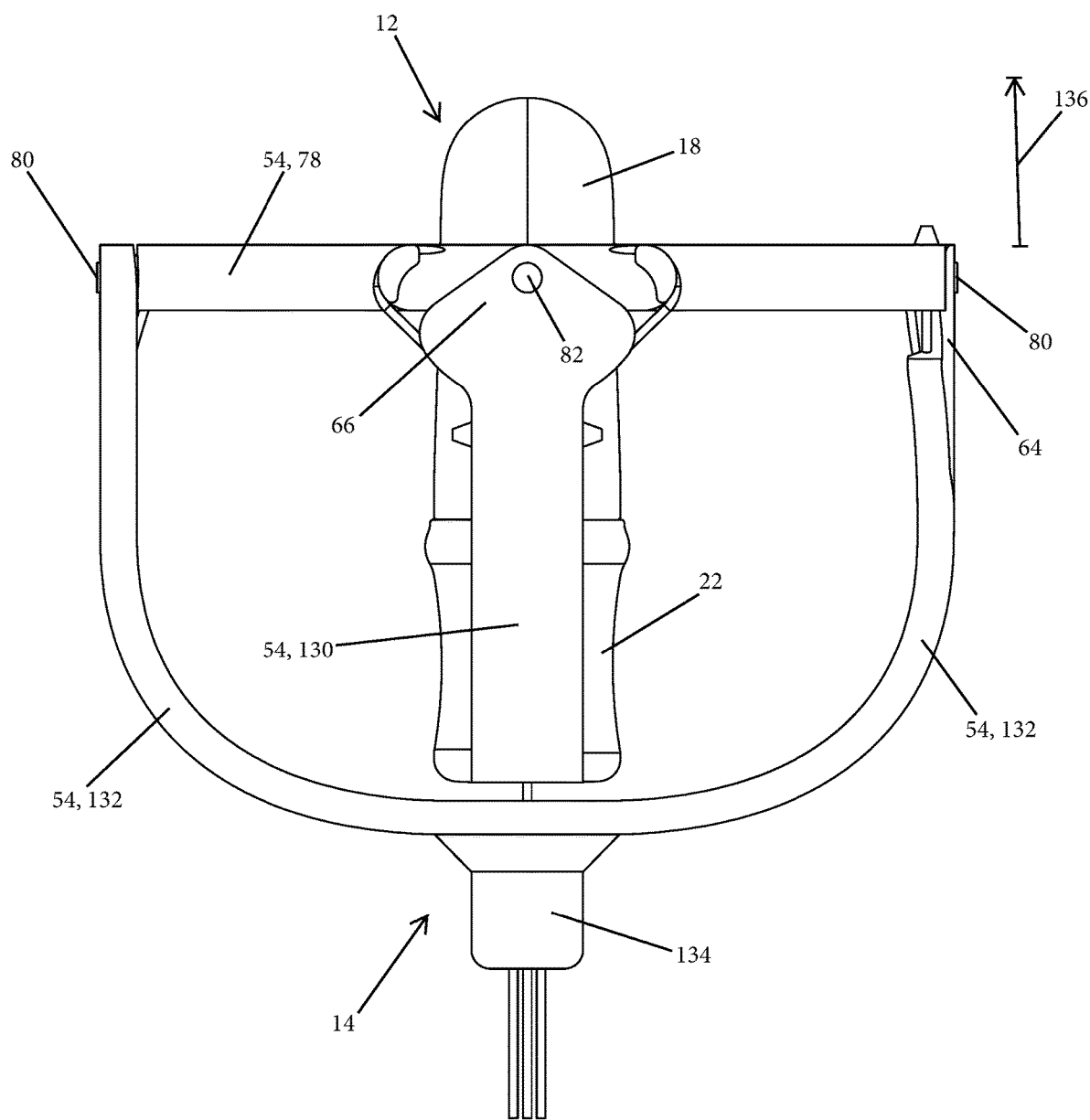
FIG. 38 is a top view of the surgical tool assembly of FIG. 34.
Figure 39:
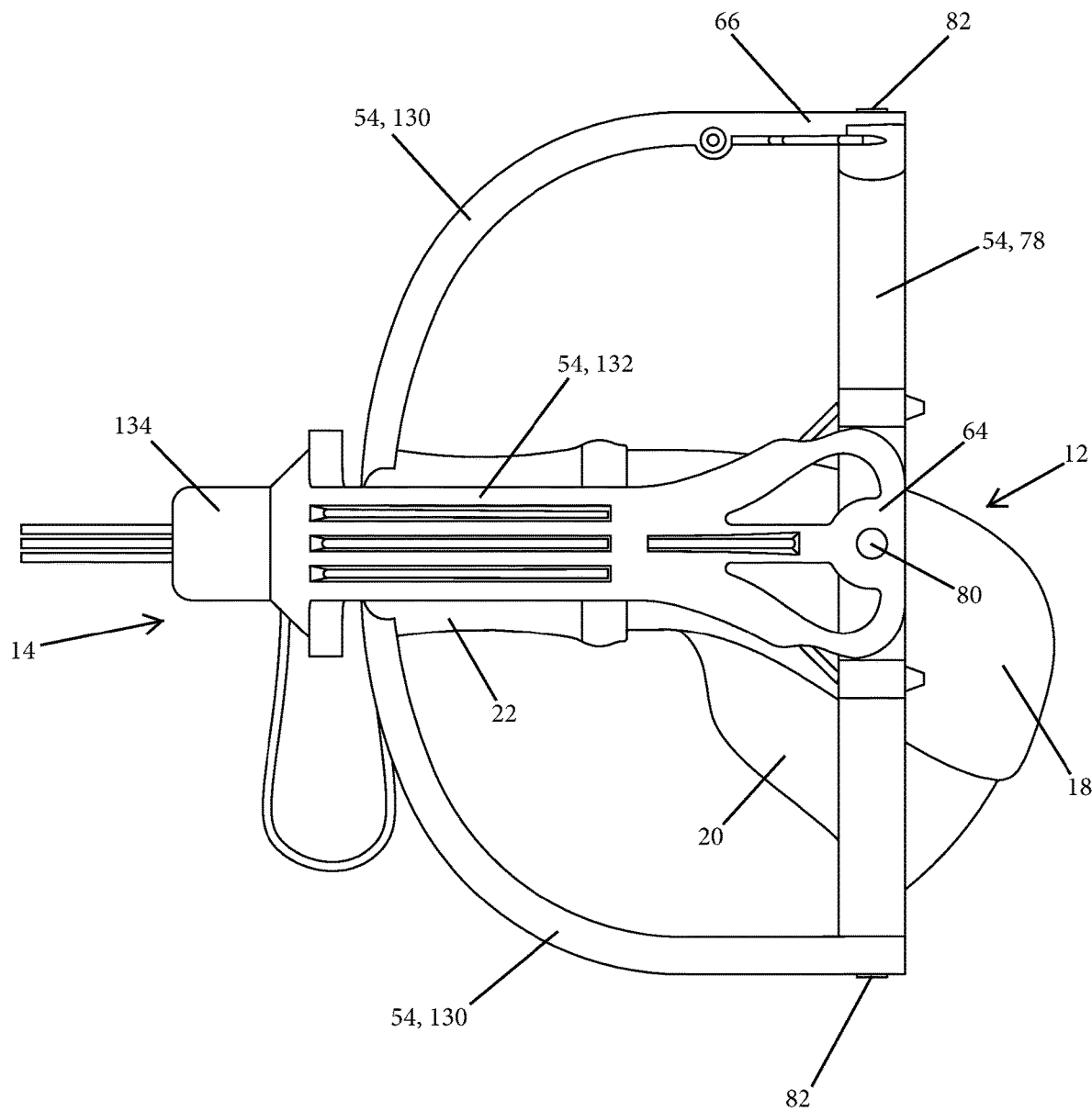
FIG. 39 is a side view of the surgical tool assembly of FIG. 34.

In yet another embodiment of the fifth architecture V similar to the embodiment presented particularly by FIGS. 34-39, the third intermediate body 78 can be set back farther rearward relative to the handle assembly 12 than shown. The handle assembly 12 would remain in its location illustrated. This possibility is represented in FIG. 38 by the arrowed line 136. The first and second intermediate bodies 130, 132 would in turn have greater rearward extents to make their respective connections to the third intermediate body 78 and hence serve to position the third intermediate body 78. The effect of this embodiment would be to locate the VC-AIJ 72 and the VC-AGJ 86 farther rearward of the handle assembly 12, and even distanced beyond the handle assembly 12. The VC-AIJ 72 and VC-AGJ 86 could then be located closer to a user's palm, for instance.

Figure 40:
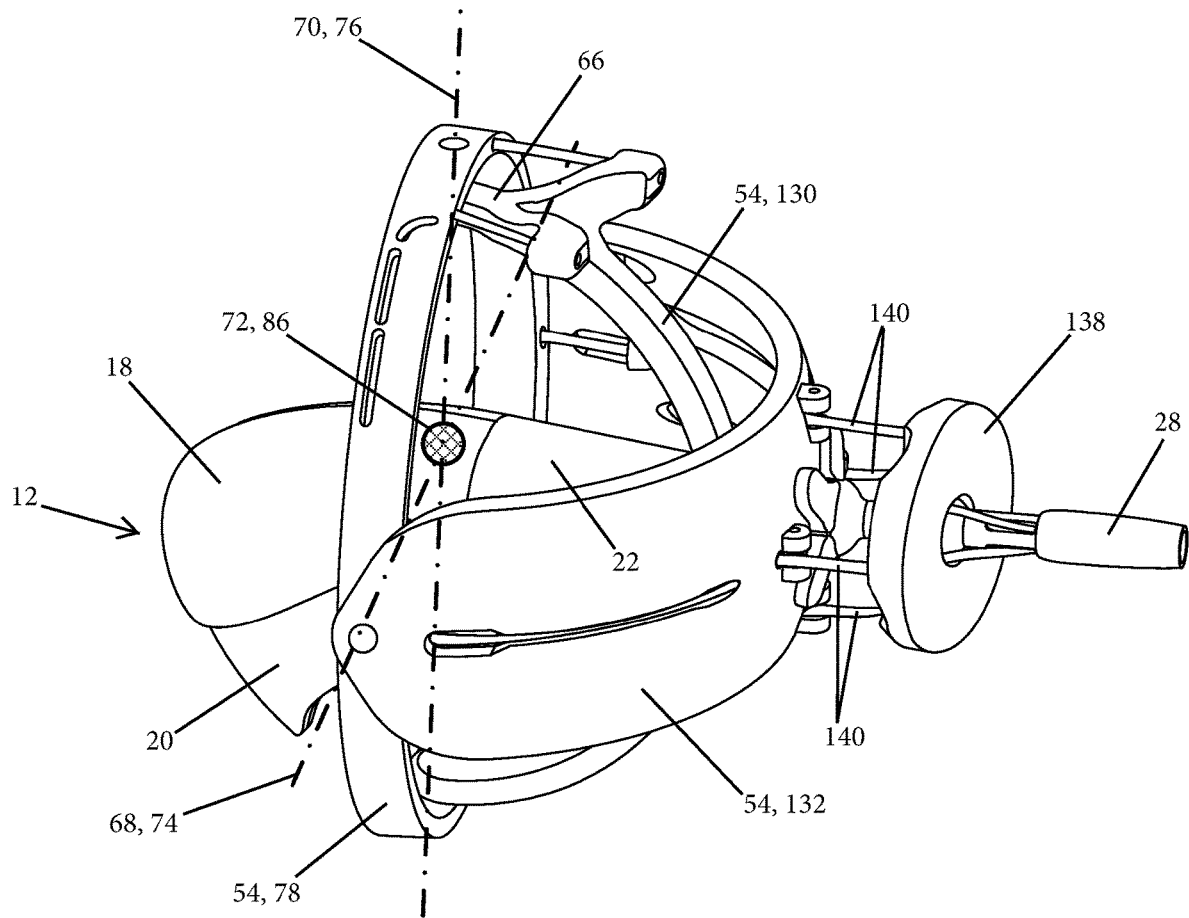
FIG. 40 is a perspective view of another embodiment of the fifth architecture (V) of the handle assembly and frame assembly of the surgical tool assembly.

With particular reference now to FIG. 40, in this embodiment of architecture V, a swash plate 138 is furnished adjacent the shaft 28. The articulation transmission members in the form of wires or cables 140, for example, of the first and second pulleys 64, 66 are routed through the swash plate 138 in order to provide a means to modify a transmission ratio between handle rotation and EE assembly 16 articulation depending on the desired force or motion of handle input and EE output. Different ratios, per this embodiment, can be effected by radially changing the termination or grounding points of input wires 140 (from the frame 26) and output wires 140 (to the EE assembly 16). Further, the swash plate 138 would effect a smoother transition of forces and cable pulls when the handle assembly 12 is articulated in different directions since the cables are connected to the same plate.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing embodiments only and is not intended to be limiting of the invention. For example, as used herein, the singular forms "a," "an," and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

Although various illustrative embodiments are described above, any of several changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

While embodiments of the invention have been illustrated and described, it is not intended that these embodiments illustrate and describe all possible forms of the invention. It is understood that the features of various implementing embodiments may be combined to form further embodiments of the invention. The words used in the specification are words of description rather than limitation, and it is under stood that various changes may be made without departing from the spirit and scope of the invention.

The examples and illustrations included herein show, by way of illustration and not of limitation, specific embodiments in which the subject matter may be practiced. These embodiments consist of bodies that have various types of joints and/or mechanisms namely, prismatic, revolute, cylindrical, etc. between them. These joints and/or mechanisms may consist of discrete elements/bodies/component or these joint/mechanisms may be created by compliant extensions of other bodies and/or assembles.

It is to be understood that the foregoing description is not a definition of the invention, but is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," and "such as," and the verbs "comprising," "having," "including," and their other verb forms, when used in conjunction with a listing of one or more components or other items, are each to be construed as open-ended, meaning that that the listing is not to be considered as excluding other, additional components or items. Other terms are to be construed using their broadest reasonable meaning unless they are used in a context that requires a different interpretation.

The invention claimed is:

1. A surgical tool assembly, comprising:
a handle assembly;
a frame assembly;
at least one intermediate body coupled between said handle assembly and said frame assembly;
a plurality of joints residing among said handle assembly, said frame assembly, and said at least one intermediate body;
an articulation input joint established between said handle assembly and said frame assembly via said at least one intermediate body and via said plurality of joints, said articulation input joint providing a pitch rotational degree of freedom or a yaw rotational degree of freedom or both a pitch and a yaw rotational degree of freedom at at least one of said plurality of joints and providing a pitch rotational degree of freedom or a yaw rotational degree of freedom or both a pitch and a yaw rotational degree of freedom at at least another of said plurality of joints, said articulation input joint having a first virtual center; and
a grounding joint established between said handle assembly and said frame assembly via said at least one intermediate body and via said plurality of joints, said grounding joint having a second virtual center;
wherein said handle assembly establishes a first axis, a shaft of said frame assembly establishes a second axis, said first axis generally intersects said first virtual center of said articulation input joint and generally intersects said second virtual center of said grounding joint, and said second axis generally intersects said first virtual center of said articulation input joint and generally intersects said second virtual center of said grounding joint, and wherein said handle assembly is translationally constrained along an x-axis relative to said frame assembly via said grounding joint, wherein said second axis and said x-axis exhibit a generally coincident arrangement relative to each other.

2. The surgical tool assembly as set forth in claim 1, wherein said handle assembly is translationally constrained along a y-axis relative to said frame assembly via said grounding joint.

3. The surgical tool assembly as set forth in claim 1, wherein a pitch motion path of said articulation input joint and a yaw motion path of said articulation input joint exhibit a parallel kinematic arrangement with respect to each other.

4. The surgical tool assembly as set forth in claim 1, wherein rigid body motion transmission paths effected via said grounding joint exhibit a serial kinematic arrangement.

5. The surgical tool assembly as set forth in claim 1, wherein said handle assembly is translationally constrained along a z-axis relative to said frame assembly via said grounding joint.

6. The surgical tool assembly as set forth in claim 1, wherein said first axis is arranged longitudinally through said handle assembly, and wherein, when said handle assembly lacks rotation, said first axis and said second axis exhibit a generally coincident arrangement relative to each other.

7. The surgical tool assembly as set forth in claim 1, wherein said first virtual center of said articulation input joint resides at a location that is occupied by said handle assembly, by a user's hand when manipulating said handle assembly amid use of the surgical tool assembly, or by both said handle assembly and the user's hand when manipulating said handle assembly amid use of the surgical tool assembly.

8. The surgical tool assembly as set forth in claim 1, wherein said second virtual center of said grounding joint resides at the location that is occupied by said handle assembly, by the user's hand when manipulating said handle assembly amid use of the surgical tool assembly, or by both said handle assembly and the user's hand when manipulating said handle assembly amid use of the surgical tool assembly.

9. A surgical tool assembly, comprising:
a handle assembly establishing a handle axis;
a frame assembly, said frame assembly having a shaft, said shaft establishing a shaft axis;
a first intermediate rigid body extending from said handle assembly;
a second intermediate rigid body extending from said frame assembly;
a third intermediate rigid body;
a first joint residing between said first intermediate rigid body and said third intermediate rigid body, said first joint providing a pitch rotational degree of freedom or a yaw rotational degree of freedom of said first intermediate rigid body with respect to said third intermediate rigid body; and
a second joint residing between said second intermediate rigid body and said third intermediate rigid body, said second joint providing a pitch rotational degree of freedom or a yaw rotational degree of freedom of said third intermediate rigid body with respect to said second intermediate rigid body, the pitch or yaw rotational degree of freedom provided by said second joint being opposite the pitch or yaw rotational degree of freedom provided by said first joint;
wherein a virtual center of rotation established by said first joint and by said second joint resides at a location that is occupied by said handle assembly, by a user's hand when manipulating said handle assembly amid use of the surgical tool assembly, or by both said handle assembly and the user's hand when manipulating said handle assembly amid use of the surgical tool assembly;
wherein said handle assembly is translationally constrained along a y-axis relative to said frame assembly via said first intermediate rigid body, said second intermediate rigid body, and said third intermediate rigid body, said handle axis generally intersects said virtual center of rotation and said shaft axis generally intersects said virtual center of rotation, wherein an x-axis of the surgical tool assembly coincides with said shaft axis, said y-axis is oriented orthogonal to said x-axis and vertical relative to said x-axis, and a z-axis of the surgical tool assembly is oriented orthogonal to said x-axis and horizontal relative to said x-axis.

10. The surgical tool assembly as set forth in claim 9, wherein said handle axis is arranged longitudinally through said handle assembly, and wherein, when said handle assembly lacks rotation, said handle axis and said shaft axis exhibit a generally coincident arrangement relative to each other.

11. The surgical tool assembly as set forth in claim 9, wherein said handle assembly is translationally constrained along said x-axis relative to said frame assembly via said first intermediate rigid body, said second intermediate rigid body, and said third intermediate rigid body.

12. The surgical tool assembly as set forth in claim 9, wherein said handle assembly is translationally constrained along said z-axis relative to said frame assembly via said first intermediate rigid body, said second intermediate rigid body, and said third intermediate rigid body.

13. A surgical tool assembly, comprising:
a handle assembly establishing a handle axis, a first intermediate rigid body rigidly fixed to said handle assembly;
a frame assembly having a shaft, said shaft establishing a shaft axis, a second intermediate rigid body rigidly fixed to said frame assembly; and
a deviation ring joined to said first intermediate rigid body via a first joint and joined to said second intermediate rigid body via a second joint, said first joint providing a pitch rotational degree of freedom or a yaw rotational degree of freedom and said second joint providing the other of the pitch rotational degree of freedom or the yaw rotational degree of freedom, a first pulley situated at said first joint and a second pulley situated at said second joint;
wherein said handle assembly is translationally constrained along a z-axis relative to said frame assembly via said first intermediate rigid body, said second intermediate rigid body, and said deviation ring.

14. The surgical tool assembly as set forth in claim 13, wherein, when said handle assembly lacks rotation about said first joint and lacks rotation about said second joint, said handle axis and said shaft axis are arranged generally coincident with respect to each other.

15. The surgical tool assembly as set forth in claim 13, wherein said handle assembly is translationally constrained along an x-axis relative to said frame assembly via said first intermediate rigid body, said second intermediate rigid body, and said deviation ring.

16. The surgical tool assembly as set forth in claim 13, wherein said handle assembly is translationally constrained along a y-axis relative to said frame assembly via said first intermediate rigid body, said second intermediate rigid body, and said deviation ring.

17. The surgical tool assembly as set forth in claim 13, wherein a virtual center of rotation established via intersection of axes of rotation of said first joint and said second joint resides at a location that is occupied by said handle assembly, by a user's hand when manipulating said handle assembly amid use of the surgical tool assembly, or by both said handle assembly and the user's hand when manipulating said handle assembly amid use of the surgical tool assembly.

18. The surgical tool assembly as set forth in claim 17, wherein said handle axis generally intersects said virtual center of rotation and said shaft axis generally intersects said virtual center of rotation.

* * * * *